United States Patent
Bartha et al.

(10) Patent No.: US 10,415,091 B2
(45) Date of Patent: *Sep. 17, 2019

(54) METHODS AND SYSTEMS FOR GENETIC ANALYSIS

(71) Applicant: Personalis, Inc., Menlo Park, CA (US)

(72) Inventors: Gabor T. Bartha, Los Altos, CA (US); Gemma Chandratillake, Cambridge (GB); Richard Chen, Burlingame, CA (US); Sarah Garcia, Palo Alto, CA (US); Hugo Yu Kor Lam, Sunnyvale, CA (US); Shujun Luo, Castro Valley, CA (US); Mark R. Pratt, Roseburg, OR (US); John West, Cupertino, CA (US)

(73) Assignee: Personalis, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/996,215

(22) Filed: Jun. 1, 2018

(65) Prior Publication Data

US 2018/0327834 A1 Nov. 15, 2018

Related U.S. Application Data

(60) Continuation of application No. 14/810,337, filed on Jul. 27, 2015, which is a division of application No. 14/141,990, filed on Dec. 27, 2013, now Pat. No. 9,128,861.

(60) Provisional application No. 61/753,828, filed on Jan. 17, 2013.

(51) Int. Cl.
| | |
|---|---|
| C12Q 1/6874 | (2018.01) |
| G16B 20/00 | (2019.01) |
| G16B 30/00 | (2019.01) |
| G16B 99/00 | (2019.01) |
| C12Q 1/6806 | (2018.01) |
| C12Q 1/6869 | (2018.01) |
| G16B 35/00 | (2019.01) |
| G16C 20/60 | (2019.01) |

(52) U.S. Cl.
CPC ......... *C12Q 1/6874* (2013.01); *C12Q 1/6806* (2013.01); *G16B 20/00* (2019.02); *G16B 30/00* (2019.02); *G16B 99/00* (2019.02); *C12Q 1/6869* (2013.01); *G16B 35/00* (2019.02); *G16C 20/60* (2019.02)

(58) Field of Classification Search
None
See application file for complete search history.

(56) References Cited

U.S. PATENT DOCUMENTS

| | | |
|---|---|---|
| 9,128,861 B2 | 9/2015 | Bartha et al. |
| 9,745,626 B2 | 8/2017 | Bartha et al. |
| 2002/0006615 A1 | 1/2002 | Goldsborough et al. |
| 2005/0042668 A1 | 2/2005 | Perlin |
| 2006/0184489 A1 | 8/2006 | Weiner et al. |
| 2006/0278241 A1 | 12/2006 | Ruano |
| 2010/0042438 A1 | 2/2010 | Moore et al. |
| 2011/0009296 A1 | 1/2011 | Kain et al. |
| 2012/0270206 A1 | 10/2012 | Ginns, I et al. |
| 2016/0017417 A1 | 1/2016 | Gabor et al. |

FOREIGN PATENT DOCUMENTS

EP 0281927 A2 9/1988

OTHER PUBLICATIONS

Boers et al., "High-Throughput Multilocus Sequence Typing: Bringing Molecular Typing to the Next Level," PLoS One 2012, 7(7): e39630. (Year: 2012).*
Boers et al., "High-Throughput Multilocus Sequence Typing: Bringing Molecular Typing to the Next Level," PLoS One 2012; 7(7):e39630.
Clark, et al. Performance comparison of exome DNA sequencing technologies. Nat Biotechnol. Sep. 25, 2011;29(10):908-14. doi: 10.1038/nbt.1975.
Craig, et al. Identification of genetic variants using bar-coded multiplexed sequencing. Nat Methods. Oct. 2008;5(10):887-93. doi: 10.1038/nmeth.1251. Epub Sep. 14, 2008.
European search report and opinion dated Aug. 4, 2016 for EP Application No. 13871784.
Gottlieb, et al. The DiGeorge syndrome minimal critical region contains a goosecoid-like (GSCL) homeobox gene that is expressed early in human development. Am J Hum Genet. May 1997;60(5):1194-201.
International search report and written opinion dated Apr. 23, 2014 for PCT/US2013/078123.
Li, et al. Novel computational methods for increasing PCR primer design effectiveness in directed sequencing. BMC Bioinformatics. Apr. 11, 2008;9:191. doi: 10.1186/1471-2105-9-191.
Notice of allowance dated Jun. 3, 2015 for U.S. Appl. No. 14/141,990.
Office action dated Feb. 6, 2015 for U.S. Appl. No. 14/141,990.
Office Action dated Feb. 27, 2017 for U.S. Appl. No. 15/222,875.

(Continued)

*Primary Examiner* — Kaijiang Zhang
(74) *Attorney, Agent, or Firm* — Wilson Sonsini Goodrich & Rosati

(57) ABSTRACT

This disclosure provides systems and methods for sample processing and data analysis. Sample processing may include nucleic acid sample processing and subsequent sequencing. Some or all of a nucleic acid sample may be sequenced to provide sequence information, which may be stored or otherwise maintained in an electronic storage location. The sequence information may be analyzed with the aid of a computer processor, and the analyzed sequence information may be stored in an electronic storage location that may include a pool or collection of sequence information and analyzed sequence information generated from the nucleic acid sample. Methods and systems of the present disclosure can be used, for example, for the analysis of a nucleic acid sample, for producing one or more libraries, and for producing biomedical reports. Methods and systems of the disclosure can aid in the diagnosis, monitoring, treatment, and prevention of one or more diseases and conditions.

26 Claims, 15 Drawing Sheets

(56) References Cited

OTHER PUBLICATIONS

Office action dated Jun. 5, 2014 for U.S. Appl. No. 14/141,990.
Human Genome Overview GRCh37. Genome Reference Consortium, Feb. 27, 2009. 1 Page.
Human Genome Overview GRCh37.p13. Genome Reference Consortium, Jun. 28, 2013. 2 Pages.
Human Genome Overview GRCh38.p12. Genome Reference Consortium, Dec. 21, 2017. 2 Pages.
Market, et al., V(D)J Recombination and the Evolution of the Adaptive Immune System. PLOS Biol. 2003; 1(1):e16. https://doi.org/10.1371/journal.pbio.0000016.
Notice of Allowance dated Jun. 9, 2017 for U.S. Appl. No. 15/222,875.
Ralph, et al., Consistency of VDJ Rearrangement and Substitution Parameters Enables Accurate B Cell Receptor Sequence Annotation. PLOS computational biology, 2016; 12(1): e1004409. https://doi.org/10.1371/journal.pcbi.1004409.
U.S. Appl. No. 14/810,337 Office Action dated Apr. 9, 2018.
U.S. Appl. No. 14/810,337 Notice of Allowance dated Feb. 28, 2019.
U.S. Appl. No. 14/810,337 Notice of Allowance dated Jan. 18, 2019.

* cited by examiner

METHODS AND SYSTEMS FOR GENETIC ANALYSIS

CROSS-REFERENCE

This application is a continuation application of U.S. patent application Ser. No. 14/810,337, filed Jul. 27, 2015, which application is a divisional application of U.S. patent application Ser. No. 14/141,990, filed Dec. 27, 2013, now U.S. Pat. No. 9,128,861, which claims priority to U.S. Provisional Application No. 61/753,828, filed Jan. 17, 2013, each of which is incorporated herein by reference in its entirety.

BACKGROUND

Current methods for whole genome and/or exome sequencing may be costly and fail to capture many biomedically important variants. For example, commercially available exome enrichment kits (e.g., Illumina's TruSeq exome enrichment and Agilent's SureSelect exome enrichment), may fail to target biomedically interesting non-exomic and exomic regions. Often, whole genome and/or exome sequencing using standard sequencing methods performs poorly in content regions having very high CG content (>70%). Furthermore, whole genome and/or exome sequencing also fail to provide adequate and/or cost-effective sequencing of repetitive elements in the genome.

The methods disclosed herein provide specialized sequencing protocols or technologies to address these issues.

SUMMARY

Provided herein is a method for analyzing a nucleic acid sample, comprising (a) producing two or more subsets of nucleic acid molecules from a nucleic acid sample, wherein (i) the two or more subsets comprise a first subset of nucleic acid molecules and a second subset of nucleic acid molecules, and (ii) the first subset of nucleic acid molecules differs from the second subset of nucleic acid molecules by one or more features selected from genomic regions, mean GC content, mean molecular size, subset preparation method, or combination thereof; (b) conducting one or more assays on at least two of the two or more subsets of nucleic acid molecules, wherein (i) a first assay, comprising a first sequencing reaction, is conducted on the first subset of the two or more subsets to produce a first result, and (ii) a second assay is conducted on the second subset of the two or more subsets to produce a second result; and (c) combining, with the aid of a computer processor, the first result and second result, thereby analyzing the nucleic acid sample.

Also provided herein is a method for analyzing a nucleic acid sample, comprising (a) producing two or more subsets of nucleic acid molecules from a nucleic acid sample, wherein the two or more subsets differ by one or more features selected from genomic regions, mean GC content, mean molecular size, subset preparation method, or combination thereof; (b) combining at least two of the two or more subsets of nucleic acid molecules to produce a first combined pool of nucleic acid molecules; and (c) conducting one or more assays on the first combined pool of nucleic acid molecules, wherein at least one of the one or more assays comprises a sequencing reaction.

Disclosed herein is a method for analyzing a nucleic acid sample, comprising (a) producing two or more nucleic acid molecules subsets from a nucleic acid sample, wherein producing the two or more nucleic acid molecules comprise enriching the two or more subsets of nucleic acid molecules for two or more different genomic regions; (b) conducting a first assay on a first subset of nucleic acid molecules among the two or more subsets of nucleic acid molecules to produce a first result, wherein the first assay comprises a first sequencing reaction; (c) conducting a second assay on at least a second subset of nucleic acid molecules among the two or more subsets of nucleic acid molecules to produce a second result; and (d) combining, with the aid of a computer processor, the first result with the second result, thereby analyzing the nucleic acid sample.

Further provided herein is a method for analyzing a nucleic acid sample, comprising (a) preparing at least a first subset of nucleic acid molecules and a second subset of nucleic acid molecules from a nucleic acid sample, wherein the first subset of nucleic acid molecules differs from the second subset of nucleic acid molecules; (b) conducting a first assay on the first subset of nucleic acid molecules and a second assay on the second subset of nucleic acid molecules, wherein the first assay comprises a nucleic acid sequencing reaction that produces a first result, comprising nucleic acid sequence information for the first subset, and wherein the second assay produces a second result; (c) analyzing, with the aid of a computer processor, the first result to provide a first analyzed result and analyzing the second result to provide a second analyzed result; and (d) combining, with the aid of a computer processor, the first and second analyzed results, thereby analyzing the nucleic acid sample.

Provided herein is a method for analyzing a nucleic acid, comprising (a) producing one or more subsets of nucleic acid molecules from a nucleic acid sample, wherein producing the one or more subsets of nucleic acid molecules comprises conducting a first assay in the presence of one or more antioxidants to produce a first subset of nucleic acid molecules; and (b) conducting a sequencing reaction on the one or more subsets of nucleic acid molecules, thereby analyzing the nucleic acid sample.

Also disclosed herein is a method for analyzing a nucleic acid sample, comprising (a) producing, with the aid of a computer processor, one or more capture probes, wherein the one or more capture probes hybridize to one or more polymorphisms, wherein the one or more polymorphisms are based on or extracted from one or more databases of polymorphisms, observed in a population of one or more samples, or a combination thereof; (b) contacting a nucleic acid sample with the one or more capture probes to produce one or more capture probe hybridized nucleic acid molecules; and (c) conducting a first assay on the one or more capture probe hybridized nucleic acid molecules, thereby analyzing the nucleic acid sample, wherein the first assay comprises a sequencing reaction.

Further disclosed herein is a method for developing complementary nucleic acid libraries, comprising (a) producing two or more subsets of nucleic acid molecules from a sample, wherein (i) the two or more subsets of nucleic acid molecules comprise a first subset of nucleic acid molecules and a second subset of nucleic acid molecules, (ii) the first subset of nucleic acid molecules comprises nucleic acid molecules of a first mean size, (iii) the second subset of nucleic acid molecules comprises nucleic acid molecules of a second mean size, and (iv) the first mean size of the first subset of nucleic acid molecules is greater than the second mean size of the second subset of nucleic acid molecules by about 200 or more residues; (b) producing two or more nucleic acid libraries, wherein (i) the two or more libraries comprise a first nucleic acid molecules library and second nucleic acid molecules library, (ii) the first nucleic acid molecules library comprises the one or more nucleic acid molecules from the first subset of nucleic acid molecules, (iii) the second nucleic acid molecules library comprises the one or more nucleic acid molecules from the second subset of nucleic acid molecules, and (iv) the content of the first nucleic acid molecules library is at least partially complementary to the content of the second nucleic acid molecules library.

Provided herein is a method for developing complementary nucleic acid libraries, comprising (a) producing two or more subsets of nucleic acid molecules from a sample of nucleic acid molecules, wherein the two or more subsets of nucleic acid molecules comprise a first subset of nucleic acid molecules and a second subset of nucleic acid molecules; (b) conducting two or more assays on the two or more subsets of nucleic acid molecules, wherein (i) the two or more assays comprise a first assay and a second assay, (ii) the first assay comprises conducting a first amplification reaction on the first subset of nucleic acid molecules to produce one or more first amplified nucleic acid molecules with a first mean GC content, (iii) the second assay comprises conducting a second amplification reaction on the second subset of nucleic acid molecules to produce one or more second amplified nucleic acid molecules with a second mean GC content, and (iv) the first mean GC content of the first subset of nucleic acid molecules differs from the second mean GC content of the second subset of nucleic acid molecules; and (b) producing two or more nucleic acid libraries, wherein (i) the two or more libraries comprise a first nucleic acid molecules library and second nucleic acid molecules library, (ii) the first nucleic acid molecules library comprises the one or more first amplified nucleic acid molecules, (iii) the second nucleic acid molecules library comprises the one or more second amplified nucleic acid molecules, and (iv) the content of the first nucleic acid molecules library is at least partially complementary to the content of the second nucleic acid molecules library.

Also provided herein is a method for developing complementary nucleic acid libraries, comprising (a) producing two or more subsets of nucleic acid molecules from a sample of nucleic acid molecules, wherein (i) the two or more subsets of nucleic acid molecules comprise a first subset of nucleic acid molecules and a second subset of nucleic acid molecules, and (ii) the two or more subsets of nucleic acid molecules differ by one or more features selected from genomic regions, mean GC content, mean molecular size, subset preparation method, or combination thereof; and (b) producing two or more nucleic acid libraries, wherein (i) the two or more libraries comprise a first nucleic acid molecules library and second nucleic acid molecules library, (ii) the first nucleic acid molecules library comprises the one or more nucleic acid molecules from the first subset of nucleic acid molecules, (iii) the second nucleic acid molecules library comprises the one or more nucleic acid molecules from the second subset of nucleic acid molecules, and (iv) the content of the first nucleic acid molecules library is at least partially complementary to the content of the second nucleic acid molecules library.

Disclosed herein is a method for sequencing, comprising (a) contacting a nucleic acid sample with one or more capture probe libraries to produce one or more capture probe hybridized nucleic acid molecules; and (b) conducting one or more sequencing reactions on the one or more capture probe hybridized nucleic acid molecules to produce one or more sequence reads, wherein (i) the sensitivity of the sequencing reaction is improved by at least about 4% as compared current sequencing methods; (ii) the sensitivity of the sequencing reaction for a genomic region comprising a RefSeq is at least about 85%, (iii) the sensitivity of the sequencing reaction for a genomic region comprising an interpretable genome is at least about 88%, (iv) the sensitivity of the sequencing reaction for an interpretable variant is at least about 90%, or (v) a combination of (i)-(ii).

At least one of the one or more capture probe libraries may comprise one or more capture probes to one or more genomic regions.

The methods and systems disclosed herein may further comprise conducting one or more sequencing reactions on one or more capture probe free nucleic acid molecules.

The percent error of the one or more sequencing reactions may similar to current sequencing methods. The percent error rate of the one or more sequencing reactions may be within about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 1%, 1.1%, 1.2%, 1.3%, 1.4%, 1.5%, 1.6%, 1.7%, 1.8%, 1.9%, or 2% of the current sequencing methods. The percent error of the one or more sequencing reactions is less than the error rate of current sequencing methods. The percent error of the sequencing reaction may be less than about 1.5%, 1%, 0.75%, 0.50%, 0.25%, 0.10%, 0.075%, 0.050%, 0.025%, or 0.001%.

The accuracy of the one or more sequencing reactions may similar to current sequencing methods. The accuracy of the one or more sequencing reactions is better than current sequencing methods.

The nucleic acid molecules may be DNA. The nucleic acid molecules may be RNA.

The methods and systems may comprise a second subset of nucleic acid molecules. The first subset and the second subset of nucleic acid molecules may differ by one or more features selected from genomic regions, mean GC content, mean molecular size, subset preparation method, or combination thereof.

The one or more genomic regions may be selected from the group comprising high GC content, low GC content, low complexity, low mappability, known single nucleotide variations (SNVs), known inDels, known alternative sequences, entire genome, entire exome, set of genes, set of regulatory elements, and methylation state.

The set of genes may selected from a group comprising set of genes with known Mendelian traits, set of genes with known disease traits, set of genes with known drug traits, and set of genes with known biomedically interpretable variants.

The known alternative sequences may be selected from the group comprising one or more small insertions, small deletions, structural variant junctions, variable length tandem repeats, and flanking sequences.

The subsets of nucleic acid molecules may differ by mean molecular size. The difference in mean molecular size between at least two of the subsets of nucleic acid molecules is at least 100 nucleotides. The difference in mean molecular size between at least two of the subsets of nucleic acid molecules is at least 200 nucleotides. The difference in mean molecular size between at least two of the subsets of nucleic acid molecules is at least 300 nucleotides.

The subsets of nucleic acid molecules may differ by mean GC content. The mean GC content of one or more subsets may be greater than or equal to 70%. Alternatively, the mean GC content of one or more subsets may be less than 70%.

The difference between the mean GC content of two or more subsets may be at least about 5%, 10%, 15% or more.

One or more additional assays may be conducted. A second assay may be conducted. A third assay may be conducted. A fourth assay may be conducted. A fifth, sixth, seventh, eighth, ninth, or tenth assay may be conducted. The one or more assays may comprise one or more sequencing reactions, amplification reactions, hybridization reactions, detection reaction, enrichment reactions, or a combination thereof.

The one or more assays may produce one or more results. The second assay may comprise a nucleic acid sequencing reaction that produces the second result, and wherein the second result may comprise nucleic acid sequence information for the second subset.

The first and second assays may be conducted separately. The first and second assays may be conducted sequentially. The first and second assays may be conducted simultaneously.

At least two of the subsets of nucleic acid molecules may be combined to produce a combined subset of nucleic acid molecules. The first and second assays may be conducted on the combined subset of nucleic acid molecules.

The first assay and the second assay may be the same. The first assay and the second assay may be different.

Analyzing the nucleic acid sample may comprise producing a unified assessment of the sample genetic state at each locus addressed by the assays.

Conducting one or more amplification reactions may comprise one or more PCR-based amplifications, non-PCR based amplifications, or a combination thereof. The one or more PCR-based amplifications may comprise PCR, qPCR, nested PCR, linear amplification, or a combination thereof. The one or more non-PCR based amplifications may comprise multiple displacement amplification (MDA), transcription-mediated amplification (TMA), nucleic acid sequence-based amplification (NASBA), strand displacement amplification (SDA), real-time SDA, rolling circle amplification, circle-to-circle amplification or a combination thereof.

The sequencing reactions may comprise capillary sequencing, next generation sequencing, Sanger sequencing, sequencing by synthesis, single molecule nanopore sequencing, sequencing by ligation, sequencing by hybridization, sequencing by nanopore current restriction, or a combination thereof. Sequencing by synthesis may comprise reversible terminator sequencing, processive single molecule sequencing, sequential nucleotide flow sequencing, or a combination thereof. Sequential nucleotide flow sequencing may comprise pyrosequencing, pH-mediated sequencing, semiconductor sequencing or a combination thereof conducting one or more sequencing reactions comprises whole genome sequencing or exome sequencing.

The sequencing reactions may comprise one or more capture probes or libraries of capture probes. At least one of the one or more capture probe libraries may comprise one or more capture probes to 1, 2, 3, 4, 5, 6, 7, 8, 9, 10, 11, 12, 13, 14, 15 or more genomic regions. The libraries of capture probes may be at least partially complementary. The libraries of capture probes may be fully complementary. The libraries of capture probes may be at least about 5%, 10%, 15%, 20%, %, 25%, 30%, 35%, 40%, 45%, 50%, 55%, 60%, 70%, 80%, 90%, 95%, 97% or more complementary.

The methods and systems disclosed herein may further comprise conducting one or more sequencing reactions on one or more capture probe free nucleic acid molecules. The methods and systems disclosed herein may further comprise conducting one or more sequencing reactions on one or more subsets on nucleic acid molecules comprising one or more capture probe free nucleic acid molecules.

The methods and systems disclosed herein may increase the sensitivity of one or more sequencing reactions when compared to the sensitivity of current sequencing methods. The sensitivity of the one or more sequencing reactions may increase by at least about 1%, 2%, 3%, 4%, 5%, 5.5%, 6%, 6.5%, 7%, 7.5%, 8%, 8.5%, 9%, 9.5%, 10%, 10.5%, 11%, 12%, 13%, 14%, 15%, 16%, 17%, 18%, 19%, 20%, 25%, 30%, 35%, 40%, 45%, 50%, 55%, 60%, 70%, 80%, 90%, 95%, 97% or more. The sensitivity of the one or more sequencing reactions may increase by at least about 4.5-20%, about 5-15%, about 7%-12%, or about 8%-10%.

The percent error of the one or more sequencing reactions may similar to current sequencing methods. The percent error rate of the one or more sequencing reactions may be within about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 1%, 1.1%, 1.2%, 1.3%, 1.4%, 1.5%, 1.6%, 1.7%, 1.8%, 1.9%, or 2% of the current sequencing methods. The percent error rate of the one or more sequencing reactions may be less than the percent error rate of current sequencing methods. The percent error rate of the one or more sequencing reactions may be at least about 10%, 9,%, 8%, 7%, 6%, 5%, 4%, 3%, 2%, 1.75%, 1.5%, 1.25%, 1%, 0.9%, 0.8%, 0.7%, 0.6%, 0.5%, 0.4%, 0.3%, 0.2%, 0.1% less than the percent error rate of current sequencing methods. The percent error rate of the sequencing reaction may be less than about 2%, 1.75%, 1.5%, 1.25%, 1%, 0.75%, 0.50%, 0.25%, 0.10%, 0.075%, 0.050%, 0.025%, or 0.001%.

The error of the sequencing reactions can be determined as a Phred quality score. The Phred quality score may be assigned to each base call in automated sequencer traces and may be used to compare the efficacy of different sequencing methods. The Phred quality score (Q) may be defined as a property which is logarithmically related to the base-calling error probabilities (P). The Phred quality score (Q) may be calculated as $Q=-10 \log_{10} P$. The Phred quality score of the one or more sequencing reactions may be similar to the Phred quality score of current sequencing methods. The Phred quality score of the one or more sequencing methods may be within 1, 2, 3, 4, 5, 6, 7, 8, 9, 10 of the Phred quality score of the current sequencing methods. The Phred quality score of the one or more sequencing methods may be less than the Phred quality score of the one or more sequencing methods. The Phred quality score of the one or more sequencing methods may be at least about 10, 9, 8, 7, 6, 5, 4, 3, 2, 1 less than the Phred quality score of the one or more sequencing methods. The Phred quality score of the one or more sequencing methods may be greater than 5, 6, 7, 8, 9, 10, 11, 12, 13, 14, 15, 16, 17, 18, 19, 20, 25, or 30. The Phred quality score of the one or more sequencing methods may be greater than 35, 40, 41, 42, 43, 44, 45, 46, 47, 48, 49, 50, 51, 52, 53, 54, 55, 56, 57, 58, 59, or 60. The Phred quality score of the one or more sequencing methods may be at least 35, 36, 37, 38, 39, 40, 41, 42, 43, 44, 45, 46, 47, 48, 49, 50, 51, 52, 53, 54, 55, 56, 57, 58, 59, 60 or more.

The accuracy of the one or more sequencing reactions may be similar to current sequencing methods. The accuracy of the one or more sequencing reactions may be within about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 1%, 1.1%, 1.2%, 1.3%, 1.4%, 1.5%, 1.6%, 1.7%, 1.8%, 1.9%, 20%, 2.25%, 2.5%, 2.75%, 3%, 3.25%, 3.5%, 3.75%, or 4% of the current sequencing methods. The accuracy of the one or more sequencing reactions may be greater than the accuracy of current sequencing methods. The accuracy of the one or more sequencing reactions may be at least about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 1%, 1.1%, 1.2%, 1.3%, 1.4%, 1.5%, 1.6%, 1.7%, 1.8%, 1.9%, 2%, 2.25%, 2.5%, 2.75%, 3%, 3.25%, 3.5%, 3.75%, 4%, 4.5%, 5%, 6%, 7%, 8%, 9%, 10%, 11%, 12%, 15%, 17%, 20%, 25%, 30%, 35%, 40%, 50%, or 60% greater than the accuracy of current sequencing methods. The accuracy of the sequencing reaction may be greater than about 70%, 75%, 80%, 85%, 90%, 91%, 92%, 93%, 94%, 95%, 96%, 97%, 98.25%, 98.5%, 98.75%, 99%, 99.25%, 99.5%, or 99.75%. The accuracy of the sequencing reaction may be greater than about 99.1%, 99.2%, 99.3%, 99.4%, 99.5%, 99.6%, 99.7%, 99.8%, 99.9%, 99.99%, or 90.999%.

Conducting a detection reaction may comprise optical sensing, electrical sensing, pH sensing, or a combination thereof. Optical sensing may comprise optical sensing of a photoluminescence photon emission, fluorescence photon emission, pyrophosphate photon emission, chemiluminescence photon emission, or a combination thereof. Electrical sensing may comprise electrical sensing of an ion concentration, ion current modulation, nucleotide electrical fields, nucleotide tunneling current, or a combination thereof.

Producing the subsets of nucleic acid molecules may comprise conducting an enrichment reaction.

Conducting an enrichment reaction may comprise conducting one or more hybridization reactions. Conducting an enrichment reaction may comprise differential amplification of two or more subsets based on one or more genomic region features.

One or more hybridization reactions may comprise one or more hybridization arrays, hybridization reactions, hybridization chain reactions, isothermal hybridization reactions, nucleic acid hybridization reactions, or a combination thereof. One or more hybridization arrays may comprise hybridization array genotyping, hybridization array proportional sensing, DNA hybridization arrays, macroarrays, microarrays, high-density oligonucleotide arrays, genomic hybridization arrays, comparative hybridization arrays, or a combination thereof one or more hybridization reactions may comprise a first hybridization reaction on the first subset of nucleic acid molecules to produce one or more first hybridized nucleic acid molecules, conducting a second hybridization reaction on the second subset of nucleic acid molecules to produce one or more second hybridized nucleic acid molecules, or a combination thereof.

One or more hybridization reactions may comprise one or more sets of capture probes. One or more hybridization reactions may comprise (a) a first subset of nucleic acid molecules comprising one or more capture probe hybridized nucleic acid molecules; and (b) a second subset of nucleic acid molecules comprising one or more capture probe free nucleic acid molecules.

One or more or more hybridization reactions may comprise one or more sets of beads. One or more or more sets of beads may comprise (a) a first subset of nucleic acid molecules comprising one or more bead bound nucleic acid molecules; and (b) a second subset of nucleic acid molecules comprising one or more bead free nucleic acid molecules.

The methods and systems disclosed herein may further comprise combining the results from two or more assays. The methods and systems disclosed herein may further comprise combining the subsets of nucleic acid molecules after producing two or more subsets of nucleic acid molecules to produce one or more combined subsets of nucleic acid molecules. The methods and systems disclosed herein may further comprise combining the subsets of nucleic acid molecules prior to conducting one or more assays to produce one or more combined subsets of nucleic acid molecules. Combining the results may comprise combining two or more sequencing data sets by means of a precedence rule utilizing one or more of genomic contexts and/or assay technology to resolve discordances between two or more sequencing data sets. Combining the results may comprise combining two or variant call sets by means of a statistical algorithm utilizing one or more of quality and read coverage metrics to resolve one or more discordant genotypes. Combining the results may comprise combining two or more assay read data sets by means of a statistical algorithm utilizing one or more of base read quality and allele frequency to compute a consensus call at one or more applicable loci.

At least two of the subsets of nucleic acid molecules may be fluidically separated. At least two of the subsets of nucleic acid molecules may be separated into two or more different containers. The two or more different containers may comprise plates, microplates, PCR plates, wells, microwells, tubes, Eppendorf tubes, vials, arrays, microarrays, chips or a combination thereof.

The methods and systems disclosed herein may further comprise producing one or more outputs based on the analysis of the nucleic acid sample. The one or more outputs may comprise one or more biomedical reports. The one or more biomedical reports may comprise biomedical information of a subject. The biomedical information of the subject predicts, prognoses, or diagnoses one or more biomedical features selected from the group, comprising disease state, genetic risk of a disease, reproductive risk, genetic risk to a fetus, risk of an adverse drug reaction, efficacy of a drug therapy, prediction of optimal drug dosage, transplant tolerance, or a combination thereof.

The methods and systems disclosed herein may further comprise aggregating information from two or more databases. The methods and systems disclosed herein may further comprise combining information from two or more databases. The databases may comprise biomedical or scientific information. The information may comprise information on one or more polymorphisms, diseases or conditions, genetic diseases, genes, exomes, genomes, or a combination thereof.

The one or more polymorphisms may comprise one or more insertions, deletions, structural variant junctions, variable length tandem repeats, single nucleotide mutations, or a combination thereof.

The analysis of one or more nucleic sample of (a) and/or the analysis of one or more nucleic sample of (c) may comprise generating data or results based on or derived from the analysis of two or more subsets of nucleic acid molecules.

Disclosed herein is a system comprising (a) first computer processor for producing a first biomedical report, wherein (i) the first biomedical report is generated from data or results based on the analysis of two or more subsets of nucleic acid molecules from a nucleic acid sample, and (ii) the two or more subsets of nucleic acid molecules differ by one or more features; (b) a second computer processor for transmitting the first biomedical report to a user; (c) a third computer processor for producing a second biomedical report, wherein (i) the second biomedical report is generated from the data or results based on the analysis of two or more subsets of nucleic acid molecules from the nucleic acid sample, (ii) the two or more subsets of nucleic acid molecules differ by one or more features, and (iii) the first biomedical report and the second biomedical report differ by one or more biomedical features; and (d) a fourth computer processor for transmitting the second biomedical report to the user.

Disclosed herein is a system comprising (a) first computer processor for producing a first biomedical report, wherein the first biomedical report is generated from data or results based on the analysis of one or more nucleic acid samples; (b) a second computer processor for transmitting the first biomedical report to a user; (c) a third computer processor for producing a second biomedical report, wherein (i) the second biomedical report is based on or derived from the first biomedical report, (ii) the second biomedical report is generated from data or results based on the analysis of one or more nucleic acid samples, or (iii) a combination of (i)-(ii); and (d) a fourth computer processor for transmitting the second biomedical report to the user. Analysis of one or more nucleic sample of (a) and/or the analysis of one or more nucleic sample of (c) may comprise generating data or results based on or derived from the analysis of two or more subsets of nucleic acid molecules. Transmitting the second biomedical report is based on the analysis of the first biomedical report.

Further disclosed herein is a system comprising (a) a first computer processor for producing a first biomedical report, wherein the first biomedical report is generated from data or results based on the analysis of one or more nucleic acid samples; (b) a second computer processor for analyzing the first biomedical report; and (c) a third computer processor for transmitting a second biomedical report, wherein (i) the second biomedical report is based on or derived from the first biomedical report, (ii) the second biomedical report is generated from data or results based on the analysis of one or more nucleic acid samples, or (iii) a combination of (i)-(ii). Analysis of one or more nucleic sample of (a) and/or the analysis of one or more nucleic sample of (c) may comprise generating data or results based on or derived from the analysis of two or more subsets of nucleic acid molecules.

Disclosed herein is a method for generating a biomedical report, comprising (a) receiving, from a user, a first request for a first biomedical report, wherein (i) the first biomedical report is generated from data or results based on the analysis of two or more subsets of nucleic acid molecules from a nucleic acid sample, and (ii) the two or more subsets of nucleic acid molecules differ by one or more features selected from genomic regions, mean GC content, mean molecular size, subset preparation method, or combination thereof; (b) transmitting the first biomedical report to the user; (c) receiving, from the user, a second request for a second biomedical report, wherein (i) the second biomedical report is generated from the data or results based on the analysis of two or more subsets of nucleic acid molecules from the nucleic acid sample, (ii) the two or more subsets of nucleic acid molecules differ by one or more features, and (iii) the first biomedical report and the second biomedical report differ by one or more biomedical features; and (c) transmitting the second biomedical report to the user.

Disclosed herein is a method for generating a biomedical report, comprising (a) receiving, from a user, a first request for a first biomedical report, wherein the first biomedical report is generated from data or results based on the analysis of one or more nucleic acid samples; (b) transmitting the first biomedical report to the user; (c) receiving, from the user, a second request for a second biomedical report differing from the first biomedical report, wherein (i) the second biomedical report is based on or derived from the first biomedical report, (ii) the second biomedical report is generated from data or results based on the analysis of one or more nucleic acid samples, or (iii) a combination of (i)-(ii); and transmitting the second biomedical report to the user. The analysis of one or more nucleic sample of (a) and/or the analysis of one or more nucleic sample of (c) may comprise generating data or results based on or derived from the analysis of two or more subsets of nucleic acid molecules. Transmitting the second biomedical report may be based on the analysis of the first biomedical report.

Further disclosed herein is a method for generating one or more biomedical reports, comprising (a) receiving, from a user, a first request for a first biomedical report, wherein the first biomedical report is generated from data or results based on the analysis of one or more nucleic acid samples; (b) analyzing, with the aid of a processor, one or more results from the first biomedical report; (c) transmitting a second biomedical report to the user, wherein (i) the second biomedical report is based on or derived from the first biomedical report, (ii) the second biomedical report is generated from data or results based on the analysis of one or more nucleic acid samples, or (iii) a combination of (i)-(ii). The analysis of one or more nucleic sample of (a) and/or the analysis of one or more nucleic sample of (c) may comprise generating data or results based on or derived from the analysis of two or more subsets of nucleic acid molecules.

The data or results of (a) and the data or results of (c) may be the same. The data or results of (a) and the data or results of (c) may be similar. The data or results of (a) and the data or results of (c) may be different. The data or results of (a) and the data or results of (c) may be derived from or based on one or more assays. The data or results of (a) and the data or results of (c) may be derived from or based on the same assay. The data or results of (a) and the data or results of (c) may be derived from or based on the similar assays. The data or results of (a) and the data or results of (c) may be derived from or based on two or more different assays. The data or results of (a) and the data or results of (c) may be from one or more combined data or combined results. The data or results of (a) and the data or results of (c) may be from the same combined data or combined results. The data or results of (a) and the data or results of (c) may be from similar combined data or combined results. The data or results of (a) and the data or results of (c) may be from different combined data or combined results.

The methods and systems disclosed herein may further comprise one or more memory locations to receive one or more requests from a user, store one or more requests from a user, store the biomedical reports, or a combination thereof.

The methods and systems disclosed herein may further comprise one or more additional processors for aggregating information from two or more databases. The methods and systems disclosed herein may further comprise one or more additional processors for generating one or more database libraries. The database libraries may comprise data or results from one or more subsets of nucleic acid molecules. The database libraries may comprise information at least a portion of two or more databases.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention(s) are set forth with particularity in the appended claims. A better understanding of the features and advantages of the present invention(s) will be obtained by reference to the following detailed description that sets forth illustrative embodiments, in which the principles of the invention(s) are utilized, and the accompanying drawings (also "FIG." and "FIGS." herein), of which:

FIG. 2A depicts an assay and analysis workflow comprising purification of DNA from a sample by two purification methods to produce two subsets of purified DNA (Prep 1 and Prep 2). The two subsets of purified DNA are combined and a single assay is conducted on the combined subsets. Lastly, a single analysis of the assay results is conducted and an output is generated. FIG. 2B depicts an assay and analysis workflow comprising purification of DNA from a sample by two purification methods to produce two subsets of purified DNA (Prep 1 and Prep 2). An assay is conducted on each subset. A single analysis of the results of the two assays (Assay 1 and Assay 2) is conducted and an output is generated. FIG. 2C depicts an assay and analysis workflow comprising purification of DNA from a sample by two purification methods to produce two subsets of purified DNA (Prep 1 and Prep 2). An assay (Assay 1 and Assay 2) is conducted on each subset (Prep 1 and Prep 2). An analysis (Analysis 1 and Analysis 2) is conducted on results from each assay. A single output is generated based on the two separate analyses. FIG. 2D depicts an assay and analysis workflow comprising (1) separation of the nucleic acid sample into several subsets processed with several protocols. These protocols may involve enrichment for different genomic or non-genomic regions and comprise one or more different amplification steps to prepare libraries of nucleic acid molecules for assay. Some of these libraries may combined (2) for assay. Results of some assays may be combined (3) for subsequent analysis. Variant calls or other assessments of sequence or genetic state may be further combined (4) to produce a combined assessment at each locus addressed by the assay.

DETAILED DESCRIPTION

Figure 1:
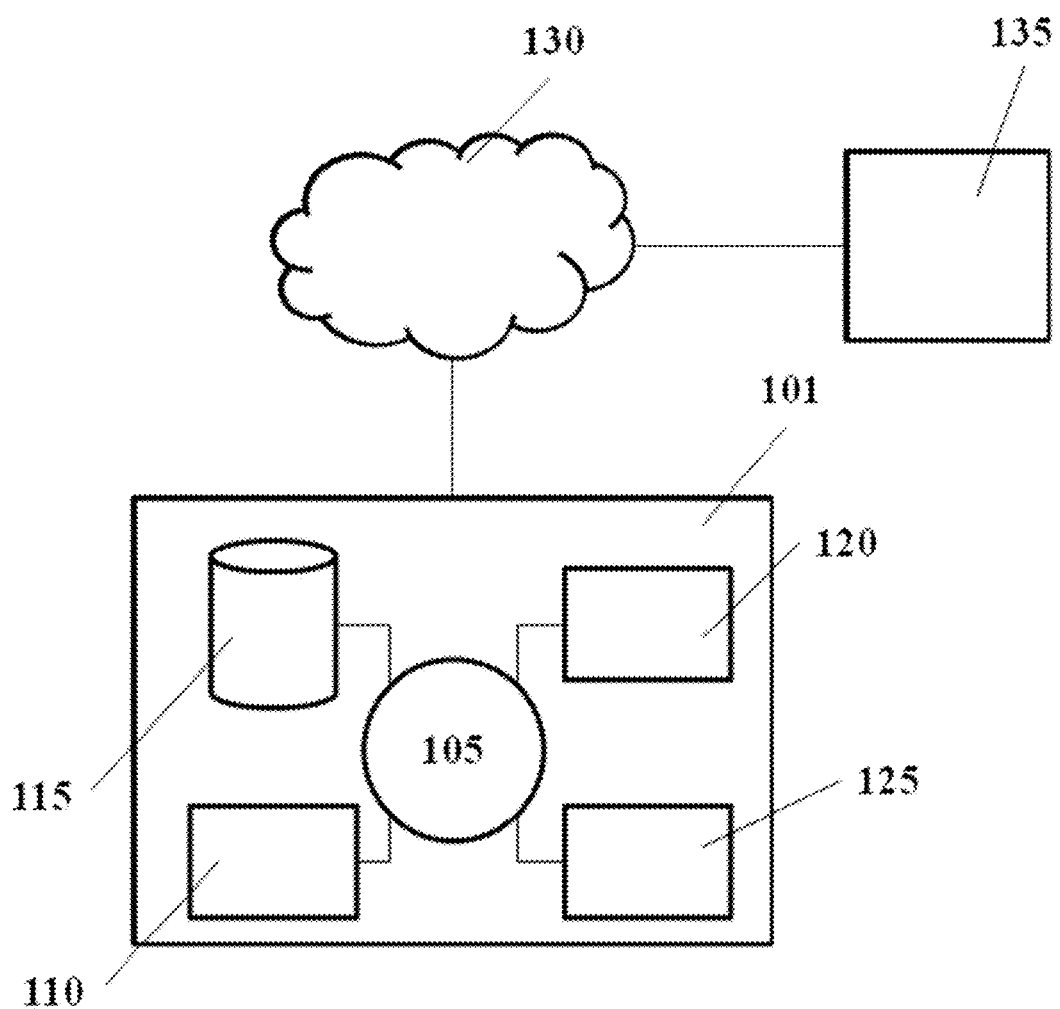
FIG. 1. shows a system for implementing the methods of the disclosure.
Figure 2:
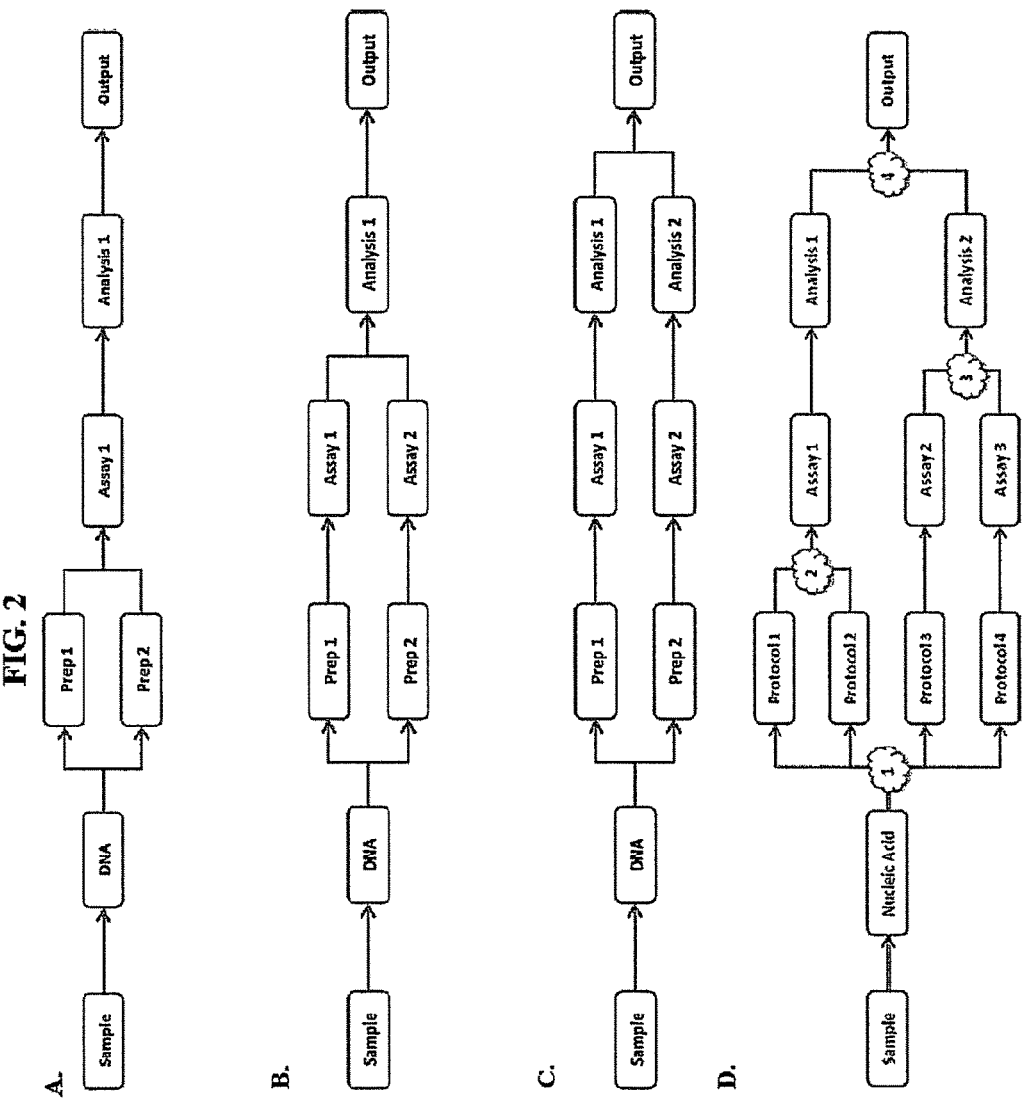
FIGS. 2A-2D depict a schematic of four exemplary workflows of the present disclosure. The terms "Prep 1" and "Prep 2" may refer to subsets of nucleic acid molecules; "Assay 1" and "Assay 2" may refer to assays.
Figure 3:
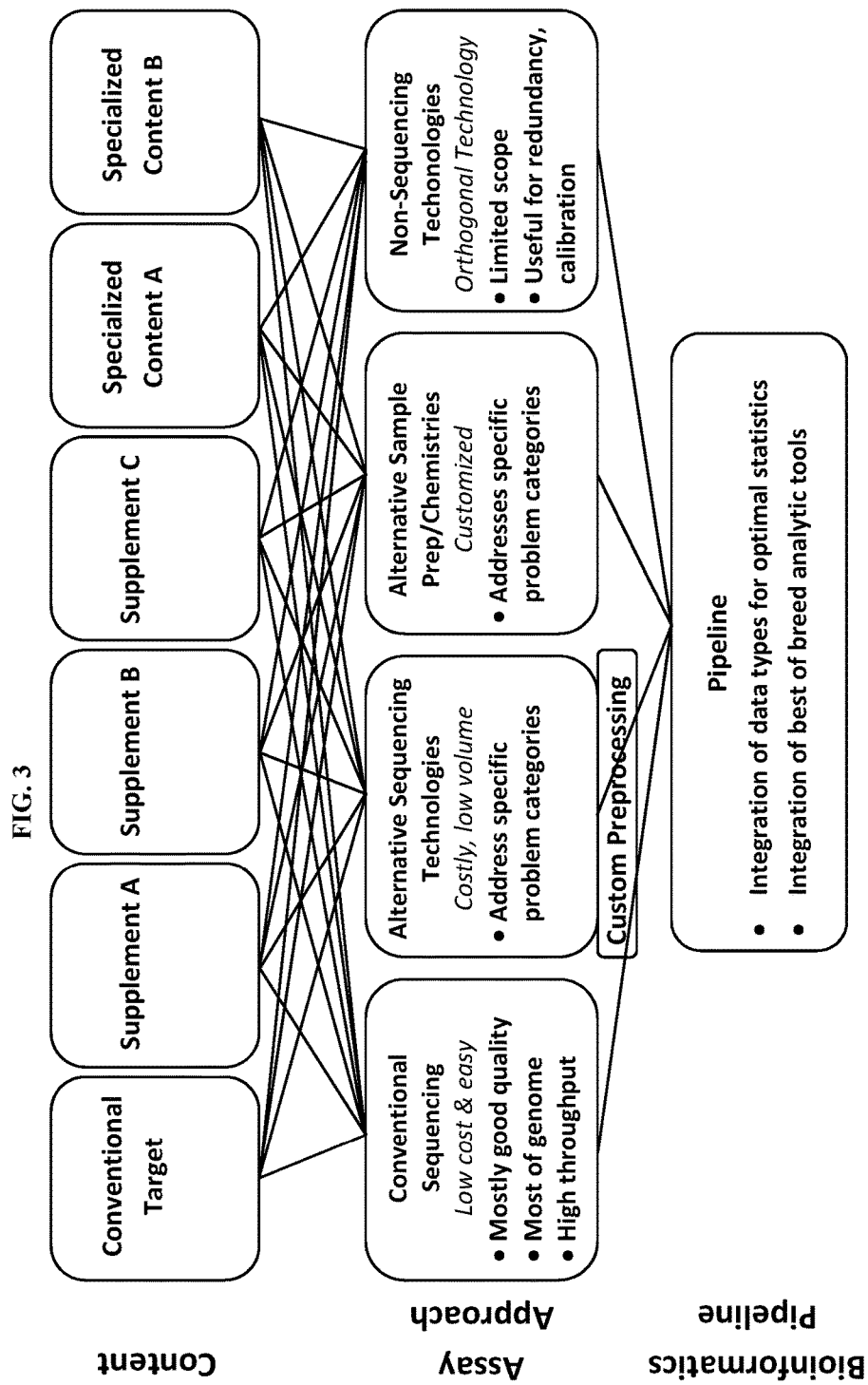
FIG. 3. depicts a schematic of a workflow of the present disclosure.
Figure 4:
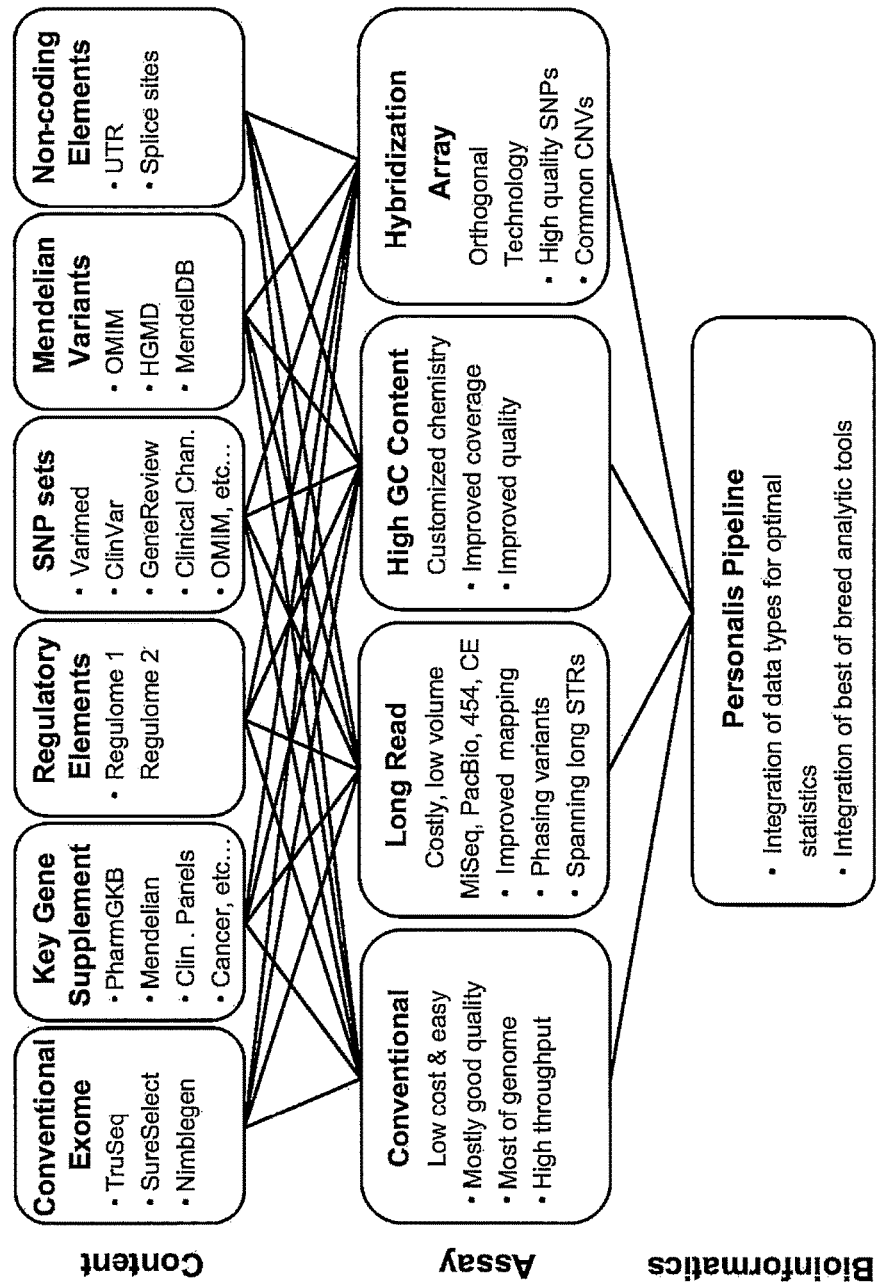
FIG. 4. depicts a schematic of a workflow of the present disclosure.

While various embodiments of the invention(s) of the present disclosure have been shown and described herein, it will be obvious to those skilled in the art that such embodiments are provided by way of example only. Numerous variations, changes, and substitutions may occur to those skilled in the art without departing from the invention(s). It should be understood that various alternatives to the embodiments of the invention(s) described herein may be employed in practicing any one of the inventions(s) set forth herein.

This disclosure provides systems and methods for sample processing and data analysis. In some cases, sample processing includes nucleic acid sample processing and subsequent nucleic acid sample sequencing. Some or all of a nucleic acid sample may be sequenced to provide sequence information, which may be stored or otherwise maintained in an electronic, magnetic or optical storage location. The sequence information may be analyzed with the aid of a computer processor, and the analyzed sequence information may be stored in an electronic storage location. The electronic storage location may include a pool or collection of sequence information and analyzed sequence information generated from the nucleic acid sample. The nucleic acid sample may be retrieved from a subject, such as, for example, a subject receiving therapy.

In some cases, a user, such as a healthcare provider, may request a first set of sequence information or analyzed sequence information from the pool. Concurrently or subsequently, the user may request a second set of sequence information or analyzed sequence information from the pool. The first set may be different from the second set.

The term "nucleic acid" as used herein generally refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired. The nucleic acid molecule may be a DNA molecule. The nucleic acid molecule may be an RNA molecule.

As used herein, the terms "variant or derivative of a nucleic acid molecule" or "derivative or variant of a nucleic acid molecule" generally refer to a nucleic acid molecule comprising a polymorphism. The terms "variant or derivative of a nucleic acid molecule" or "derivative or variant of a nucleic acid molecule" may also refer to nucleic acid product that is produced from one or more assays conducted on the nucleic acid molecule. For example, a fragmented nucleic acid molecule, hybridized nucleic acid molecule (e.g., capture probe hybridized nucleic acid molecule, bead bound nucleic acid molecule), amplified nucleic acid molecule, isolated nucleic acid molecule, eluted nucleic acid molecule, and enriched nucleic acid molecule are variants or derivatives of the nucleic acid molecule.

The terms "detectable label" or "label" as used herein generally refers to any chemical moiety attached to a nucleotide, nucleotide polymer, or nucleic acid binding factor, wherein the attachment may be covalent or non-covalent. Preferably, the label is detectable and renders the nucleotide or nucleotide polymer detectable to the practitioner of the invention. The terms "detectable label" or "label" may be used interchangeably. Detectable labels that may be used in combination with the methods disclosed herein include, for example, a fluorescent label, a chemiluminescent label, a quencher, a radioactive label, biotin, quantum dot, gold, or a combination thereof. Detectable labels include luminescent molecules, fluorochromes, fluorescent quenching agents, colored molecules, radioisotopes or scintillants. Detectable labels also include any useful linker molecule (such as biotin, avidin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase and luciferase), electron donors/acceptors, acridinium esters, dyes and calorimetric substrates. It is also envisioned that a change in mass may be considered a detectable label, as is the case of surface plasmon resonance detection. The skilled artisan would readily recognize useful detectable labels that are not mentioned above, which may be employed in the operation of the present invention.

The terms "bound", "hybridized", "conjugated", "attached", "linked" can be used interchangeably and generally refer to the association of a object to another object. The association of the two objects to each other may be from a covalent or non-covalent interaction. For example, a capture probe hybridized nucleic acid molecule refers a capture probe associated with a nucleic acid molecule. The capture probe and the nucleic acid molecule are in contact with each other. In another example, a bead bound nucleic acid molecule refers to a bead associated with a nucleic acid molecule.

Disclosed herein are methods for analyzing a nucleic acid sample. The methods of the disclosure may comprise (a) producing two or more subsets of nucleic acid molecules from a nucleic acid sample comprising one or more nucleic acid molecules; (b) enriching the two or more subsets of nucleic acid molecules for two or more different subsets of a genomic region; (c) conducting an assay on each of the two subsets of nucleic acid molecules, wherein (i) a first assay, comprising a first sequencing reaction, is conducted on the first subset of the two or more subsets of nucleic acid molecules to produce a first result, and (ii) a second assay is conducted on the second subset of the two or more subsets to produce a second result; and (d) combining, with the aid of a computer processor, the first result and the second result, thereby analyzing the nucleic acid sample.

In an aspect of the present disclosure, methods for nucleic acid processing and/or analysis are provided. The methods disclosed herein may comprise (a) producing two or more subsets of nucleic acid molecules from a nucleic acid sample; (b) combining at least two of the two or more subsets of nucleic acid molecules to produce a combined pool of nucleic acid molecules; and (c) conducting one or more assays on the combined pool of nucleic acid molecules, wherein at least one of the one or more assays comprises a sequencing reaction.

Provided herein are methods comprising (a) producing two or more subsets of nucleic acid molecules from a nucleic acid sample; (b) enriching the two or more subsets of nucleic acid molecules for two or more different subsets of a genomic region; (c) conducting a first assay on a first subset of nucleic acid molecules among the two or more subsets of nucleic acid molecules to produce a first result, wherein the first assay comprises a first sequencing reaction; (d) conducting a second assay on at least a second subset of nucleic acid molecules among the two or more subsets of nucleic acid molecules to produce a second result; and (e) combining, with the aid of a computer processor, the first result with the second result, thereby analyzing the nucleic acid sample.

Also disclosed herein are methods comprising (a) preparing at least a first subset of nucleic acid molecules and a second subset of nucleic acid molecules from a nucleic acid sample; (b) enriching the first and second subsets of nucleic acid molecules for at least two subsets of a genomic region; (c) conducting a first assay on the first subset of nucleic acid molecules and a second assay on the second subset of nucleic acid molecules, wherein the first assay comprises a nucleic acid sequencing reaction that produces a first result, comprising nucleic acid sequence information for the first subset, and wherein the second assay produces a second result; (d) analyzing, with the aid of a computer processor, the first result to provide a first analyzed result and analyzing the second result to provide a second analyzed result; and (e) combining, with the aid of a computer processor, the first and second analyzed results, thereby analyzing the nucleic acid sample.

Disclosed herein are methods, comprising (a) conducting a first assay on a nucleic acid sample, wherein the first assay comprises one or more antioxidants; and (b) conducting a sequencing reaction on the nucleic acid sample, thereby analyzing the nucleic acid sample.

Further provided herein are methods comprising (a) producing, with the aid of a computer processor, one or more capture probes, wherein the one or more capture probes hybridize to one or more polymorphisms; (b) contacting a nucleic acid sample with the one or more capture probes to produce one or more capture probe hybridized nucleic acid molecules; and (c) conducting a sequencing reaction on the one or more capture probe hybridized nucleic acid molecules, thereby analyzing the nucleic acid sample.

Further disclosed herein are methods for analyzing a nucleic acid molecule. The methods may comprise (a) contacting a nucleic acid sample with one or more capture probes, wherein at least one of the one or more capture probes hybridize to a structural variant within, near or spanning an entire gene or at least a portion of a gene of to produce one or more capture probe hybridized nucleic acid molecules; and (b) conducting a sequencing reaction on the one or more capture probe hybridized nucleic acid molecules, thereby analyzing the gene. The one or more capture probes may additionally hybridize to one or more genomic regions disclosed herein.

Provided herein are methods comprising (a) conducting a first assay on a nucleic acid sample, wherein the first assay comprises fragmenting one or more nucleic acid molecules in the nucleic acid sample to produce one or more first fragmented nucleic acid molecules; (b) conducting a second assay on the nucleic acid sample, wherein the second assay comprises contacting at least a portion of the one or more first fragmented nucleic acid molecules with a first set of beads to produce a one or more first bead bound nucleic acid molecules; and (c) conducting a third assay on the nucleic acid sample, wherein the third assay comprises contacting at least a portion of the first fragmented nucleic acid molecules with a second set of beads to produce one or more second bead bound nucleic acid molecules, thereby preparing the nucleic acid sample.

Disclosed herein are methods comprising (a) producing two or more subsets of nucleic acid molecules from a sample, wherein (i) the two or more subsets of nucleic acid molecules comprise a first subset of nucleic acid molecules and a second subset of nucleic acid molecules, (ii) the first subset of nucleic acid molecules comprises nucleic acid molecules of a first mean size, (iii) the second subset of nucleic acid molecules comprises nucleic acid molecules of a second mean size, and (iv) the first mean size of the first subset of nucleic acid molecules is greater than the second mean size of the second subset of nucleic acid molecules by about 200 or more residues; and (b) producing two or more nucleic acid libraries, wherein (i) the two or more libraries comprise a first nucleic acid library and second nucleic acid library, (ii) the first nucleic acid library comprises the one or more first bead bound nucleic acid molecules, (iii) the second nucleic acid library comprises the one or more second bead bound nucleic acid molecules, and (iv) the content of the first nucleic acid library is at least partially complementary to the content of the second nucleic acid library.

Disclosed herein are methods comprising (a) producing two or more subsets of nucleic acid molecules from a sample comprising one or more nucleic acid molecules, wherein the two or more subsets of nucleic acid molecules comprise a first subset of nucleic acid molecules and a second subset of nucleic acid molecules; (b) conducting two or more assays on the two or more subsets of nucleic acid molecules, wherein (i) the two or more assays comprise a first assay and a second assay, (ii) the first assay comprises conducting a first amplification reaction on the first subset of nucleic acid molecules to produce one or more first amplicons with a first mean GC content, (iii) the second assay comprises conducting a second amplification reaction on the second subset of nucleic acid molecules to produce one or more second amplicons with a second mean GC content, and (iv) the first mean GC content of the first subset of nucleic acid molecules differs from the second mean GC content of the second subset of nucleic acid molecules; and producing two or more nucleic acid libraries, wherein (i) the two or more libraries comprise a first nucleic acid library and second nucleic acid library, (ii) the first nucleic acid library comprises the one or more first amplicons, (iii) the second nucleic acid library comprises the one or more second amplicons, and (iv) the content of the first nucleic acid library is at least partially complementary to the content of the second nucleic acid library.

Provided herein are methods comprising (a) producing two or more subsets of nucleic acid molecules from a sample comprising one or more nucleic acid molecules, wherein (i) the two or more subsets of nucleic acid molecules comprise a first subset of nucleic acid molecules and a second subset of nucleic acid molecules, and (ii) the two or more subsets of nucleic acid molecules differ by one or more genomic region features; and (b) producing two or more nucleic acid libraries, wherein (i) the two or more libraries comprise a first nucleic acid library and second nucleic acid library, (ii) the first nucleic acid library comprises the one or more first bead bound nucleic acid molecules, (iii) the second nucleic acid library comprises the one or more second bead bound nucleic acid molecules, and (iv) the content of the first nucleic acid library is at least partially complementary to the content of the second nucleic acid library.

Further provided herein are methods for sequencing a nucleic acid molecule. The methods may comprise (a) contacting a nucleic acid sample with two or more capture probe sets to produce a plurality of capture probe hybridized nucleic acid molecules, wherein the plurality of capture probe hybridized nucleic acid molecules comprise to two or more nucleic acid molecules regions selected from the group comprising (i) high GC content; (ii) low GC content; (iii) low complexity; (iv) low mappability; (v) known single nucleotide variations (SNVs); (vi) known inDels; (vii) known alternative sequences comprising one or more small insertions, small deletions, structural variant junctions, variable length tandem repeats, or flanking sequences; (viii) entire genome; (ix) entire exome; (x) set of genes with known Mendelian traits; (xi) set of genes; (xii) a set of regulatory elements; (xiii) set of genes with known disease traits; (xiv) set of genes with known drug traits; and (xv) set of genes with known biomedically interpretable variants; and (b) conducting a sequencing reaction on the plurality of capture probe hybridized nucleic acid molecules.

In some aspects of the disclosure, The methods comprise (a) contacting a nucleic acid sample with one or more capture probes, wherein at least one of the one or more capture probes hybridize to two or more different genomic regions within, near or spanning the gene of interest to produce one or more capture probe hybridized nucleic acid molecules; and (b) conducting a sequencing reaction on the one or more capture probe hybridized nucleic acid molecules, thereby analyzing the gene of interest.

Further disclosed herein, in some aspects of the disclosure, are methods for generating a biomedical report. The methods may comprise (a) receiving, from a user, a first request for a first specified biomedical report, wherein (i) the first specified heath report is generated from data or results based on the analysis of two or more subsets of nucleic acid molecules from a nucleic acid sample, and (ii) the two or more subsets of nucleic acid molecules differ by one or more features; (b) transmitting the first specified biomedical report to the user; (c) receiving, from the user, a second request for a second specified biomedical report, wherein (i) the second specified heath report is generated from the data or results based on the analysis of two or more subsets of nucleic acid molecules from the nucleic acid sample, (ii) the two or more subsets of nucleic acid molecules differ by one or more features, and (iii) the first specified biomedical report and the second specified biomedical report differ by one or more biomedical features; and (c0 transmitting the second specified biomedical report to the user.

Further disclosed herein, in some aspects of the disclosure, are complementary nucleic acid libraries, wherein the libraries are complementary in one or more aspects. The one or more aspects may be selected from the group comprising GC content, fragment length, and genomic region. Also disclosed herein are methods and systems for developing these libraries and kits comprising these libraries.

Provided herein, in some aspects of the disclosure, are kits comprising one or more capture probe sets. The kits may comprise a first capture probe set and a second capture probe set, wherein (i) the first and second capture probe sets hybridize to one or more genomic regions and (ii) one or more of the genomic regions hybridized by the first capture probe set are different from one or more of the genomic regions hybridized by the second capture probe set.

Before the present methods are described in further detail, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims. Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The disclosures herein merely illustrate the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, e.g., any elements developed that perform the same function, regardless of structure. The scope of the present invention, therefore, is not intended to be limited to the exemplary embodiments shown and described herein. Rather, the scope and spirit of the present invention is embodied by the appended claims.

Subsets of Nucleic Acid Molecules

The methods disclosed herein may comprise one or more subsets of nucleic acid molecules. The subsets of nucleic acid molecules may be derived from a nucleic acid sample. The subsets of nucleic acid molecules may be derived from the same nucleic acid sample. Alternatively, or additionally, the subsets of nucleic acid molecules are derived from two or more different nucleic acid samples. Two or more subsets of nucleic acid molecules may be differentiated by their nucleic acid content. The one or more subsets of nucleic acid molecules may comprise one or more nucleic acid molecules or a variant or derivative thereof. For example, the two or more subsets of nucleic acid molecules may comprise nucleic acids comprising different GC content, nucleic acid size, genomic regions, genomic region features, eluted nucleic acid molecules, hybridized nucleic acid molecules, non-hybridized nucleic acid molecules, amplified nucleic acid molecules, non-amplified nucleic acid molecules, supernatant-derived nucleic acid molecules, eluant-derived nucleic acid molecules, labeled nucleic acid molecules, non-labeled nucleic acid molecules, capture probe hybridized nucleic acid molecules, capture probe free nucleic acid molecules, bead bound nucleic acid molecules, bead free nucleic acid molecules, or a combination thereof. The two or more subsets of nucleic acid molecules may be differentiated by GC content, nucleic acid size, genomic regions, capture probes, beads, labels, or a combination thereof.

The methods disclosed herein may comprise combining two or more subsets of nucleic acid molecules to produce a combined subset of nucleic acid molecules. The combined subsets of nucleic acid molecules may be derived from a nucleic acid sample. The combined subsets of nucleic acid molecules may be derived from the same nucleic acid sample. Alternatively, or additionally, the combined subsets of nucleic acid molecules are derived from two or more different nucleic acid samples. Two or more combined subsets of nucleic acid molecules may be differentiated by their nucleic acid content. The one or more combined subsets of nucleic acid molecules may comprise one or more nucleic acid molecules or a variant or derivative thereof. For example, the two or more combined subsets of nucleic acid molecules may comprise nucleic acids comprising different GC content, nucleic acid size, genomic regions, genomic region features, eluted nucleic acid molecules, hybridized nucleic acid molecules, non-hybridized nucleic acid molecules, amplified nucleic acid molecules, non-amplified nucleic acid molecules, supernatant-derived nucleic acid molecules, eluant-derived nucleic acid molecules, labeled nucleic acid molecules, non-labeled nucleic acid molecules, capture probe hybridized nucleic acid molecules, capture probe free nucleic acid molecules, bead bound nucleic acid molecules, bead free nucleic acid molecules, or a combination thereof. The two or more combined subsets of nucleic acid molecules may be differentiated by GC content, nucleic acid size, genomic regions, capture probes, beads, labels, or a combination thereof.

Subsets of nucleic acid molecules may comprise one or more genomic regions as disclosed herein. Subsets of nucleic acid molecules may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more genomic regions. The one or more genomic regions may be identical, similar, different, or a combination thereof.

Subsets of nucleic acid molecules may comprise one or more genomic region features as disclosed herein. Subsets of nucleic acid molecules may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more genomic region features. The one or more genomic region features may be identical, similar, different, or a combination thereof.

Subsets of nucleic acid molecules may comprise nucleic acid molecules of different sizes. The length of a nucleic acid molecule in a subset of nucleic acid molecules may be referred to as the size of the nucleic acid molecule. The average length of the nucleic acid molecules in a subset of nucleic acid molecules may be referred to as the mean size of nucleic acid molecules. As used herein, the terms "size of a nucleic acid molecule", "mean size of nucleic acid molecules", "molecular size" and "mean molecular size" may be used interchangeably. The size of a nucleic acid molecule may be used to differentiate two or more subsets of nucleic acid molecules. The difference in the mean size of nucleic acid molecules in a subset of nucleic acid molecules and the mean size of nucleic acid molecules in another subset of nucleic acid molecules may be used to differentiate the two subsets of nucleic acid molecules. The mean size of nucleic acid molecules in one subset of nucleic acid molecules may be greater than the mean size of nucleic acid molecules in at least one other subset of nucleic acid molecules. The mean size of nucleic acid molecules in one subset of nucleic acid molecules may be less than the mean size of nucleic acid molecules in at least one other subset of nucleic acid molecules. The difference in mean molecular size between two or more subsets of nucleic acid molecules may be at least about 50; 75; 100; 125; 150; 175; 200; 225; 250; 275; 300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or base pairs. In some aspects of the disclosure, the difference in mean molecular size between two or more subsets of nucleic acid molecules is at least about 200 bases or bases pairs. Alternatively, the difference in mean molecular size between two or more subsets of nucleic acid molecules is at least about 300 bases or bases pairs.

Subsets of nucleic acid molecules may comprise nucleic acid molecules of different sequencing sizes. The length of a nucleic acid molecule in a subset of nucleic acid molecules to be sequenced may be referred to as the sequencing size of the nucleic acid molecule. The average length of the nucleic acid molecules in a subset of nucleic acid molecules may be referred to as the mean sequencing size of nucleic acid molecules. As used herein, the terms "sequencing size of a nucleic acid molecule", "mean sequencing size of nucleic acid molecules", "molecular sequencing size" and "mean molecular sequencing size" may be used interchangeably. The mean molecular sequencing size of one or more subsets of nucleic acid molecules may be at least about 50; 75; 100; 125; 150; 175; 200; 225; 250; 275; 300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or base pairs. The sequencing size of a nucleic acid molecule may be used to differentiate two or more subsets of nucleic acid molecules. The difference in the mean sequencing size of nucleic acid molecules in a subset of nucleic acid molecules and the mean sequencing size of nucleic acid molecules in another subset of nucleic acid molecules may be used to differentiate the two subsets of nucleic acid molecules. The mean sequencing size of nucleic acid molecules in one subset of nucleic acid molecules may be greater than the mean sequencing size of nucleic acid molecules in at least one other subset of nucleic acid molecules. The mean sequencing size of nucleic acid molecules in one subset of nucleic acid molecules may be less than the mean sequencing size of nucleic acid molecules in at least one other subset of nucleic acid molecules. The difference in mean molecular sequencing size between two or more subsets of nucleic acid molecules may be at least about 50; 75; 100; 125; 150; 175; 200; 225; 250; 275; 300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or base pairs. In some aspects of the disclosure, the difference in mean molecular sequencing size between two or more subsets of nucleic acid molecules is at least about 200 bases or bases pairs. Alternatively, the difference in mean molecular sequencing size between two or more subsets of nucleic acid molecules is at least about 300 bases or bases pairs.

Two or more subsets of nucleic acid molecules may be at least partially complementary. For example, a first subset of nucleic acid molecules may comprise nucleic acid molecules comprising at least a first portion of the genome and a second subset of nucleic acid molecules may comprise nucleic acid molecules comprising at least a second portion of the genome, wherein the first and second portion of the genome differ by one or more nucleic acid molecules. Thus, the first subset and the second subset are at least partially complementary. The complementarity of two or more subsets of nucleic acid molecules may be at least about 10%, 15%, 20%, 25%, 30%, 35%, 40%, 45%, 50%, 55%, 60%, 65%, 70%, 75%, 80%, 85%, 90%, 95%, 97%, or more. As used herein, the term "complementarity of two or more subsets of nucleic acid molecules" generally refers to genomic content of the two or more subsets and the extent to which the two or more subsets encompass the content of one or more genomic regions. For example, a first subset of nucleic acid molecules comprises 50% of total high GC exomes and a second subset of nucleic acid molecules comprises 50% of the total low GC exomes, then the complementarity of the two subsets of nucleic acid molecules in reference to an entire exome is 50%. In another example, a first subset of nucleic acid molecules comprises 100% of the total bead bound nucleic acid molecules and the second subset of nucleic acid molecules comprises 100% of the total bead free nucleic acid molecules, the complementarity of the two subsets in reference to the total nucleic acid molecules is 100%.

Subsets of nucleic acid molecules may comprise bead bound nucleic acid molecules. Two or more subsets of nucleic acid molecules may be differentiated into bead bound nucleic acid molecules and bead free nucleic acid molecules. For example, a first subset of nucleic acid molecules may comprise one or more bead bound nucleic acid molecules and a second subset of nucleic acid molecules may comprise bead free nucleic acid molecules. Bead free nucleic acid molecules may refer to nucleic acid molecules that are not bound to one or more beads. Bead free nucleic acid molecules may refer to nucleic acid molecules that have been eluted from one or more beads. For example, the nucleic acid molecule from a bead bound nucleic acid molecule may be eluted to produce a bead free nucleic acid molecule.

Subsets of nucleic acid molecules may comprise capture probe hybridized nucleic acid molecules. Two or more subsets of nucleic acid molecules may be differentiated into capture probe hybridized nucleic acid molecules and capture probe free nucleic acid molecules. For example, a first subset of nucleic acid molecules may comprise one or more capture probe hybridized nucleic acid molecules and a second subset of nucleic acid molecules may comprise capture probe free nucleic acid molecules. Capture probe free nucleic acid molecules may refer to nucleic acid molecules that are not hybridized to one or more capture probes. Capture probe free nucleic acid molecules may refer to nucleic acid molecules that are dehybridized from one or more capture probes. For example, the capture probe from a capture probe hybridized nucleic acid molecule may be removed to produce a capture probe free nucleic acid molecule.

Capture probes may hybridize to one or more nucleic acid molecules in a sample or in a subset of nucleic acid molecules. Capture probes may hybridize to one or more genomic regions. Capture probes may hybridize to one or more genomic regions within, around, near, or spanning one or more genes, exons, introns, UTRs, or a combination thereof. Capture probes may hybridize to one or more genomic regions spanning one or more genes, exons, introns, UTRs, or a combination thereof capture probes may hybridize to one or more known inDels. Capture probes may hybridize to one or more known structural variants.

Subsets of nucleic acid molecules may comprise labeled nucleic acid molecules. Two or more subsets of nucleic acid molecules may be differentiated into labeled nucleic acid molecules and non-labeled nucleic acid molecules. For example, a first subset of nucleic acid molecules may comprise one or more labeled nucleic acid molecules and a second subset of nucleic acid molecules may comprise non-labeled nucleic acid molecules. Non-labeled nucleic acid molecules may refer to nucleic acid molecules that are not attached to one or more labels. Non-labeled nucleic acid molecules may refer to nucleic acid molecules that have been detached from one or more labels. For example, the label from a labeled nucleic acid molecule may be removed to produce a non-labeled nucleic acid molecule.

The methods disclosed herein may comprise one or more labels. The one or more labels may be attached to one or more capture probes, nucleic acid molecules, beads, primers, or a combination thereof. Examples of labels include, but are not limited to, detectable labels, such as radioisotopes, fluorophores, chemiluminophores, chromophore, lumiphore, enzymes, colloidal particles, and fluorescent microparticles, quantum dots, as well as antigens, antibodies, haptens, avidin/streptavidin, biotin, haptens, enzymes cofactors/substrates, one or more members of a quenching system, a chromogens, haptens, a magnetic particles, materials exhibiting nonlinear optics, semiconductor nanocrystals, metal nanoparticles, enzymes, aptamers, and one or more members of a binding pair.

The one or more subsets of nucleic acid molecules may be subjected to one or more assays. The one or more subsets of nucleic acid molecules may be subjected to one or more assays based on their biochemical features. The one or more subsets of nucleic acid molecules may be subjected to one or more assays based on their genomic region features. The one or more subsets of nucleic acid molecules may be subjected to 1, 2, 3, 4, 5, 6, 7, 8, 9, 10 or more assays. The one or more subsets of nucleic acid molecules may be subjected to 1, 2, 3, 4, 5, 6, 7, 8, 9, 10 or more assays based on their biochemical features. The one or more subsets of nucleic acid molecules may be subjected to 1, 2, 3, 4, 5, 6, 7, 8, 9, 10 or more assays based on their genomic region features. The one or more subsets of nucleic acid molecules may be subjected to 1, 2, 3, 4, 5, 6, 7, 8, 9, 10 or more identical assays. The one or more subsets of nucleic acid molecules may be subjected to 1, 2, 3, 4, 5, 6, 7, 8, 9, 10 or more identical assays based on their biochemical features. The one or more subsets of nucleic acid molecules may be subjected to 1, 2, 3, 4, 5, 6, 7, 8, 9, 10 or more identical assays based on their genomic region features. The one or more subsets of nucleic acid molecules may be subjected to 1, 2, 3, 4, 5, 6, 7, 8, 9, 10 or more similar assays. The one or more subsets of nucleic acid molecules may be subjected to 1, 2, 3, 4, 5, 6, 7, 8, 9, 10 or more similar assays based on their biochemical features. The one or more subsets of nucleic acid molecules may be subjected to 1, 2, 3, 4, 5, 6, 7, 8, 9, 10 or more similar assays based on their genomic region features. The one or more subsets of nucleic acid molecules may be subjected to 1, 2, 3, 4, 5, 6, 7, 8, 9, 10 or more different assays. The one or more subsets of nucleic acid molecules may be subjected to 1, 2, 3, 4, 5, 6, 7, 8, 9, 10 or more different assays based on their biochemical features. The one or more subsets of nucleic acid molecules may be subjected to 1, 2, 3, 4, 5, 6, 7, 8, 9, 10 or more different assays based on their genomic region features. The two or more subsets of nucleic acid molecules may be subjected to one or more identical processing steps based on their biochemical features. The two or more subsets of nucleic acid molecules may be subjected to one or more identical processing steps based on their genomic region features. The two or more subsets of nucleic acid molecules may be subjected to one or more similar processing steps based on their biochemical features. The two or more subsets of nucleic acid molecules may be subjected to one or more similar processing steps based on their genomic region features. The two or more subsets of nucleic acid molecules may be subjected to one or more different processing steps based on their biochemical features. The two or more subsets of nucleic acid molecules may be subjected to one or more different processing steps based on their genomic region features.

The methods disclosed herein may comprise producing two or more subsets of nucleic acid molecules. The two or more subsets of nucleic acid molecules may be separated fluidically, separated into two or more containers, separated into two or more locations, or a combination thereof. For example, a first subset of nucleic acid molecules and a second subset of nucleic acid molecules are fluidically separated. In another example, a first subset of nucleic acid molecules is in a first container and second subset of nucleic acid molecules is in a second container. In yet another example, a first subset of nucleic acid molecules and a second subset of nucleic acid molecules are assigned to two or more locations on a first container, and a third subset of nucleic acid molecules is in a second container.

Genomic Regions

The methods disclosed herein may comprise nucleic acid samples or subsets of nucleic acid molecules comprising one or more genomic regions. The methods disclosed herein may comprise nucleic acid samples or subsets of nucleic acid molecules comprising one or more sets of genomic regions. The one or more genomic regions may comprise one or more genomic region features. The genomic region features may comprise an entire genome or a portion thereof. The genomic region features may comprise an entire exome or a portion thereof. The genomic region features may comprise one or more sets of genes. The genomic region features may comprise one or more genes. The genomic region features may comprise one or more sets of regulatory elements. The genomic region features may comprise one or more regulatory elements. The genomic region features may comprise a set of polymorphisms. The genomic region features may comprise one or more polymorphisms. The genomic region feature may relate to the GC content, complexity, and/or mappablity of one or more nucleic acid molecules. The genomic region features may comprise one or more simple tandem repeats (STRs), unstable expanding repeats, segmental duplications, single and paired read degenerative mapping scores, GRCh37 patches, or a combination thereof. The genomic region features may comprise one or more low mean coveage regions from whole genome sequencing (WGS), zero mean coverage regions from WGS, validated compressions, or a combination thereof. The genomic region features may comprise one or more alternate or non-reference sequences. The genomic region features may comprise one or more gene phasing and reassembly genes. In some aspects of the disclosure, the one or more genomic region features are not mutually exclusive. For example, a genomic region feature comprising an entire genome or a portion thereof can overlap with an additional genomic region feature such as an entire exome or a portion thereof, one or more genes, one or more regulatory elements, etc. Alternatively, the one or more genomic region futures are mutually exclusive. For example, a genomic region comprising the noncoding portion of an entire genome would not overlap with a genomic region feature such as an exome or portion thereof or the coding portion of a gene. Alternatively, or additionally, the one or more genomic region features are partially exclusive or partially inclusive. For example, a genomic region comprising an entire exome or a portion thereof can partially overlap with a genomic region comprising an exon portion of a gene. However, the genomic region comprising the entire exome or portion thereof would not overlap with the genomic region comprising the intron portion of the gene. Thus, a genomic region feature comprising a gene or portion thereof may partially exclude and/or partially include a genomic region feature comprising an entire exome or portion thereof.

The methods disclosed herein may comprise nucleic acid samples or subsets of nucleic acid molecules comprising one or more genomic regions, wherein at least one of the one or more genomic regions comprises a genomic region feature comprising an entire genome or portion thereof. The entire genome or portion thereof may comprise one or more coding portions of the genome, one or more noncoding portions of the genome, or a combination thereof. The coding portion of the genome may comprise one or more coding portions of a gene encoding for one or more proteins. The one or more coding portions of the genome may comprise an entire exome or a portion thereof. Alternatively, or additionally, the one or more coding portions of the genome may comprise one or more exons. The one or more noncoding portions of the genome may comprise one or more noncoding molecules or a portion thereof. The noncoding molecules may comprise one or more noncoding RNA, one or more regulatory elements, one or more introns, one or more pseudogenes, one or more repeat sequences, one or more transposons, one or more viral elements, one or more telomeres, a portion thereof, or a combination thereof. The noncoding RNAs may be functional RNA molecules that are not translated into protein. Examples of noncoding RNAs include, but are not limited to, ribosomal RNA, transfer RNA, piwi-interacting RNA, microRNA, siRNA, shRNA, snoRNA, sncRNA, and lncRNA. Pseudogenes may be related to known genes and are typically no longer expressed. Repeat sequences may comprise one or more tandem repeats, one or more interspersed repeats, or a combination thereof. Tandem repeats may comprise one or more satellite DNA, one or more minisatellites, one or more microsatellites, or a combination thereof. Interspersed repeats may comprise one or more transposons. Transposons may be mobile genetic elements. Mobile genetic elements are often able to change their position within the genome. Transposons may be classified as class I transposable elements (class I TEs) or class II transposable elements (class II TEs). Class I TEs (e.g., retrotransposons) may often copy themselves in two stages, first from DNA to RNA by transcription, then from RNA back to DNA by reverse transcription. The DNA copy may then be inserted into the genome in a new position. Class I TEs may comprise one or more long terminal repeats (LTRs), one or more long interspersed nuclear elements (LINEs), one or more short interspersed nuclear elements (SINEs), or a combination thereof. Examples of LTRs include, but are not limited to, human endogeneous retroviruses (HERVs), medium reiterated repeats 4 (MER4), and retrotransposon. Examples of LINES include, but are not limited to, LINE1 and LINE2. SINES may comprise one or more Alu sequences, one or more mammalian-wide interspersed repeat (MIR), or a combination thereof. Class II TEs (e.g., DNA transposons) often do not involve an RNA intermediate. The DNA transposon is often cut from one site and inserted into another site in the genome. Alternatively, the DNA transposon is replicated and inserted into the genome in a new position. Examples of DNA transposons include, but are not limited to, MER1, MER2, and mariners. Viral elements may comprise one or more endogenous retrovirus sequences. Telomeres are often regions of repetitive DNA at the end of a chromosome.

The methods disclosed herein may comprise nucleic acid samples or subsets of nucleic acid molecules comprising one or more genomic regions, wherein at least one of the one or more genomic regions comprises a genomic region feature comprising an entire exome or portion thereof. The exome is often the part of the genome formed by exons. The exome may be formed by untranslated regions (UTRs), splice sites and/or intronic regions. The entire exome or portion thereof may comprise one or more exons of a protein coding gene. The entire exome or portion thereof may comprise one or more untranslated regions (UTRs), splice sites, and introns.

The methods disclosed herein may comprise nucleic acid samples or subsets of nucleic acid molecules comprising one or more genomic regions, wherein at least one of the one or more genomic regions comprises a genomic region feature comprising a gene or portion thereof. Typically, a gene comprises stretches of nucleic acids that code for a polypeptide or a functional RNA. A gene may comprise one or more exons, one or more introns, one or more untranslated regions (UTRs), or a combination thereof. Exons are often coding sections of a gene, transcribed into a precursor mRNA sequence, and within the final mature RNA product of the gene. Introns are often noncoding sections of a gene, transcribed into a precursor mRNA sequence, and removed by RNA splicing. UTRs may refer to sections on each side of a coding sequence on a strand of mRNA. A UTR located on the 5' side of a coding sequence may be called the 5' UTR (or leader sequence). A UTR located on the 3' side of a coding sequence may be called the 3' UTR (or trailer sequence). The UTR may contain one or more elements for controlling gene expression. Elements, such as regulatory elements, may be located in the 5' UTR. Regulatory sequences, such as a polyadenylation signal, binding sites for proteins, and binding sites for miRNAs, may be located in the 3' UTR. Binding sites for proteins located in the 3' UTR may include, but are not limited to, selenocysteine insertion sequence (SECIS) elements and AU-rich elements (AREs). SECIS elements may direct a ribosome to translate the codon UGA as selenocysteine rather than as a stop codon. AREs are often stretches consisting primarily of adenine and uracil nucleotides, which may affect the stability of a mRNA.

The methods disclosed herein may comprise nucleic acid samples or subsets of nucleic acid molecules comprising one or more genomic regions, wherein at least one of the one or more genomic regions comprises a genomic region feature comprising a set of genes. The sets of genes may include, but are not limited to, Mendel DB Genes, Human Gene Mutation Database (HGMD) Genes, Cancer Gene Census Genes, Online Mendelian Inheritance in Man (OMIM) Mendelian Genes, HGMD Mendelian Genes, and human leukocyte antigen (HLA) Genes. The set of genes may have one or more known Mendelian traits, one or more known disease traits, one or more known drug traits, one or more known biomedically interpretable variants, or a combination thereof. A Mendelian trait may be controlled by a single locus and may show a Mendelian inheritance pattern. A set of genes with known Mendelian traits may comprise one or more genes encoding Mendelian traits including, but are not limited to, ability to taste phenylthiocarbamide (dominant), ability to smell (bitter almond-like) hydrogen cyanide (recessive), albinism (recessive), brachydactyly (shortness of fingers and toes), and wet (dominant) or dry (recessive) earwax. A disease trait cause or increase risk of disease and may be inherited in a Mendelian or complex pattern. A set of genes with known disease traits may comprise one or more genes encoding disease traits including, but are not limited to, Cystic Fibrosis, Hemophilia, and Lynch Syndrome. A drug trait may alter metabolism, optimal dose, adverse reactions and side effects of one or more drugs or family of drugs. A set of genes with known drug traits may comprise one or more genes encoding drug traits including, but are not limited to, CYP2D6, UGT1A1 and ADRB1. A biomedically interpretable variant may be a polymorphism in a gene that is associated with a disease or indication. A set of genes with known biomedically interpretable variants may comprise one or more genes encoding biomedically interpretable variants including, but are not limited to, cystic fibrosis (CF) mutations, muscular dystrophy mutations, p53 mutations, Rb mutations, cell cycle regulators, receptors, and kinases. Alternatively, or additionally, a set of genes with known biomedically interpretable variants may comprise one or more genes associated with Huntington's disease, cancer, cystic fibrosis, muscular dystrophy (e.g., Duchenne muscular dystrophy).

The methods disclosed herein may comprise nucleic acid samples or subsets of nucleic acid molecules comprising one or more genomic regions, wherein at least one of the one or more genomic regions comprises a genomic region feature comprising a regulatory element or a portion thereof. Regulatory elements may be cis-regulatory elements or trans-regulatory elements. Cis-regulatory elements may be sequences that control transcription of a nearby gene. Cis-regulatory elements may be located in the 5' or 3' untranslated regions (UTRs) or within introns. Trans-regulatory elements may control transcription of a distant gene. Regulatory elements may comprise one or more promoters, one or more enhancers, or a combination thereof promoters may facilitate transcription of a particular gene and may be found upstream of a coding region Enhancers may exert distant effects on the transcription level of a gene.

The methods disclosed herein may comprise nucleic acid samples or subsets of nucleic acid molecules comprising one or more genomic regions, wherein at least one of the one or more genomic regions comprises a genomic region feature comprising a polymorphism or a portion thereof. Generally, a polymorphism refers to a mutation in a genotype. A polymorphism may comprise one or more base changes, an insertion, a repeat, or a deletion of one or more bases. Copy number variants (CNVs), transversions and other rearrangements are also forms of genetic variation. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are a form of polymorphisms. In some aspects of the disclosure, one or more polymorphisms comprise one or more single nucleotide variations, inDels, small insertions, small deletions, structural variant junctions, variable length tandem repeats, flanking sequences, or a combination thereof. The one or more polymorphisms may be located within a coding and/or non-coding region. The one or more polymorphisms may be located within, around, or near a gene, exon, intron, splice site, untranslated region, or a combination thereof. The one or more polymorphisms may be may span at least a portion of a gene, exon, intron, untranslated region.

The methods disclosed herein may comprise nucleic acid samples or subsets of nucleic acid molecules comprising one or more genomic regions, wherein at least one of the one or more genomic regions comprises a genomic region feature comprising one or more simple tandem repeats (STRs), unstable expanding repeats, segmental duplications, single and paired read degenerative mapping scores, GRCh37 patches, or a combination thereof. The one or more STRs may comprise one or more homopolymers, one or more dinucleotide repeats, one or more trinucleotide repeats, or a combination thereof. The one or more homopolymers may be about 7, 8, 9, 10, 11, 12, 13, 14, 15, 16, 17, 18, 19, 20 or more bases or base pairs. The dinucleotide repeats and/or trinucleotide repeats may be about 15, 16, 17, 18, 19, 20, 21, 22, 23, 24, 25, 26, 27, 28, 29, 30, 35, 40, 45, 50 or more bases or base pairs. The single and paired read degenerative mapping scores may be based on or derived from alignability of 100mers by GEM from ENCODE/CRG (Guigo), alignability of 75mers by GEM from ENCODE/CRG (Guigo), 100 base pair box car average for signal mappability, max of locus and possible pairs for paired read score, or a combination thereof. The genomic region features may comprise one or more low mean coverage regions from whole genome sequencing (WGS), zero mean coverage regions from WGS, validated compressions, or a combination thereof. The low mean coverage regions from WGS may comprise regions generated from Illumina v3 chemistry, regions below the first percentile of Poission distribution based on mean coverage, or a combination thereof. The Zero mean coverage regions from WGS may comprise regions generated from Illumina v3 chemistry. The validated compressions may comprise regions of high mapped depth, regions with two or more observed haplotypes, regions expected to be missing repeats in a reference, or a combination thereof. The genomic region features may comprise one or more alternate or non-reference sequences. The one or more alternate or non-reference sequences may comprise known structural variant junctions, known insertions, known deletions, alternate haplotypes, or a combination thereof. The genomic region features may comprise one or more gene phasing and reassembly genes. Examples of phasing and reassembly genes include, but are not limited to, one or more major histocompatibility complexes, blood typing, and amaylase gene family. The one or more major histocompatibility complexes may comprise one or more HLA Class I, HLA Class II, or a combination thereof. The one or more HLA class I may comprise HLA-A, HLA-B, HLA-C, or a combination thereof. The one or more HLA class II may comprise HLA-DP, HLA-DM, HLA-DOA, HLA-DOB, HLA-DQ, HLA-DR, or a combination thereof. The blood typing genes may comprise ABO, RHD, RHCE, or a combination thereof.

The methods disclosed herein may comprise nucleic acid samples or subsets of nucleic acid molecules comprising one or more genomic regions, wherein at least one of the one or more genomic regions comprises a genomic region feature related to the GC content of one or more nucleic acid molecules. The GC content may refer to the GC content of a nucleic acid molecule. Alternatively, the GC content may refer to the GC content of one or more nucleic acid molecules and may be referred to as the mean GC content. As used herein, the terms "GC content" and "mean GC content" may be used interchangeably. The GC content of a genomic region may be a high GC content. Typically, a high GC content refers to a GC content of greater than or equal to about 65%, 70%, 75%, 80%, 85%, 90%, 95%, 97%, or more. In some aspects of the disclosure, a high GC content may refer to a GC content of greater than or equal to about 70%. The GC content of a genomic region may be a low GC content. Typically, a low GC content refers to a GC content of less than or equal to about 65%, 60%, 55%, 50%, 45%, 40%, 35%, 30%, 25%, 20%, 15%, 10%, 5%, 2%, or less.

The difference in GC content may be used to differentiate two or more genomic regions or two or more subsets of nucleic acid molecules. The difference in GC content may refer to the difference in GC content of one nucleic acid molecule and another nucleic acid molecule. Alternatively, the difference in GC content may refer to the difference in mean GC content of two or more nucleic acid molecules in a genomic region from the mean GC content of two or more nucleic acid molecules in another genomic region. In some aspects of the disclosure, the difference in GC content refers to the difference in mean GC content of two or more nucleic acid molecules in a subset of nucleic acid molecules from the mean GC content of two or more nucleic acid molecules in another subset of nucleic acid molecules. The difference in GC content may be about 5%, 6%, 7%, 8%, 9%, 10%, 15%, 20%, 25%, 30%, 35%, 40%, or more. In some aspects of the disclosure, the difference in GC content is at least about 5%. The difference in GC content may be at least about 10%.

The methods disclosed herein may comprise nucleic acid samples or subsets of nucleic acid molecules comprising one or more genomic regions, wherein at least one of the one or more genomic regions comprises a genomic region feature related to the complexity of one or more nucleic acid molecules. The complexity of a nucleic acid molecule may refer to the randomness of a nucleotide sequence. Low complexity may refer to patterns, repeats and/or depletion of one or more species of nucleotide in the sequence.

The methods disclosed herein may comprise nucleic acid samples or subsets of nucleic acid molecules comprising one or more genomic regions, wherein at least one of the one or more genomic regions comprises a genomic region feature related to the mappablity of one or more nucleic acid molecules. The mappability of a nucleic acid molecule may refer to uniqueness of its alignment to a reference sequence. A nucleic acid molecule with low mappability may have poor alignment to a reference sequence.

The methods disclosed herein may comprise nucleic acid samples or subsets of nucleic acid molecules comprising one or more genomic regions comprising one or more genomic region features. In some aspects of the disclosure, a single genomic region comprises 1 or more, 2 or more, 3 or more, 4 or more, 5 or more, 6 or more, 7 or more, 8 or more, 9 or more, 10 or more, 11 or more, 12 or more, 13 or more, 14 or more, or 15 or more genomic region features. The two or more genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more genomic region features. In some aspects of the disclosure, two or more genomic regions comprise 1 or more, 2 or more, 3 or more, 4 or more, 5 or more, 6 or more, 7 or more, 8 or more, 9 or more, 10 or more, 11 or more, 12 or more, 13 or more, 14 or more, or 15 or more genomic region features. The one or more genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more identical or similar genomic region features. Alternatively, or additionally, two or more genomic regions comprise 1 or more, 2 or more, 3 or more, 4 or more, 5 or more, 6 or more, 7 or more, 8 or more, 9 or more, 10 or more, 11 or more, 12 or more, 13 or more, 14 or more, or 15 or more genomic region features. The one or more genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more different genomic region features.

The methods disclosed herein may comprise nucleic acid samples or subsets of nucleic acid molecules comprising two or more genomic regions, wherein the two or more genomic regions are differentiateable by one or more genomic region features. The methods disclosed herein may comprise nucleic acid samples or subsets of nucleic acid molecules comprising two or more subsets of nucleic acid molecules, wherein the two or more subsets of nucleic acid molecules are differentiateable by one or more genomic region features. The two or more genomic regions and/or the two or more subsets of nucleic acid molecules may be differentiateable by 1 or more, 2 or more, 3 or more, 4 or more, 5 or more, 6 or more, 7 or more, 8 or more, 9 or more, 10 or more, 11 or more, 12 or more, 13 or more, 14 or more, or 15 or more genomic region features. The one or more genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, or 30 or more genomic region features.

The methods disclosed herein may comprise nucleic acid samples or subsets of nucleic acid molecules comprising one or more sets of genomic regions. For example, the methods disclosed herein may comprise nucleic acid samples or subsets of nucleic acid molecules comprising, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more sets of genomic regions. The one or more sets of genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more different genomic regions. The one or more sets of genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more identical or similar genomic regions. The one or more sets of genomic regions may comprise a combination of one or more different genomic regions and one or more identical or similar genomic regions.

Capture Probes

The methods disclosed herein may comprise one or more capture probes, a plurality of capture probes, or one or more capture probe sets. Typically, the capture probe comprises a nucleic acid binding site. The capture probe may further comprise one or more linkers. The capture probes may further comprise one or more labels. The one or more linkers may attach the one or more labels to the nucleic acid binding site.

The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more capture probes or capture probe sets. The one or more capture probes or capture probe sets may be different, similar, identical, or a combination thereof.

The one or more capture probe may comprise a nucleic acid binding site that hybridizes to at least a portion of the one or more nucleic acid molecules or variant or derivative thereof in the sample or subset of nucleic acid molecules. The capture probes may comprise a nucleic acid binding site that hybridizes to one or more genomic regions. The capture probes may hybridize to different, similar, and/or identical genomic regions. The one or more capture probes may be at least about 50%, 55%, 60%, 65%, 70%, 75%, 80%, 85%, 90%, 95%, 97%, 99% or more complementary to the one or more nucleic acid molecules or variant or derivative thereof.

The capture probes may comprise one or more nucleotides. The capture probes may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more nucleotides. The capture probes may comprise about 100 nucleotides. The capture probes may comprise between about 10 to about 500 nucleotides, between about 20 to about 450 nucleotides, between about 30 to about 400 nucleotides, between about 40 to about 350 nucleotides, between about 50 to about 300 nucleotides, between about 60 to about 250 nucleotides, between about 70 to about 200 nucleotides, or between about 80 to about 150 nucleotides. In some aspects of the disclosure, the capture probes comprise between about 80 nucleotides to about 100 nucleotides.

The plurality of capture probes or the capture probe sets may comprise two or more capture probes with identical, similar, and/or different nucleic acid binding site sequences, linkers, and/or labels. For example, two or more capture probes comprise identical nucleic acid binding sites. In another example, two or more capture probes comprise similar nucleic acid binding sites. In yet another example, two or more capture probes comprise different nucleic acid binding sites. The two or more capture probes may further comprise one or more linkers. The two or more capture probes may further comprise different linkers. The two or more capture probes may further comprise similar linkers. The two or more capture probes may further comprise identical linkers. The two or more capture probes may further comprise one or more labels. The two or more capture probes may further comprise different labels. The two or more capture probes may further comprise similar labels. The two or more capture probes may further comprise identical labels.

Assays and Techniques

The methods disclosed herein may comprise producing one or more subsets of nucleic acid molecules from a nucleic acid sample. The methods disclosed herein may comprise producing 1, 2, 3, 4, 5, 6, 7, 8, 9, 10, 11, 12, 13, 14, 15 or more subsets of nucleic acid molecules from a nucleic acid sample. The one or more subsets of nucleic acid molecules may be produced by contacting a nucleic acid sample with one or more beads, capture probes, labels, or a combination thereof. Alternatively, or additionally, the one or more subsets of nucleic acid molecules are produced by separating at least one nucleic acid molecule from another nucleic acid molecule.

The methods disclosed herein may comprise producing two or more subsets of nucleic acids may by contacting a nucleic acid sample with one or more beads to produce a first subset of nucleic acid molecules comprising one or more bead bound nucleic acid molecules and a second subset of nucleic acid molecules comprising one or more bead free nucleic acid molecules.

Alternatively, or additionally, methods disclosed herein may comprise producing two or more subsets of nucleic acids may by contacting the nucleic acid sample with one or more capture probes to produce a first subset of nucleic acid molecules comprising one or more capture probe hybridized nucleic acid molecules and a second subset of nucleic acid molecules comprising one or more capture probe free nucleic acid molecules.

In some aspects of the disclosure, producing the two or more subsets of nucleic acids comprises contacting the nucleic acid sample with one or more labels to produce a first subset of nucleic acid molecules comprising one or more labeled nucleic acid molecules and a second subset of nucleic acid molecules comprising one or more non-labeled nucleic acid molecules.

Producing the two or more subsets of nucleic acids comprises contacting the nucleic acid sample with one or more capture probes to produce a first subset of nucleic acid molecules comprising one or more capture probe hybridized nucleic acid molecules and a second subset of nucleic acid molecules comprising one or more capture probe free nucleic acid molecules.

The methods disclosed herein may comprise conducting one or more assays on a sample comprising one or more nucleic acid molecules. Producing two or more subsets of nucleic acid molecules may comprise conducting one or more assays. The assays may be conducted on a subset of nucleic acid molecules from the sample. The assays may be conducted on one or more nucleic acids molecules from the sample. The assays may be conducted on at least a portion of a subset of nucleic acid molecules. The assays may comprise one or more techniques, reagents, capture probes, primers, labels, and/or components for the detection, quantification, and/or analysis of one or more nucleic acid molecules.

The methods disclosed herein may comprise conducting one or more assays on two or more subsets of nucleic acid molecules. The methods disclosed herein may further comprise combining at least a portion of two or more subsets of nucleic acid molecules to produce a combined subset of nucleic acid molecules and conducting at least one assay on the combined subset of nucleic acid molecules. In some aspects of the disclosure, two or more subsets of nucleic acid molecules may be produced by one or more methods disclosed herein, Assays may include, but are not limited to, sequencing, amplification, hybridization, enrichment, isolation, elution, fragmentation, detection, quantification of one or more nucleic acid molecules. Assays may include methods for preparing one or more nucleic acid molecules.

The methods disclosed herein may comprise conducting one or more sequencing reactions on one or more nucleic acid molecules in a sample. The methods disclosed herein may comprise conducting 1 or more, 2 or more, 3 or more, 4 or more, 5 or more, 6 or more, 7 or more, 8 or more, 9 or more, 10 or more, 15 or more, 20 or more, 30 or more, 40 or more, 50 or more, 60 or more, 70 or more, 80 or more, 90 or more, 100 or more, 200 or more, 300 or more, 400 or more, 500 or more, 600 or more, 700 or more, 800 or more, 900 or more, or 1000 or more sequencing reactions on one or more nucleic acid molecules in a sample. The sequencing reactions may be run simultaneously, sequentially, or a combination thereof. The sequencing reactions may comprise whole genome sequencing or exome sequencing. The sequencing reactions may comprise Maxim-Gilbert, chain-termination or high-throughput systems. Alternatively, or additionally, the sequencing reactions may comprise Helioscope™ single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent™, Ion semiconductor sequencing, Single Molecule SMRT™ sequencing, Polony sequencing, DNA nanoball sequencing, VisiGen Biotechnologies approach, or a combination thereof. Alternatively, or additionally, the sequencing reactions can comprise one or more sequencing platforms, including, but not limited to, Genome Analyzer IIx, HiSeq, and MiSeq offered by Illumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, Mass.). Sequencing reactions may also comprise electron microscopy or a chemical-sensitive field effect transistor (chemFET) array. In some aspects of the disclosure, sequencing reactions comprise capillary sequencing, next generation sequencing, Sanger sequencing, sequencing by synthesis, sequencing by ligation, sequencing by hybridization, single molecule sequencing, or a combination thereof. Sequencing by synthesis may comprise reversible terminator sequencing, processive single molecule sequencing, sequential flow sequencing, or a combination thereof. Sequential flow sequencing may comprise pyrosequencing, pH-mediated sequencing, semiconductor sequencing, or a combination thereof.

The methods disclosed herein may comprise conducting at least one long read sequencing reaction and at least one short read sequencing reaction. The long read sequencing reaction and/or short read sequencing reaction may be conducted on at least a portion of a subset of nucleic acid molecules. The long read sequencing reaction and/or short read sequencing reaction may be conducted on at least a portion of two or more subsets of nucleic acid molecules. Both a long read sequencing reaction and a short read sequencing reaction may be conducted on at least a portion of one or more subsets of nucleic acid molecules.

Sequencing of the one or more nucleic acid molecules or subsets thereof may comprise at least about 5; 10; 15; 20; 25; 30; 35; 40; 45; 50; 60; 70; 80; 90; 100; 200; 300; 400; 500; 600; 700; 800; 900; 1,000; 1500; 2,000; 2500; 3,000; 3500; 4,000; 4500; 5,000; 5500; 6,000; 6500; 7,000; 7500; 8,000; 8500; 9,000; 10,000; 25,000; 50,000; 75,000; 100,000; 250,000; 500,000; 750,000; 10,000,000; 25,000,000; 50,000,000; 100,000,000; 250,000,000; 500,000,000; 750,000,000; 1,000,000,000 or more sequencing reads.

Sequencing reactions may comprise sequencing at least about 50; 60; 70; 80; 90; 100; 110; 120; 130; 140; 150; 160; 170; 180; 190; 200; 210; 220; 230; 240; 250; 260; 270; 280; 290; 300; 325; 350; 375; 400; 425; 450; 475; 500; 600; 700; 800; 900; 1,000; 1500; 2,000; 2500; 3,000; 3500; 4,000; 4500; 5,000; 5500; 6,000; 6500; 7,000; 7500; 8,000; 8500; 9,000; 10,000; 20,000; 30,000; 40,000; 50,000; 60,000; 70,000; 80,000; 90,000; 100,000 or more bases or base pairs of one or more nucleic acid molecules. Sequencing reactions may comprise sequencing at least about 50; 60; 70; 80; 90; 100; 110; 120; 130; 140; 150; 160; 170; 180; 190; 200; 210; 220; 230; 240; 250; 260; 270; 280; 290; 300; 325; 350; 375; 400; 425; 450; 475; 500; 600; 700; 800; 900; 1,000; 1500; 2,000; 2500; 3,000; 3500; 4,000; 4500; 5,000; 5500; 6,000; 6500; 7,000; 7500; 8,000; 8500; 9,000; 10,000; 20,000; 30,000; 40,000; 50,000; 60,000; 70,000; 80,000; 90,000; 100,000 or more consecutive bases or base pairs of one or more nucleic acid molecules.

Preferably, the sequencing techniques used in the methods of the invention generates at least 100 reads per run, at least 200 reads per run, at least 300 reads per run, at least 400 reads per run, at least 500 reads per run, at least 600 reads per run, at least 700 reads per run, at least 800 reads per run, at least 900 reads per run, at least 1000 reads per run, at least 5,000 reads per run, at least 10,000 reads per run, at least 50,000 reads per run, at least 100,000 reads per run, at least 500,000 reads per run, or at least 1,000,000 reads per run. Alternatively, the sequencing technique used in the methods of the invention generates at least 1,500,000 reads per run, at least 2,000,000 reads per run, at least 2,500,000 reads per run, at least 3,000,000 reads per run, at least 3,500,000 reads per run, at least 4,000,000 reads per run, at least 4,500,000 reads per run, or at least 5,000,000 reads per run.

Preferably, the sequencing techniques used in the methods of the invention can generate at least about 30 base pairs, at least about 40 base pairs, at least about 50 base pairs, at least about 60 base pairs, at least about 70 base pairs, at least about 80 base pairs, at least about 90 base pairs, at least about 100 base pairs, at least about 110, at least about 120 base pairs per read, at least about 150 base pairs, at least about 200 base pairs, at least about 250 base pairs, at least about 300 base pairs, at least about 350 base pairs, at least about 400 base pairs, at least about 450 base pairs, at least about 500 base pairs, at least about 550 base pairs, at least about 600 base pairs, at least about 700 base pairs, at least about 800 base pairs, at least about 900 base pairs, or at least about 1,000 base pairs per read. Alternatively, the sequencing technique used in the methods of the invention can generate long sequencing reads. In some instances, the sequencing technique used in the methods of the invention can generate at least about 1,200 base pairs per read, at least about 1,500 base pairs per read, at least about 1,800 base pairs per read, at least about 2,000 base pairs per read, at least about 2,500 base pairs per read, at least about 3,000 base pairs per read, at least about 3,500 base pairs per read, at least about 4,000 base pairs per read, at least about 4,500 base pairs per read, at least about 5,000 base pairs per read, at least about 6,000 base pairs per read, at least about 7,000 base pairs per read, at least about 8,000 base pairs per read, at least about 9,000 base pairs per read, at least about 10,000 base pairs per read, 20,000 base pairs per read, 30,000 base pairs per read, 40,000 base pairs per read, 50,000 base pairs per read, 60,000 base pairs per read, 70,000 base pairs per read, 80,000 base pairs per read, 90,000 base pairs per read, or 100,000 base pairs per read.

High-throughput sequencing systems may allow detection of a sequenced nucleotide immediately after or upon its incorporation into a growing strand, i.e., detection of sequence in real time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120, at least 150, at least 200, at least 250, at least 300, at least 350, at least 400, at least 450, or at least 500 bases per read. Sequencing can be performed using nucleic acids described herein such as genomic DNA, cDNA derived from RNA transcripts or RNA as a template.

The methods disclosed herein may comprise conducting one or more amplification reactions on one or more nucleic acid molecules in a sample. The term "amplification" refers to any process of producing at least one copy of a nucleic acid molecule. The terms "amplicons" and "amplified nucleic acid molecule" refer to a copy of a nucleic acid molecule and can be used interchangeably. The amplification reactions can comprise PCR-based methods, non-PCR based methods, or a combination thereof. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. PCR-based methods may include, but are not limited to, PCR, HD-PCR, Next Gen PCR, digital RTA, or any combination thereof. Additional PCR methods include, but are not limited to, linear amplification, allele-specific PCR, Alu PCR, assembly PCR, asymmetric PCR, droplet PCR, emulsion PCR, helicase dependent amplification HDA, hot start PCR, inverse PCR, linear-after-the-exponential (LATE)-PCR, long PCR, multiplex PCR, nested PCR, hemi-nested PCR, quantitative PCR, RT-PCR, real time PCR, single cell PCR, and touchdown PCR.

The methods disclosed herein may comprise conducting one or more hybridization reactions on one or more nucleic acid molecules in a sample. The hybridization reactions may comprise the hybridization of one or more capture probes to one or more nucleic acid molecules in a sample or subset of nucleic acid molecules. The hybridization reactions may comprise hybridizing one or more capture probe sets to one or more nucleic acid molecules in a sample or subset of nucleic acid molecules. The hybridization reactions may comprise one or more hybridization arrays, multiplex hybridization reactions, hybridization chain reactions, isothermal hybridization reactions, nucleic acid hybridization reactions, or a combination thereof. The one or more hybridization arrays may comprise hybridization array genotyping, hybridization array proportional sensing, DNA hybridization arrays, macroarrays, microarrays, high-density oligonucleotide arrays, genomic hybridization arrays, comparative hybridization arrays, or a combination thereof. The hybridization reaction may comprise one or more capture probes, one or more beads, one or more labels, one or more subsets of nucleic acid molecules, one or more nucleic acid samples, one or more reagents, one or more wash buffers, one or more elution buffers, one or more hybridization buffers, one or more hybridization chambers, one or more incubators, one or more separators, or a combination thereof.

The methods disclosed herein may comprise conducting one or more enrichment reactions on one or more nucleic acid molecules in a sample. The enrichment reactions may comprise contacting a sample with one or more beads or bead sets. The enrichment reaction may comprise differential amplification of two or more subsets of nucleic acid molecules based on one or more genomic region features. For example, the enrichment reaction comprises differential amplification of two or more subsets of nucleic acid molecules based on GC content. Alternatively, or additionally, the enrichment reaction comprises differential amplification of two or more subsets of nucleic acid molecules based on methylation state. The enrichment reactions may comprise one or more hybridization reactions. The enrichment reactions may further comprise isolation and/or purification of one or more hybridized nucleic acid molecules, one or more bead bound nucleic acid molecules, one or more free nucleic acid molecules (e.g., capture probe free nucleic acid molecules, bead free nucleic acid molecules), one or more labeled nucleic acid molecules, one or more non-labeled nucleic acid molecules, one or more amplicons, one or more non-amplified nucleic acid molecules, or a combination thereof. Alternatively, or additionally, the enrichment reaction may comprise enriching for one or more cell types in the sample. The one or more cell types may be enriched by flow cytometry.

The one or more enrichment reactions may produce one or more enriched nucleic acid molecules. The enriched nucleic acid molecules may comprise a nucleic acid molecule or variant or derivative thereof. For example, the enriched nucleic acid molecules comprise one or more hybridized nucleic acid molecules, one or more bead bound nucleic acid molecules, one or more free nucleic acid molecules (e.g., capture probe free nucleic acid molecules, bead free nucleic acid molecules), one or more labeled nucleic acid molecules, one or more non-labeled nucleic acid molecules, one or more amplicons, one or more non-amplified nucleic acid molecules, or a combination thereof. The enriched nucleic acid molecules may be differentiated from non-enriched nucleic acid molecules by GC content, molecular size, genomic regions, genomic region features, or a combination thereof. The enriched nucleic acid molecules may be derived from one or more assays, supernatants, eluants, or a combination thereof. The enriched nucleic acid molecules may differ from the non-enriched nucleic acid molecules by mean size, mean GC content, genomic regions, or a combination thereof.

The methods disclosed herein may comprise conducting one or more isolation or purification reactions on one or more nucleic acid molecules in a sample. The isolation or purification reactions may comprise contacting a sample with one or more beads or bead sets. The isolation or purification reaction may comprise one or more hybridization reactions, enrichment reactions, amplification reactions, sequencing reactions, or a combination thereof. The isolation or purification reaction may comprise the use of one or more separators. The one or more separators may comprise a magnetic separator. The isolation or purification reaction may comprise separating bead bound nucleic acid molecules from bead free nucleic acid molecules. The isolation or purification reaction may comprise separating capture probe hybridized nucleic acid molecules from capture probe free nucleic acid molecules. The isolation or purification reaction may comprise separating a first subset of nucleic acid molecules from a second subset of nucleic acid molecules, wherein the first subset of nucleic acid molecules differ from the second subset on nucleic acid molecules by mean size, mean GC content, genomic regions, or a combination thereof.

The methods disclosed herein may comprise conducting one or more elution reactions on one or more nucleic acid molecules in a sample. The elution reactions may comprise contacting a sample with one or more beads or bead sets.

The elution reaction may comprise separating bead bound nucleic acid molecules from bead free nucleic acid molecules. The elution reaction may comprise separating capture probe hybridized nucleic acid molecules from capture probe free nucleic acid molecules. The elution reaction may comprise separating a first subset of nucleic acid molecules from a second subset of nucleic acid molecules, wherein the first subset of nucleic acid molecules differ from the second subset on nucleic acid molecules by mean size, mean GC content, genomic regions, or a combination thereof.

The methods disclosed herein may comprise one or more fragmentation reactions. The fragmentation reactions may comprise fragmenting one or more nucleic acid molecules in a sample or subset of nucleic acid molecules to produce one or more fragmented nucleic acid molecules. The one or more nucleic acid molecules may be fragmented by sonication, needle shear, nebulisation, shearing (e.g., acoustic shearing, mechanical shearing, point-sink shearing), passage through a French pressure cell, or enzymatic digestion. Enzymatic digestion may occur by nuclease digestion (e.g., micrococcal nuclease digestion, endonucleases, exonucleases, RNAse H or DNase I). Fragmentation of the one or more nucleic acid molecules may result in fragment sized of about 100 base pairs to about 2000 base pairs, about 200 base pairs to about 1500 base pairs, about 200 base pairs to about 1000 base pairs, about 200 base pairs to about 500 base pairs, about 500 base pairs to about 1500 base pairs, and about 500 base pairs to about 1000 base pairs. The one or more fragmentation reactions may result in fragment sized of about 50 base pairs to about 1000 base pairs. The one or more fragmentation reactions may result in fragment sized of about 100 base pairs, 150 base pairs, 200 base pairs, 250 base pairs, 300 base pairs, 350 base pairs, 400 base pairs, 450 base pairs, 500 base pairs, 550 base pairs, 600 base pairs, 650 base pairs, 700 base pairs, 750 base pairs, 800 base pairs, 850 base pairs, 900 base pairs, 950 base pairs, 1000 base pairs or more.

Fragmenting the one or more nucleic acid molecules may comprise mechanical shearing of the one or more nucleic acid molecules in the sample for a period of time. The fragmentation reaction may occur for at least about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more seconds.

Fragmenting the one or more nucleic acid molecules may comprise contacting a nucleic acid sample with one or more beads. Fragmenting the one or more nucleic acid molecules may comprise contacting the nucleic acid sample with a plurality of beads, wherein the ratio of the volume of the plurality of beads to the volume of nucleic acid sample is about 0.10, 0.20, 0.30, 0.40, 0.50, 0.60, 0.70, 0.80, 0.90, 1.00, 1.10, 1.20, 1.30, 1.40, 1.50, 1.60, 1.70, 1.80, 1.90, 2.00 or more. Fragmenting the one or more nucleic acid molecules may comprise contacting the nucleic acid sample with a plurality of beads, wherein the ratio of the volume of the plurality of beads to the volume of nucleic acid is about 2.00, 1.90, 1.80, 1.70, 1.60, 1.50, 1.40, 1.30, 1.20, 1.10, 1.00, 0.90, 0.80, 0.70, 0.60, 0.50, 0.40, 0.30, 0.20, 0.10, 0.05, 0.04, 0.03, 0.02, 0.01 or less.

The methods disclosed herein may comprise conducting one or more detection reactions on one or more nucleic acid molecules in a sample. Detection reactions may comprise one or more sequencing reactions. Alternatively, conducting a detection reaction comprises optical sensing, electrical sensing, or a combination thereof. Optical sensing may comprise optical sensing of a photoilluminscence photon emission, fluorescence photon emission, pyrophosphate photon emission, chemiluminescence photon emission, or a combination thereof. Electrical sensing may comprise electrical sensing of an ion concentration, ion current modulation, nucleotide electrical field, nucleotide tunneling current, or a combination thereof.

The methods disclosed herein may comprise conducting one or more quantification reactions on one or more nucleic acid molecules in a sample. Quantification reactions may comprise sequencing, PCR, qPCR, digital PCR, or a combination thereof.

The methods disclosed herein may comprise one or more samples. The methods disclosed herein may comprise 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100 or more samples. The sample may be derived from a subject. The two or more samples may be derived from a single subject. The two or more samples may be derived from t2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100 or more different subjects. The subject may be a mammal, reptiles, amphibians, avians, and fish. The mammal may be a human, ape, orangutan, monkey, chimpanzee, cow, pig, horse, rodent, bird, reptile, dog, cat, or other animal. A reptile may be a lizard, snake, alligator, turtle, crocodile, and tortoise. An amphibian may be a toad, frog, newt, and salamander. Examples of avians include, but are not limited to, ducks, geese, penguins, ostriches, and owls. Examples of fish include, but are not limited to, catfish, eels, sharks, and swordfish. Preferably, the subject is a human. The subject may suffer from a disease or condition.

The two or more samples may be collected over 1, 2, 3, 4, 5, 6, 7, 8, 9, 10, 11, 12, 15, 20, 30, 40, 50, 60, 70, 80, 90, 100, 200, 300, 400, 500, 600, 700, 800, 900, 1000 or time points. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more hour period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more day period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more week period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more month period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more year period.

The sample may be from a body fluid, cell, skin, tissue, organ, or combination thereof. The sample may be a blood, plasma, a blood fraction, saliva, sputum, urine, semen, transvaginal fluid, cerebrospinal fluid, stool, a cell or a tissue biopsy. The sample may be from an adrenal gland, appendix, bladder, brain, ear, esophagus, eye, gall bladder, heart, kidney, large intestine, liver, lung, mouth, muscle, nose, pancreas, parathyroid gland, pineal gland, pituitary gland, skin, small intestine, spleen, stomach, thymus, thyroid gland, trachea, uterus, vermiform appendix, cornea, skin, heart valve, artery, or vein The samples may comprise one or more nucleic acid molecules. The nucleic acid molecule may be a DNA molecule, RNA molecule (e.g. mRNA, cRNA or miRNA), and DNA/RNA hybrids. Examples of DNA molecules include, but are not limited to, double-stranded DNA, single-stranded DNA, single-stranded DNA hairpins, cDNA, genomic DNA. The nucleic acid may be an RNA molecule, such as a double-stranded RNA, single-stranded RNA, ncRNA, RNA hairpin, and mRNA. Examples of ncRNA include, but are not limited to, siRNA, miRNA, snoRNA, piRNA, tiRNA, PASR, TASR, aTASR, TSSa-RNA, snRNA, RE-RNA, uaRNA, x-ncRNA, hY RNA, usRNA, snaR, and vtRNA.

The methods disclosed herein may comprise one or more containers. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more containers. The one or more containers may be different, similar, identical, or a combination thereof. Examples of containers include, but are not limited to, plates, microplates, PCR plates, wells, microwells, tubes, Eppendorf tubes, vials, arrays, microarrays, and chips.

The methods disclosed herein may comprise one or more reagents. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more reagents. The one or more reagents may be different, similar, identical, or a combination thereof. The reagents may improve the efficiency of the one or more assays. Reagents may improve the stability of the nucleic acid molecule or variant or derivative thereof. Reagents may include, but are not limited to, enzymes, proteases, nucleases, molecules, polymerases, reverse transcriptases, ligases, and chemical compounds. The methods disclosed herein may comprise conducting an assay comprising one or more antioxidants. Generally, antioxidants are molecules that inhibit oxidation of another molecule. Examples of antioxidants include, but are not limited to, ascorbic acid (e.g., vitamin C), glutathione, lipoic acid, uric acid, carotenes, α-tocopherol (e.g., vitamin E), ubiquinol (e.g., coenzyme Q), and vitamin A.

The methods disclosed herein may comprise one or more buffers or solutions. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more buffers or solutions. The one or more buffers or solutions may be different, similar, identical, or a combination thereof. The buffers or solutions may improve the efficiency of the one or more assays. Buffers or solutions may improve the stability of the nucleic acid molecule or variant or derivative thereof. Buffers or solutions may include, but are not limited to, wash buffers, elution buffers, and hybridization buffers.

The methods disclosed herein may comprise one or more beads, a plurality of beads, or one or more bead sets. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more beads or bead sets. The one or more beads or bead sets may be different, similar, identical, or a combination thereof. The beads may be magnetic, antibody coated, protein A cross-linked, protein G crosslinked, streptavidin coated, oligonucleotide conjugated, silica coated, or a combination thereof. Examples of beads include, but are not limited to, Ampure beads, AMPure XP beads, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, oligo-dT conjugated beads, silica beads, silica-like beads, anti-biotin microbead, anti-fluorochrome microbead, and BcMag™ Carboxy-Terminated Magnetic Beads. In some aspects of the disclosure, the one or more beads comprise one or more Ampure beads. Alternatively, or additionally, the one or more beads comprise AMPure XP beads.

The methods disclosed herein may comprise one or more primers, a plurality of primers, or one or more primer sets. The primers may further comprise one or more linkers. The primers may further comprise or more labels. The primers may be used in one or more assays. For example, the primers are used in one or more sequencing reactions, amplification reactions, or a combination thereof. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more primers or primer sets. The primers may comprise about 100 nucleotides. The primers may comprise between about 10 to about 500 nucleotides, between about 20 to about 450 nucleotides, between about 30 to about 400 nucleotides, between about 40 to about 350 nucleotides, between about 50 to about 300 nucleotides, between about 60 to about 250 nucleotides, between about 70 to about 200 nucleotides, or between about 80 to about 150 nucleotides. In some aspects of the disclosure, the primers comprise between about 80 nucleotides to about 100 nucleotides. The one or more primers or primer sets may be different, similar, identical, or a combination thereof.

The primers may hybridize to at least a portion of the one or more nucleic acid molecules or variant or derivative thereof in the sample or subset of nucleic acid molecules. The primers may hybridize to one or more genomic regions. The primers may hybridize to different, similar, and/or identical genomic regions. The one or more primers may be at least about 50%, 55%, 60%, 65%, 70%, 75%, 80%, 85%, 90%, 95%, 97%, 99% or more complementary to the one or more nucleic acid molecules or variant or derivative thereof.

The primers may comprise one or more nucleotides. The primers may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more nucleotides. The primers may comprise about 100 nucleotides. The primers may comprise between about 10 to about 500 nucleotides, between about 20 to about 450 nucleotides, between about 30 to about 400 nucleotides, between about 40 to about 350 nucleotides, between about 50 to about 300 nucleotides, between about 60 to about 250 nucleotides, between about 70 to about 200 nucleotides, or between about 80 to about 150 nucleotides. In some aspects of the disclosure, the primers comprise between about 80 nucleotides to about 100 nucleotides.

The plurality of primers or the primer sets may comprise two or more primers with identical, similar, and/or different sequences, linkers, and/or labels. For example, two or more primers comprise identical sequences. In another example, two or more primers comprise similar sequences. In yet another example, two or more primers comprise different sequences. The two or more primers may further comprise one or more linkers. The two or more primers may further comprise different linkers. The two or more primers may further comprise similar linkers. The two or more primers may further comprise identical linkers. The two or more primers may further comprise one or more labels. The two or more primers may further comprise different labels. The two or more primers may further comprise similar labels. The two or more primers may further comprise identical labels.

The capture probes, primers, labels, and/or beads may comprise one or more nucleotides. The one or more nucleotides may comprise RNA, DNA, a mix of DNA and RNA residues or their modified analogs such as 2'-OMe, or 2'-fluoro (2'-F), locked nucleic acid (LNA), or abasic sites.

The methods disclosed herein may comprise one or more labels. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more labels. The one or more labels may be different, similar, identical, or a combination thereof.

Examples of labels include, but are not limited to, chemical, biochemical, biological, colorimetric, enzymatic, fluorescent, and luminescent labels, which are well known in the art. The label comprise a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, or a combination thereof.

The label may be a chemical label. Examples of chemical labels can include, but are not limited to, biotin and radiosiotypes (e.g., iodine, carbon, phosphate, hydrogen).

The methods, kits, and compositions disclosed herein may comprise a biological label. The biological labels may comprise metabolic labels, including, but not limited to, bioorthogonal azide-modified amino acids, sugars, and other compounds.

The methods, kits, and compositions disclosed herein may comprise an enzymatic label.

Enzymatic labels can include, but are not limited to horseradish peroxidase (HRP), alkaline phosphatase (AP), glucose oxidase, and β-galactosidase. The enzymatic label may be luciferase.

The methods, kits, and compositions disclosed herein may comprise a fluorescent label. The fluorescent label may be an organic dye (e.g., FITC), biological fluorophore (e.g., green fluorescent protein), or quantum dot. A non-limiting list of fluorescent labels includes fluorescein isothiocyante (FITC), DyLight Fluors, fluorescein, rhodamine (tetramethyl rhodamine isothiocyanate, TRITC), coumarin, Lucifer Yellow, and BODIPY. The label may be a fluorophore. Exemplary fluorophores include, but are not limited to, indocarbocyanine (C3), indodicarbocyanine (C5), Cy3, Cy3.5, Cy5, Cy5.5, Cy7, Texas Red, Pacific Blue, Oregon Green 488, Alexa Fluor®-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX™), LIZ™, VIC™, NED™, PET™, SYBR, PicoGreen, RiboGreen, and the like. The fluorescent label may be a green fluorescent protein (GFP), red fluorescent protein (RFP), yellow fluorescent protein, phycobiliproteins (e.g., allophycocyanin, phycocyanin, phycoerythrin, and phycoerythrocyanin).

The methods disclosed herein may comprise one or more linkers. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more linkers. The one or more linkers may be different, similar, identical, or a combination thereof.

Suitable linkers comprise any chemical or biological compound capable of attaching to a label, primer, and/or capture probe disclosed herein. If the linker attaches to both the label and the primer or capture probe, then a suitable linker would be capable of sufficiently separating the label and the primer or capture probe. Suitable linkers would not significantly interfere with the ability of the primer and/or capture probe to hybridize to a nucleic acid molecule, portion thereof, or variant or derivative thereof. Suitable linkers would not significantly interfere with the ability of the label to be detected. The linker may be rigid. The linker may be flexible. The linker may be semi rigid. The linker may be proteolytically stable (e.g., resistant to proteolytic cleavage). The linker may be proteolytically unstable (e.g., sensitive to proteolytic cleavage). The linker may be helical. The linker may be non-helical. The linker may be coiled. The linker may be β-stranded. The linker may comprise a turn conformation. The linker may be a single chain. The linker may be a long chain. The linker may be a short chain. The linker may comprise at least about 5 residues, at least about 10 residues, at least about 15 residues, at least about 20 residues, at least about 25 residues, at least about 30 residues, or at least about 40 residues or more.

Examples of linkers include, but are not limited to, hydrazone, disulfide, thioether, and peptide linkers. The linker may be a peptide linker. The peptide linker may comprise a proline residue. The peptide linker may comprise an arginine, phenyladenine, threonine, glutamine, glutamate, or any combination thereof. The linker may be a heterobifunctional crosslinker.

The methods disclosed herein may comprise conducting 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, or 50 or more assays on a sample comprising one or more nucleic acid molecules. The two or more assays may be different, similar, identical, or a combination thereof. For example, the methods disclosed herein comprise conducting two or more sequencing reactions. In another example, the methods disclosed herein comprise conducting two or more assays, wherein at least one of the two or more assays comprises a sequencing reaction. In yet another example, the methods disclosed herein comprise conducting two or more assays, wherein at least two of the two or more assays comprises a sequencing reaction and a hybridization reaction. The two or more assays may be performed sequentially, simultaneously, or a combination thereof. For example, the two or more sequencing reactions may be performed simultaneously. In another example, the methods disclosed herein comprise conducting a hybridization reaction, followed by a sequencing reaction. In yet another example, the methods disclosed herein comprise conducting two or more hybridization reactions simultaneously, followed by conducting two or more sequencing reactions simultaneously. The two or more assays may be performed by one or more devices. For example, two or more amplification reactions may be performed by a PCR machine. In another example, two or more sequencing reactions may be performed by two or more sequencers.

Devices

The methods disclosed herein may comprise one or more devices. The methods disclosed herein may comprise one or more assays comprising one or more devices. The methods disclosed herein may comprise the use of one or more devices to perform one or more steps or assays. The methods disclosed herein may comprise the use of one or more devices in one or more steps or assays. For example, conducting a sequencing reaction may comprise one or more sequencers. In another example, producing a subset of nucleic acid molecules may comprise the use of one or more magnetic separators. In yet another example, one or more processors may be used in the analysis of one or more nucleic acid samples. Exemplary devices include, but are not limited to, sequencers, thermocyclers, real-time PCR instruments, magnetic separators, transmission devices, hybridization chambers, electrophoresis apparatus, centrifuges, microscopes, imagers, fluorometers, luminometers, plate readers, computers, processors, and bioanalyzers.

The methods disclosed herein may comprise one or more sequencers. The one or more sequencers may comprise one or more HiSeq, MiSeq, HiScan, Genome Analyzer IIx, SOLiD Sequencer, Ion Torrent PGM, 454 GS Junior, Pac Bio RS, or a combination thereof. The one or more sequencers may comprise one or more sequencing platforms. The one or more sequencing platforms may comprise GS FLX by 454 Life Technologies/Roche, Genome Analyzer by Solexa/Illumina, SOLiD by Applied Biosystems, CGA Platform by Complete Genomics, PacBio RS by Pacific Biosciences, or a combination thereof.

The methods disclosed herein may comprise one or more thermocyclers. The one or more thermocyclers may be used to amplify one or more nucleic acid molecules. The methods disclosed herein may comprise one or more real-time PCR instruments. The one or more real-time PCR instruments may comprise a thermal cycler and a fluorimeter. The one or more thermocyclers may be used to amplify and detect one or more nucleic acid molecules.

The methods disclosed herein may comprise one or more magnetic separators. The one or more magnetic separators may be used for separation of paramagnetic and ferromagnetic particles from a suspension. The one or more magnetic separators may comprise one or more LifeStep™ biomagnetic separators, SPHERO™ FlexiMag separator, SPHERO™ MicroMag separator, SPHERO™ HandiMag separator, SPHERO™ MiniTube Mag separator, SPHERO™ UltraMag separator, DynaMag™ magnet, DynaMag™-2 Magnet, or a combination thereof.

The methods disclosed herein may comprise one or more bioanalyzers. Generaly, a bioanalyzer is a chip-based capillary electrophoresis machine that can analyse RNA, DNA, and proteins. The one or more bioanalyzers may comprise Agilent's 2100 Bioanalyzer.

The methods disclosed herein may comprise one or more processors. The one or more processors may analyze, compile, store, sort, combine, assess or otherwise process one or more data and/or results from one or more assays, one or more data and/or results based on or derived from one or more assays, one or more outputs from one or more assays, one or more outputs based on or derived from one or more assays, one or more outputs from one or data and/or results, one or more outputs based on or derived from one or more data and/or results, or a combination thereof. The one or more processors may transmit the one or more data, results, or outputs from one or more assays, one or more data, results, or outputs based on or derived from one or more assays, one or more outputs from one or more data or results, one or more outputs based on or derived from one or more data or results, or a combination thereof. The one or more processors may receive and/or store requests from a user. The one or more processors may produce or generate one or more data, results, outputs. The one or more processors may produce or generate one or more biomedical reports. The one or more processors may transmit one or more biomedical reports. The one or more processors may analyze, compile, store, sort, combine, assess or otherwise process information from one or more databases, one or more data or results, one or more outputs, or a combination thereof. The one or more processors may analyze, compile, store, sort, combine, assess or otherwise process information from 1, 2, 3, 4, 5, 6, 7, 8, 9, 10, 11, 12, 13, 14, 15, 16, 17, 18, 19, 20, 30 or more databases. The one or more processors may transmit one or more requests, data, results, outputs and/or information to one or more users, processors, computers, computer systems, memory locations, devices, databases, or a combination thereof. The one or more processors may receive one or more requests, data, results, outputs and/or information from one or more users, processors, computers, computer systems, memory locations, devices, databases or a combination thereof. The one or more processors may retrieve one or more requests, data, results, outputs and/or information from one or more users, processors, computers, computer systems, memory locations, devices, databases or a combination thereof.

The methods disclosed herein may comprise one or more memory locations. The one or more memory locations may store information, data, results, outputs, requests, or a combination thereof. The one or more memory locations may receive information, data, results, outputs, requests, or a combination thereof from one or more users, processors, computers, computer systems, devices, or a combination thereof.

Methods described herein can be implemented with the aid of one or more computers and/or computer systems. A computer or computer system may comprise electronic storage locations (e.g., databases, memory) with machine-executable code for implementing the methods provided herein, and one or more processors for executing the machine-executable code.

Reference will now be made to the figures. It will be appreciated that the figures and features therein are not necessarily drawn to scale.

FIG. 1 shows a computer system (also "system" herein) 101 programmed or otherwise configured for implementing the methods of the disclosure, such as nucleic acid processing and/or analysis, and/or data analysis. The system 101 includes a central processing unit (CPU, also "processor" and "computer processor" herein) 105, which can be a single core or multi core processor, or a plurality of processors for parallel processing. The system 101 also includes memory 110 (e.g., random-access memory, read-only memory, flash memory), electronic storage unit 115 (e.g., hard disk), communications interface 120 (e.g., network adapter) for communicating with one or more other systems, and peripheral devices 125, such as cache, other memory, data storage and/or electronic display adapters. The memory 110, storage unit 115, interface 120 and peripheral devices 125 are in communication with the CPU 105 through a communications bus (solid lines), such as a motherboard. The storage unit 115 can be a data storage unit (or data repository) for storing data. The system 101 is operatively coupled to a computer network ("network") 130 with the aid of the communications interface 120. The network 130 can be the Internet, an internet and/or extranet, or an intranet and/or extranet that is in communication with the Internet. The network 130 in some cases is a telecommunication and/or data network. The network 130 can include one or more computer servers, which can enable distributed computing, such as cloud computing. The network 130 in some cases, with the aid of the system 101, can implement a peer-to-peer network, which may enable devices coupled to the system 101 to behave as a client or a server.

The system 101 is in communication with a processing system 135. The processing system 135 can be configured to implement the methods disclosed herein. In some examples, the processing system 135 is a nucleic acid sequencing system, such as, for example, a next generation sequencing system (e.g., Illumina sequencer, Ion Torrent sequencer, Pacific Biosciences sequencer). The processing system 135 can be in communication with the system 101 through the network 130, or by direct (e.g., wired, wireless) connection. The processing system 135 can be configured for analysis, such as nucleic acid sequence analysis.

Methods as described herein can be implemented by way of machine (or computer processor) executable code (or software) stored on an electronic storage location of the system 101, such as, for example, on the memory 110 or electronic storage unit 115. During use, the code can be executed by the processor 105. In some examples, the code can be retrieved from the storage unit 115 and stored on the memory 110 for ready access by the processor 105. In some situations, the electronic storage unit 115 can be precluded, and machine-executable instructions are stored on memory 110.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the system 1601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The one or more computers and/or computer systems may analyze, compile, store, sort, combine, assess or otherwise process one or more data and/or results from one or more assays, one or more data and/or results based on or derived from one or more assays, one or more outputs from one or more assays, one or more outputs based on or derived from one or more assays, one or more outputs from one or data and/or results, one or more outputs based on or derived from one or more data and/or results, or a combination thereof. The one or more computers and/or computer systems may transmit the one or more data, results, or outputs from one or more assays, one or more data, results, or outputs based on or derived from one or more assays, one or more outputs from one or more data or results, one or more outputs based on or derived from one or more data or results, or a combination thereof. The one or more computers and/or computer systems may receive and/or store requests from a user. The one or more computers and/or computer systems may produce or generate one or more data, results, outputs. The one or more computers and/or computer systems may produce or generate one or more biomedical reports. The one or more computers and/or computer systems may transmit one or more biomedical reports. The one or more computers and/or computer systems may analyze, compile, store, sort, combine, assess or otherwise process information from one or more databases, one or more data or results, one or more outputs, or a combination thereof. The one or more computers and/or computer systems may analyze, compile, store, sort, combine, assess or otherwise process information from 1, 2, 3, 4, 5, 6, 7, 8, 9, 10, 11, 12, 13, 14, 15, 16, 17, 18, 19, 20, 30 or more databases. The one or more computers and/or computer systems may transmit one or more requests, data, results, outputs, and/or information to one or more users, processors, computers, computer systems, memory locations, devices, or a combination thereof. The one or more computers and/or computer systems may receive one or more requests, data, results, outputs, and/or information from one or more users, processors, computers, computer systems, memory locations, devices, or a combination thereof. The one or more computers and/or computer systems may retrieve one or more requests, data, results, outputs and/or information from one or more users, processors, computers, computer systems, memory locations, devices, databases or a combination thereof.

The methods disclosed herein may comprise one or more transmission devices comprising an output means for transmitting one or more data, results, outputs, information, biomedical outputs, and/or biomedical reports. The output means can take any form which transmits the data, results, requests, and/or information and may comprise a monitor, printed format, printer, computer, processor, memory location, or a combination thereof. The transmission device may comprise one or more processors, computers, and/or computer systems for transmitting information.

Databases

The methods disclosed herein may comprise one or more databases. The methods disclosed herein may comprise at least about 1, 2, 3, 4, 5, 6, 7, 8, 9, 10, 11, 12, 13, 14, 15, 16, 17, 18, 19, 20, 30 or more databases. The databases may comprise genomic, proteomic, pharmacogenomic, biomedical, and scientific databases. The databases may be publicly available databases. Alternatively, or additionally, the databases may comprise proprietary databases. The databases may be commercially available databases. The databases include, but are not limited to, MendelDB, PharmGKB, Varimed, Regulome, curated BreakSeq junctions, Online Mendelian Inheritance in Man (OMIM), Human Genome Mutation Database (HGMD), NCBI dbSNP, NCBI RefSeq, GENCODE, GO (gene ontology), and Kyoto Encyclopedia of Genes and Genomes (KEGG).

The methods disclosed herein may comprise analyzing one or more databases. The methods disclosed herein may comprise analyzing at least about 1, 2, 3, 4, 5, 6, 7, 8, 9, 10, 11, 12, 13, 14, 15, 16, 17, 18, 19, 20, 30 or more databases. Analyzing the one or more databases may comprise one or more algorithms, computers, processors, memory locations, devices, or a combination thereof.

The methods disclosed herein may comprise producing one or more probes based on data and/or information from one or more databases. The methods disclosed herein may comprise producing one or more probe sets based on data and/or information from one or more databases. The methods disclosed herein may comprise producing one or more probes and/or probe sets based on data and/or information from at least about 2 or more databases. The methods disclosed herein may comprise producing one or more probes and/or probe sets based on data and/or information from at least about 3 or more databases. The methods disclosed herein may comprise producing one or more probes and/or probe sets based on data and/or information from at least about 4, 5, 6, 7, 8, 9, 10, 11, 12, 13, 14, 15, 16, 17, 18, 19, 20, 30 or more databases.

The methods disclosed herein may comprise identifying one or more nucleic acid regions based on data and/or information from one or more databases. The methods disclosed herein may comprise identifying one or more sets of nucleic acid regions based on data and/or information from one or more databases. The methods disclosed herein may comprise identifying one or more nucleic acid regions and/or sets of nucleic acid regions based on data and/or information from at least about 2 or more databases. The methods disclosed herein may comprise identifying one or more nucleic acid regions and/or sets of nucleic acid regions based on data and/or information from at least about 3 or more databases. The methods disclosed herein may comprise identifying one or more nucleic acid regions and/or sets of nucleic acid regions based on data and/or information from at least about 4, 5, 6, 7, 8, 9, 10, 11, 12, 13, 14, 15, 16, 17, 18, 19, 20, 30 or more databases. The methods disclosed herein may further comprise producing one or more probes and/or probe sets based on the identification of the one or more nucleic acid regions and/or sets of nucleic acid regions.

The methods disclosed herein may comprise analyzing one or more results based on data and/or information from one or more databases. The methods disclosed herein may comprise analyzing one or more sets of results based on data and/or information from one or more databases. The methods disclosed herein may comprise analyzing one or more combined results based on data and/or information from one or more databases. The methods disclosed herein may comprise analyzing one or more results, sets of results, and/or combined results based on data and/or information from at least about 2 or more databases. The methods disclosed herein may comprise analyzing one or more results, sets of results, and/or combined results based on data and/or information from at least about 3 or more databases. The methods disclosed herein may comprise analyzing one or more results, sets of results, and/or combined results based on data and/or information from at least about 4, 5, 6, 7, 8, 9, 10, 11, 12, 13, 14, 15, 16, 17, 18, 19, 20, 30 or more databases.

The methods disclosed herein may comprise comparing one or more results based on data and/or information from one or more databases. The methods disclosed herein may comprise comparing one or more sets of results based on data and/or information from one or more databases. The methods disclosed herein may comprise comparing one or more combined results based on data and/or information from one or more databases. The methods disclosed herein may comprise comparing one or more results, sets of results, and/or combined results based on data and/or information from at least about 2 or more databases. The methods disclosed herein may comprise comparing one or more results, sets of results, and/or combined results based on data and/or information from at least about 3 or more databases. The methods disclosed herein may comprise comparing one or more results, sets of results, and/or combined results based on data and/or information from at least about 4, 5, 6, 7, 8, 9, 10, 11, 12, 13, 14, 15, 16, 17, 18, 19, 20, 30 or more databases.

The methods disclosed herein may comprise biomedical databases, genomic databases, biomedical reports, disease reports, case-control analysis, and rare variant discovery analysis based on data and/or information from one or more databases, one or more assays, one or more data or results, one or more outputs based on or derived from one or more assays, one or more outputs based on or derived from one or more data or results, or a combination thereof.

Analysis

The methods disclosed herein may comprise one or more data, one or more data sets, one or more combined data, one or more combined data sets, one or more results, one or more sets of results, one or more combined results, or a combination thereof. The data and/or results may be based on or derived from one or more assays, one or more databases, or a combination thereof. The methods disclosed herein may comprise analysis of the one or more data, one or more data sets, one or more combined data, one or more combined data sets, one or more results, one or more sets of results, one or more combined results, or a combination thereof. The methods disclosed herein may comprise processing of the one or more data, one or more data sets, one or more combined data, one or more combined data sets, one or more results, one or more sets of results, one or more combined results, or a combination thereof.

The methods disclosed herein may comprise at least one analysis and at least one processing of the one or more data, one or more data sets, one or more combined data, one or more combined data sets, one or more results, one or more sets of results, one or more combined results, or a combination thereof. The methods disclosed herein may comprise one or more analyses and one or more processing of the one or more data, one or more data sets, one or more combined data, one or more combined data sets, one or more results, one or more sets of results, one or more combined results, or a combination thereof. The methods disclosed herein may comprise at least 1, 2, 3, 4, 5, 6, 7, 8, 9, 10, 15, 20, 30, 40, 50, 60, 70, 80, 90, 100, 200, 300, 400, 500, 600, 700, 800, 900, 1000 or more distinct analyses of the one or more data, one or more data sets, one or more combined data, one or more combined data sets, one or more results, one or more sets of results, one or more combined results, or a combination thereof. The methods disclosed herein may comprise at least 1, 2, 3, 4, 5, 6, 7, 8, 9, 10, 15, 20, 30, 40, 50, 60, 70, 80, 90, 100, 200, 300, 400, 500, 600, 700, 800, 900, 1000 or more distinct processing of the one or more data, one or more data sets, one or more combined data, one or more combined data sets, one or more results, one or more sets of results, one or more combined results, or a combination thereof. The one or more analyses and/or one or more processing may occur simultaneously, sequentially, or a combination thereof.

The one or more analyses and/or one or more processing may occur over 1, 2, 3, 4, 5, 6, 7, 8, 9, 10, 11, 12, 15, 20, 30, 40, 50, 60, 70, 80, 90, 100, 200, 300, 400, 500, 600, 700, 800, 900, 1000 or time points. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more hour period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more day period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more week period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more month period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more year period.

The methods disclosed herein may comprise one or more data. The one or more data may comprise one or more raw data based on or derived from one or more assays. The one or more data may comprise one or more raw data based on or derived from one or more databases. The one or more data may comprise at least partially analyzed data based on or derived from one or more raw data. The one or more data may comprise at least partially processed data based on or derived from one or more raw data. The one or more data may comprise fully analyzed data based on or derived from one or more raw data. The one or more data may comprise fully processed data based on or derived from one or more raw data. The data may comprise sequencing read data or expression data. The data may comprise biomedical, scientific, pharmacological, and/or genetic information.

The methods disclosed herein may comprise one or more combined data. The one or more combined data may comprise two or more data. The one or more combined data may comprise two or more data sets. The one or more combined data may comprise one or more raw data based on or derived from one or more assays. The one or more combined data may comprise one or more raw data based on or derived from one or more databases. The one or more combined data may comprise at least partially analyzed data based on or derived from one or more raw data. The one or more combined data may comprise at least partially processed data based on or derived from one or more raw data. The one or more combined data may comprise fully analyzed data based on or derived from one or more raw data. The one or more combined data may comprise fully processed data based on or derived from one or more raw data. One or more combined data may comprise sequencing read data or expression data. One or more combined data may comprise biomedical, scientific, pharmacological, and/or genetic information.

The methods disclosed herein may comprise one or more data sets. The one or more data sets may comprise one or more data. The one or more data sets may comprise one or more combined data. The one or more data sets may comprise one or more raw data based on or derived from one or more assays. The one or more data sets may comprise one or more raw data based on or derived from one or more databases. The one or more data sets may comprise at least partially analyzed data based on or derived from one or more raw data. The one or more data sets may comprise at least partially processed data based on or derived from one or more raw data. The one or more data sets may comprise fully analyzed data based on or derived from one or more raw data. The one or more data sets may comprise fully processed data based on or derived from one or more raw data. The data sets may comprise sequencing read data or expression data. The data sets may comprise biomedical, scientific, pharmacological, and/or genetic information.

The methods disclosed herein may comprise one or more combined data sets. The one or more combined data sets may comprise two or more data. The one or more combined data sets may comprise two or more combined data. The one or more combined data sets may comprise two or more data sets. The one or more combined data sets may comprise one or more raw data based on or derived from one or more assays. The one or more combined data sets may comprise one or more raw data based on or derived from one or more databases. The one or more combined data sets may comprise at least partially analyzed data based on or derived from one or more raw data. The one or more combined data sets may comprise at least partially processed data based on or derived from one or more raw data. The one or more combined data sets may comprise fully analyzed data based on or derived from one or more raw data. The one or more combined data sets may comprise fully processed data based on or derived from one or more raw data. The methods disclosed herein may further comprise further processing and/or analysis of the combined data sets. One or more combined data sets may comprise sequencing read data or expression data. One or more combined data sets may comprise biomedical, scientific, pharmacological, and/or genetic information.

The methods disclosed herein may comprise one or more results. The one or more results may comprise one or more data, data sets, combined data, and/or combined data sets. The one or more results may be based on or derived from one or more data, data sets, combined data, and/or combined data sets. The one or more results may be produced from one or more assays. The one or more results may be based on or derived from one or more assays. The one or more results may be based on or derived from one or more databases. The one or more results may comprise at least partially analyzed results based on or derived from one or more data, data sets, combined data, and/or combined data sets. The one or more results may comprise at least partially processed results based on or derived from one or more data, data sets, combined data, and/or combined data sets. The one or more results may comprise at fully analyzed results based on or derived from one or more data, data sets, combined data, and/or combined data sets. The one or more results may comprise fully processed results based on or derived from one or more data, data sets, combined data, and/or combined data sets. The results may comprise sequencing read data or expression data. The results may comprise biomedical, scientific, pharmacological, and/or genetic information.

The methods disclosed herein may comprise one or more sets of results. The one or more sets of results may comprise one or more data, data sets, combined data, and/or combined data sets. The one or more sets of results may be based on or derived from one or more data, data sets, combined data, and/or combined data sets. The one or more sets of results may be produced from one or more assays. The one or more sets of results may be based on or derived from one or more assays. The one or more sets of results may be based on or derived from one or more databases. The one or more sets of results may comprise at least partially analyzed sets of results based on or derived from one or more data, data sets, combined data, and/or combined data sets. The one or more sets of results may comprise at least partially processed sets of results based on or derived from one or more data, data sets, combined data, and/or combined data sets. The one or more sets of results may comprise at fully analyzed sets of results based on or derived from one or more data, data sets, combined data, and/or combined data sets. The one or more sets of results may comprise fully processed sets of results based on or derived from one or more data, data sets, combined data, and/or combined data sets. The sets of results may comprise sequencing read data or expression data. The sets of results may comprise biomedical, scientific, pharmacological, and/or genetic information.

The methods disclosed herein may comprise one or more combined results. The combined results may comprise one or more results, sets of results, and/or combined sets of results. The combined results may be based on or derived from one or more results, sets of results, and/or combined sets of results. The one or more combined results may comprise one or more data, data sets, combined data, and/or combined data sets. The one or more combined results may be based on or derived from one or more data, data sets, combined data, and/or combined data sets. The one or more combined results may be produced from one or more assays. The one or more combined results may be based on or derived from one or more assays. The one or more combined results may be based on or derived from one or more databases. The one or more combined results may comprise at least partially analyzed combined results based on or derived from one or more data, data sets, combined data, and/or combined data sets. The one or more combined results may comprise at least partially processed combined results based on or derived from one or more data, data sets, combined data, and/or combined data sets. The one or more combined results may comprise at fully analyzed combined results based on or derived from one or more data, data sets, combined data, and/or combined data sets. The one or more combined results may comprise fully processed combined results based on or derived from one or more data, data sets, combined data, and/or combined data sets. The combined results may comprise sequencing read data or expression data. The combined results may comprise biomedical, scientific, pharmacological, and/or genetic information.

The methods disclosed herein may comprise one or more combined sets of results. The combined sets of results may comprise one or more results, sets of results, and/or combined results. The combined sets of results may be based on or derived from one or more results, sets of results, and/or combined results. The one or more combined sets of results may comprise one or more data, data sets, combined data, and/or combined data sets. The one or more combined sets of results may be based on or derived from one or more data, data sets, combined data, and/or combined data sets. The one or more combined sets of results may be produced from one or more assays. The one or more combined sets of results may be based on or derived from one or more assays. The one or more combined sets of results may be based on or derived from one or more databases. The one or more combined sets of results may comprise at least partially analyzed combined sets of results based on or derived from one or more data, data sets, combined data, and/or combined data sets. The one or more combined sets of results may comprise at least partially processed combined sets of results based on or derived from one or more data, data sets, combined data, and/or combined data sets. The one or more combined sets of results may comprise at fully analyzed combined sets of results based on or derived from one or more data, data sets, combined data, and/or combined data sets. The one or more combined sets of results may comprise fully processed combined sets of results based on or derived from one or more data, data sets, combined data, and/or combined data sets. The combined sets of results may comprise sequencing read data or expression data. The combined sets of results may comprise biomedical, scientific, pharmacological, and/or genetic information.

The methods disclosed herein may comprise one or more outputs, sets of outputs, combined outputs, and/or combined sets of outputs. The methods, libraries, kits and systems herein may comprise producing one or more outputs, sets of outputs, combined outputs, and/or combined sets of outputs. The sets of outputs may comprise one or more outputs, one or more combined outputs, or a combination thereof. The combined outputs may comprise one or more outputs, one or more sets of outputs, one or more combined sets of outputs, or a combination thereof. The combined sets of outputs may comprise one or more outputs, one or more sets of outputs, one or more combined outputs, or a combination thereof. The one or more outputs, sets of outputs, combined outputs, and/or combined sets of outputs may be based on or derived from one or more data, one or more data sets, one or more combined data, one or more combined data sets, one or more results, one or more sets of results, one or more combined results, or a combination thereof. The one or more outputs, sets of outputs, combined outputs, and/or combined sets of outputs may be based on or derived from one or more databases. The one or more outputs, sets of outputs, combined outputs, and/or combined sets of outputs may comprise one or more biomedical reports, biomedical outputs, rare variant outputs, pharmacogenetic outputs, population study outputs, case-control outputs, biomedical databases, genomic databases, disease databases, net content.

The methods disclosed herein may comprise one or more biomedical outputs, one or more sets of biomedical outputs, one or more combined biomedical outputs, one or more combined sets of biomedical outputs. The methods, libraries, kits and systems herein may comprise producing one or more biomedical outputs, one or more sets of biomedical outputs, one or more combined biomedical outputs, one or more combined sets of biomedical outputs. The sets of biomedical outputs may comprise one or more biomedical outputs, one or more combined biomedical outputs, or a combination thereof. The combined biomedical outputs may comprise one or more biomedical outputs, one or more sets of biomedical outputs, one or more combined sets of biomedical outputs, or a combination thereof. The combined sets of biomedical outputs may comprise one or more biomedical outputs, one or more sets of biomedical outputs, one or more combined biomedical outputs, or a combination thereof. The one or more biomedical outputs, one or more sets of biomedical outputs, one or more combined biomedical outputs, one or more combined sets of biomedical outputs may be based on or derived from one or more data, one or more data sets, one or more combined data, one or more combined data sets, one or more results, one or more sets of results, one or more combined results, one or more outputs, one or more sets of outputs, one or more combined outputs, one or more sets of combined outputs, or a combination thereof. The one or more biomedical outputs may comprise biomedical biomedical information of a subject. The biomedical biomedical information of the subject may predict, diagnose, and/or prognose one or more biomedical features. The one or more biomedical features may comprise the status of a disease or condition, genetic risk of a disease or condition, reproductive risk, genetic risk to a fetus, risk of an adverse drug reaction, efficacy of a drug therapy, prediction of optimal drug dosage, transplant tolerance, or a combination thereof.

The methods disclosed herein may comprise one or more biomedical reports. The methods, libraries, kits and systems herein may comprise producing one or more biomedical reports. The one or more biomedical reports may be based on or derived from one or more data, one or more data sets, one or more combined data, one or more combined data sets, one or more results, one or more sets of results, one or more combined results, one or more outputs, one or more sets of outputs, one or more combined outputs, one or more sets of combined outputs, one or more biomedical outputs, one or more sets of biomedical outputs, combined biomedical outputs, one or more sets of biomedical outputs, or a combination thereof. The biomedical report may predict, diagnose, and/or prognose one or more biomedical features. The one or more biomedical features may comprise the status of a disease or condition, genetic risk of a disease or condition, reproductive risk, genetic risk to a fetus, risk of an adverse drug reaction, efficacy of a drug therapy, prediction of optimal drug dosage, transplant tolerance, or a combination thereof.

The methods disclosed herein may also comprise the transmission of one or more data, information, results, outputs, reports or a combination thereof. For example, data/information based on or derived from the one or more assays are transmitted to another device and/or instrument. In another example, the data, results, outputs, biomedical outputs, biomedical reports, or a combination thereof are transmitted to another device and/or instrument. The information obtained from an algorithm may also be transmitted to another device and/or instrument. Information based on the analysis of one or more databases may be transmitted to another device and/or instrument. Transmission of the data/information may comprise the transfer of data/information from a first source to a second source. The first and second sources may be in the same approximate location (e.g., within the same room, building, block, campus). Alternatively, first and second sources may be in multiple locations (e.g., multiple cities, states, countries, continents, etc). The data, results, outputs, biomedical outputs, biomedical reports can be transmitted to a patient and/or a healthcare provider.

Transmission may be based on the analysis of one or more data, results, information, databases, outputs, reports, or a combination thereof. For example, transmission of a second report is based on the analysis of a first report. Alternatively, transmission of a report is based on the analysis of one or more data or results. Transmission may be based on receiving one or more requests. For example, transmission of a report may be based on receiving a request from a user (e.g., patient, healthcare provider, individual).

Transmission of the data/information may comprise digital transmission or analog transmission. Digital transmission may comprise the physical transfer of data (a digital bit stream) over a point-to-point or point-to-multipoint communication channel Examples of such channels are copper wires, optical fibres, wireless communication channels, and storage media. The data may be represented as an electromagnetic signal, such as an electrical voltage, radiowave, microwave, or infrared signal.

Analog transmission may comprise the transfer of a continuously varying analog signal. The messages can either be represented by a sequence of pulses by means of a line code (baseband transmission), or by a limited set of continuously varying wave forms (passband transmission), using a digital modulation method. The passband modulation and corresponding demodulation (also known as detection) can be carried out by modem equipment. According to the most common definition of digital signal, both baseband and passband signals representing bit-streams are considered as digital transmission, while an alternative definition only considers the baseband signal as digital, and passband transmission of digital data as a form of digital-to-analog conversion.

The methods disclosed herein may comprise one or more sample identifiers. The sample identifiers may comprise labels, barcodes, and other indicators which can be linked to one or more samples and/or subsets of nucleic acid molecules. The methods disclosed herein may comprise one or more processors, one or more memory locations, one or more computers, one or more monitors, one or more computer software, one or more algorithms for linking data, results, outputs, biomedical outputs, and/or biomedical reports to a sample.

The methods disclosed herein may comprise a processor for correlating the expression levels of one or more nucleic acid molecules with a prognosis of disease outcome. The methods disclosed herein may comprise one or more of a variety of correlative techniques, including lookup tables, algorithms, multivariate models, and linear or nonlinear combinations of expression models or algorithms. The expression levels may be converted to one or more likelihood scores, reflecting a likelihood that the patient providing the sample may exhibit a particular disease outcome. The models and/or algorithms can be provided in machine readable format and can optionally further designate a treatment modality for a patient or class of patients.

Diseases or Conditions

The methods disclosed herein may comprise predicting, diagnosing, and/or prognosing a status or outcome of a disease or condition in a subject based on one or more biomedical outputs. Predicting, diagnosing, and/or prognosing a status or outcome of a disease in a subject may comprise diagnosing a disease or condition, identifying a disease or condition, determining the stage of a disease or condition, assessing the risk of a disease or condition, assessing the risk of disease recurrence, assessing reproductive risk, assessing genetic risk to a fetus, assessing the efficacy of a drug, assessing risk of an adverse drug reaction, predicting optimal drug dosage, predicting drug resistance, or a combination thereof.

The samples disclosed herein may be from a subject suffering from a cancer. The sample may comprise malignant tissue, benign tissue, or a mixture thereof. The cancer may be a recurrent and/or refractory cancer. Examples of cancers include, but are not limited to, sarcomas, carcinomas, lymphomas or leukemias.

Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. The cancer may be a skin cancer, such as a basal cell carcinoma, squamous, melanoma, nonmelanoma, or actinic (solar) keratosis.

The cancer may be a lung cancer. Lung cancer can start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. The cancer may be a meningioma.

The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic leukemia.

Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenstrom macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Additional diseases and/or conditions include, but are not limited to, atherosclerosis, inflammatory diseases, autoimmune diseases, rheumatic heart disease. Examples of inflammatory diseases include, but are not limited to, acne vulgaris, Alzheimer's, ankylosing spondylitis, arthritis (osteoarthritis, rheumatoid arthritis (RA), psoriatic arthritis), asthma, atherosclerosis, celiac disease, chronic prostatitis, Crohn's disease, colitis, dermatitis, diverticulitis, fibromyalgia, glomeruionephritis, hepatitis, irritable bowel syndrome (IBS), systemic lupus erythematous (SLE), nephritis, Parkinson's disease, pelvic inflammatory disease, sarcoidosis, ulcerative colitis, and vasculitis.

Examples of autoimmune diseases include, but are not limited to, acute disseminated encephalomyelitis (ADEM), Addison's disease, agammaglobulinemia, alopecia areata, amyotrophic Lateral Sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behçet's disease, Berger's disease, Bickerstaff s encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's diseasevDercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritisvepidermolysis bullosa acquisita, erythema nodosum, erythroblastosis fetalis, essential mixed cryoglobulinemia, Evan's syndrome, fibrodysplasia ossificans progressiva, fibrosing alveolitis (or idiopathic pulmonary fibrosis), gastritis, gastrointestinal pemphigoid, giant cell arteritis, glomerulonephritis, Goodpasture's syndrome, Graves' disease, Guillain-Barré syndrome (GBS), Hashimoto's encephalopathy, Hashimoto's thyroiditisvHenoch-Schonlein purpuravherpes gestationis aka gestational pemphigoid, hidradenitis suppurativa, Hughes-Stovin syndrome, hypogammaglobulinemia, idiopathic inflammatory demyelinating diseases, idiopathic pulmonary fibrosis, IgA nephropathy, inclusion body myositis, chronic inflammatory demyelinating polyneuropathyvinterstitial cystitis, juvenile idiopathic arthritis aka juvenile rheumatoid arthritis, Kawasaki's disease, Lambert-Eaton myasthenic syndrome, leukocytoclastic vasculitis, Lichen planus, Lichen sclerosus, linear IgA disease (LAD), Lou Gehrig's disease (Also Amyotrophic lateral sclerosis), lupoid hepatitis aka autoimmune hepatitis, lupus erythematosus, Majeed syndrome, Meniere's disease, microscopic polyangiitis, mixed connective tissue disease, morphea, Mucha-Habermann disease, multiple sclerosis, myasthenia gravis, myositis, neuromyelitis optica (also Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with *streptococcus*), paraneoplastic cerebellar degeneration, paroxysmal nocturnal hemoglobinuria (PNH), Parry Romberg syndrome, Parsonage-Turner syndrome, Pars planitis, pemphigus vulgaris, pernicious anaemia, perivenous encephalomyelitis, POEMS syndrome, polyarteritis *nodosa*, polymyalgia rheumatica, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, Schmidt syndrome another form of APS, Schnitzler syndrome, scleritis, scleroderma, serum sickness, Sjögren's syndrome, spondyloarthropathy, Stiff person syndrome, subacute bacterial endocarditis (SBE), Susac's syndrome, Sweet's syndrome, sympathetic ophthalmia, Takayasu's arteritis, temporal arteritis (also known as "giant cell arteritis"), thrombocytopenia, Tolosa-Hunt syndrome, transverse myelitis, ulcerative colitis, undifferentiated connective tissue disease different from mixed connective tissue disease, undifferentiated spondyloarthropathy, urticarial vasculitis, vasculitis, vitiligo, and Wegener's granulomatosis.

The methods provided herein may also be useful for detecting, monitoring, diagnosing and/or predicting a subject's response to an implanted device. Exemplary medical devices include but are not limited to stents, replacement heart valves, implanted cerebella stimulators, hip replacement joints, breast implants, and knee implants.

The methods disclosed herein may be used for monitoring the health of a fetus using whole or partial genome analysis of nucleic acids derived from a fetus, as compared to the maternal genome. For example, nucleic acids can be useful in pregnant subjects for fetal diagnostics, with fetal nucleic acids serving as a marker for gender, rhesus D status, fetal aneuploidy, and sex-linked disorders. The methods disclosed herein may identify fetal mutations or genetic abnormalities. The methods disclosed herein can enable detection of extra or missing chromosomes, particularly those typically associated with birth defects or miscarriage. The methods disclosed herein may comprise the diagnosis, prediction or monitoring of autosomal trisomies (e.g., Trisomy 13, 15, 16, 18, 21, or 22) may be based on the detection of foreign molecules. The trisomy may be associated with an increased chance of miscarriage (e.g., Trisomy 15, 16, or 22). Alternatively, the trisomy that is detected is a liveborn trisomy that may indicate that an infant will be born with birth defects (e.g., Trisomy 13 (Patau Syndrome), Trisomy 18 (Edwards Syndrome), and Trisomy 21 (Down Syndrome)). The abnormality may also be of a sex chromosome (e.g., XXY (Klinefelter's Syndrome), XYY (Jacobs Syndrome), or XXX (Trisomy X). The methods disclosed herein may comprise one or more genomic regions on the following chromosomes: 13, 18, 21, X, or Y. For example, the foreign molecule may be on chromosome 21 and/or on chromosome 18, and/or on chromosome 13. The one or more genomic regions may comprise multiple sites on multiple chromosomes.

Further fetal conditions that can be determined based on the methods and systems herein include monosomy of one or more chromosomes (X chromosome monosomy, also known as Turner's syndrome), trisomy of one or more chromosomes (13, 18, 21, and X), tetrasomy and pentasomy of one or more chromosomes (which in humans is most commonly observed in the sex chromosomes, e.g. XXXX, XXYY, XXXY, XYYY, XXXXX, XXXXY, XXXXY, XYYYY and XXYYY), monoploidy, triploidy (three of every chromosome, e.g. 69 chromosomes in humans), tetraploidy (four of every chromosome, e.g. 92 chromosomes in humans), pentaploidy and multiploidy.

The methods disclosed may comprise detecting, monitoring, quantitating, or evaluating one or more pathogen-derived nucleic acid molecules or one or more diseases or conditions caused by one or more pathogens. Exemplary pathogens include, but are not limited to, *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* or *Yersinia.* Additional pathogens include, but are not limited to, *Mycobacterium tuberculosis, Streptococcus, Pseudomonas, Shigella, Campylobacter,* and *Salmonella.*

The disease or conditions caused by one or more pathogens may comprise tuberculosis, pneumonia, foodborne illnesses, tetanus, typhoid fever, diphtheria, syphilis, leprosy, bacterial vaginosis, bacterial meningitis, bacterial pneumonia, a urinary tract infection, bacterial gastroenteritis, and bacterial skin infection. Examples of bacterial skin infections include, but are not limited to, impetigo which may be caused by *Staphylococcus aureus* or *Streptococcus pyogenes*; erysipelas which may be caused by a *streptococcus* bacterial infection of the deep epidermis with lymphatic spread; and cellulitis which may be caused by normal skin flora or by exogenous bacteria.

The pathogen may be a fungus, such as, *Candida, Aspergillus, Cryptococcus, Histoplasma, Pneumocystis,* and *Stachybotrys.* Examples of diseases or conditions caused by a fungus include, but are not limited to, jock itch, yeast infection, ringworm, and athlete's foot.

The pathogen may be a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis.

The pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g., *I. belli*), *Microsporidium* (e.g., *M. africanum,* M. ceylonensis), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*).

Therapeutics

The methods disclosed herein may comprise treating and/or preventing a disease or condition in a subject based on one or more biomedical outputs. The one or more biomedical outputs may recommend one or more therapies. The one or more biomedical outputs may suggest, select, designate, recommend or otherwise determine a course of treatment and/or prevention of a disease or condition. The one or more biomedical outputs may recommend modifying or continuing one or more therapies. Modifying one or more therapies may comprise administering, initiating, reducing, increasing, and/or terminating one or more therapies. The one or more therapies comprise an anti-cancer, antiviral, antibacterial, antifungal, immunosuppressive therapy, or a combination thereof. The one or more therapies may treat, alleviate, or prevent one or more diseases or indications.

Examples of anti-cancer therapies include, but are not limited to, surgery, chemotherapy, radiation therapy, immunotherapy/biological therapy, photodynamic therapy. Anti-cancer therapies may comprise chemotherapeutics, monoclonal antibodies (e.g., rituximab, trastuzumab), cancer vaccines (e.g., therapeutic vaccines, prophylactic vaccines), gene therapy, or combination thereof.

The one or more therapies may comprise an antimicrobial. Generally, an antimicrobial refers to a substance that kills or inhibits the growth of microorganisms such as bacteria, fungi, virus, or protozoans. Antimicrobial drugs either kill microbes (microbicidal) or prevent the growth of microbes (microbiostatic). There are mainly two classes of antimicrobial drugs, those obtained from natural sources (e.g., antibiotics, protein synthesis inhibitors (such as aminoglycosides, macrolides, tetracyclines, chloramphenicol, polypeptides)) and synthetic agents (e.g., sulphonamides, cotrimoxazole, quinolones). In some instances, the antimicrobial drug is an antibiotic, anti-viral, anti-fungal, anti-malarial, anti-tuberculosis drug, anti-leprotic, or anti-protozoal.

Antibiotics are generally used to treat bacterial infections. Antibiotics may be divided into two categories: bactericidal antibiotics and bacteriostatic antibiotics. Generally, bactericidals may kill bacteria directly where bacteriostatics may prevent them from dividing. Antibiotics may be derived from living organisms or may include synthetic antimicrobials, such as the sulfonamides. Antibiotics may include aminoglycosides, such as amikacin, gentamicin, kanamycin, neomycin, netilmicin, tobramycin, and paromomycin. Alternatively, antibiotics may be ansamycins (e.g., geldanamycin, herbimycin), cabacephems (e.g., loracarbef), carbapenems (e.g., ertapenem, doripenem, imipenem, cilastatin, meropenem), glycopeptides (e.g., teicoplanin, vancomycin, telavancin), lincosamides (e.g., clindamycin, lincomycin, daptomycin), macrolides (e.g., azithromycin, clarithromycin, dirithromycin, erythromycin, roxithromycin, troleandomycin, telithromycin, spectinomycin, spiramycin), nitrofurans (e.g., furazolidone, nitrofurantoin), and polypeptides (e.g., bacitracin, colistin, polymyxin B).

In some instances, the antibiotic therapy includes cephalosporins such as cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, and ceftobiprole.

The antibiotic therapy may also include penicillins. Examples of penicillins include amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, temocillin, and ticarcillin.

Alternatively, quinolines may be used to treat a bacterial infection. Examples of quinilones include ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin.

In some instances, the antibiotic therapy comprises a combination of two or more therapies. For example, amoxicillin and clavulanate, ampicillin and sulbactam, piperacillin and tazobactam, or ticarcillin and clavulanate may be used to treat a bacterial infection.

Sulfonamides may also be used to treat bacterial infections. Examples of sulfonamides include, but are not limited to, mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxazole (co-trimoxazole) (tmp-smx).

Tetracyclines are another example of antibiotics. Tetracyclines may inhibit the binding of aminoacyl-tRNA to the mRNA-ribosome complex by binding to the 30S ribosomal subunit in the mRNA translation complex. Tetracyclines include demeclocycline, doxycycline, minocycline, oxytetracycline, and tetracycline. Additional antibiotics that may be used to treat bacterial infections include arsphenamine, chloramphenicol, fosfomycin, fusidic acid, linezolid, metronidazole, mupirocin, platensimycin, quinupristin/dalfopristin, rifaximin, thiamphenicol, tigecycline, tinidazole, clofazimine, dapsone, capreomycin, cycloserine, ethambutol, ethionamide, isoniazid, pyrazinamide, rifampicin, rifamycin, rifabutin, rifapentine, and streptomycin.

Antiviral therapies are a class of medication used specifically for treating viral infections. Like antibiotics, specific antivirals are used for specific viruses. They are relatively harmless to the host, and therefore can be used to treat infections. Antiviral therapies may inhibit various stages of the viral life cycle. For example, an antiviral therapy may inhibit attachment of the virus to a cellular receptor. Such antiviral therapies may include agents that mimic the virus associated protein (VAP and bind to the cellular receptors. Other antiviral therapies may inhibit viral entry, viral uncoating (e.g., amantadine, rimantadine, pleconaril), viral synthesis, viral integration, viral transcription, or viral translation (e.g., fomivirsen). In some instances, the antiviral therapy is a morpholino antisense. Antiviral therapies should be distinguished from viricides, which actively deactivate virus particles outside the body.

Many of the antiviral drugs available are designed to treat infections by retroviruses, mostly HIV. Antiretroviral drugs may include the class of protease inhibitors, reverse transcriptase inhibitors, and integrase inhibitors. Drugs to treat HIV may include a protease inhibitor (e.g., invirase, saquinavir, kaletra, lopinavir, lexiva, fosamprenavir, norvir, ritonavir, prezista, duranavir, reyataz, viracept), integrase inhibitor (e.g., raltegravir), transcriptase inhibitor (e.g., abacavir, ziagen, agenerase, amprenavir, aptivus, tipranavir, crixivan, indinavir, fortovase, saquinavir, Intelence™, etravirine, isentress, viread), reverse transcriptase inhibitor (e.g., delavirdine, efavirenz, epivir, hivid, nevirapine, retrovir, AZT, stuvadine, truvada, videx), fusion inhibitor (e.g., fuzeon, enfuvirtide), chemokine coreceptor antagonist (e.g., selzentry, emtriva, emtricitabine, epzicom, or trizivir). Alternatively, antiretroviral therarapies may be combination therapies, such as atripla (e.g., efavirenz, emtricitabine, and tenofovira disoproxil fumarate) and completer (embricitabine, rilpivirine, and tenofovir disoproxil fumarate). Herpes viruses, best known for causing cold sores and genital herpes, are usually treated with the nucleoside analogue acyclovir. Viral hepatitis (A-E) are caused by five unrelated hepatotropic viruses and are also commonly treated with antiviral drugs depending on the type of infection. Influenza A and B viruses are important targets for the development of new influenza treatments to overcome the resistance to existing neuraminidase inhibitors such as oseltamivir.

In some instances, the antiviral therapy may comprise a reverse transcriptase inhibitor. Reverse transcriptase inhibitors may be nucleoside reverse transcriptase inhibitors or non-nucleoside reverse transcriptase inhibitors. Nucleoside reverse transcriptase inhibitors may include, but are not limited to, combivir, emtriva, epivir, epzicom, hivid, retrovir, trizivir, truvada, videx ec, videx, viread, zerit, and ziagen. Non-nucleoside reverse transcriptase inhibitors may comprise edurant, intelence, rescriptor, sustiva, and viramune (immediate release or extended release).

Protease inhibitors are another example of antiviral drugs and may include, but are not limited to, agenerase, aptivus, crixivan, fortovase, invirase, kaletra, lexiva, norvir, prezista, reyataz, and viracept. Alternatively, the antiviral therapy may comprise a fusion inhibitor (e.g., enfuviride) or an entry inhibitor (e.g., maraviroc).

Additional examples of antiviral drugs include abacavir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, fusion inhibitors, ganciclovir, ibacitabine, imunovir, idoxuridine, imiquimod, indinavir, inosine, integrase inhibitor, interferons (e.g., interferon type I, II, III), lamivudine, lopinavir, loviride, maraviroc, moroxydine, methisazone, nelfinavir, nevirapine, nexavir, nucleoside analogues, oseltamivir, peginterferon alfa-2a, penciclovir, peramivir, pleconaril, podophyllotoxin, protease inhibitors, raltegravir, reverse transcriptase inhibitors, ribavirin, rimantadine, ritonavir, pyramidine, saquinavir, stavudine, tea tree oil, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

An antifungal drug is medication that may be used to treat fungal infections such as athlete's foot, ringworm, candidiasis (thrush), serious systemic infections such as cryptococcal meningitis, and others. Antifungals work by exploiting differences between mammalian and fungal cells to kill off the fungal organism. Unlike bacteria, both fungi and humans are eukaryotes. Thus, fungal and human cells are similar at the molecular level, making it more difficult to find a target for an antifungal drug to attack that does not also exist in the infected organism.

Antiparasitics are a class of medications which are indicated for the treatment of infection by parasites, such as nematodes, cestodes, trematodes, infectious protozoa, and amoebae. Like antifungals, they must kill the infecting pest without serious damage to the host.

Systems, Kits, and Libraries

Methods of the disclosure can be implemented by way of systems, kits, libraries, or a combination thereof. The methods of the invention may comprise one or more systems. Systems of the disclosure can be implemented by way of kits, libraries, or both. A system may comprise one or more components to perform any of the methods or any of the steps of the methods disclosed herein. For example, a system may comprise one or more kits, devices, libraries, or a combination thereof. A system may comprise one or more sequencers, processors, memory locations, computers, computer systems, or a combination thereof. A system may comprise a transmission device.

A kit may comprise various reagents for implementing various operations disclosed herein, including sample processing and/or analysis operations. A kit may comprise instructions for implementing at least some of the operations disclosed herein. A kit may comprise one or more capture probes, one or more beads, one or more labels, one or more linkers, one or more devices, one or more reagents, one or more buffers, one or more samples, one or more databases, or a combination thereof.

A library may comprise one or more capture probes. A library may comprise one or more subsets of nucleic acid molecules. A library may comprise one or more databases. A library may be produced or generated from any of the methods, kits, or systems disclosed herein. A database library may be produced from one or more databases. A method for producing one or more libraries may comprise (a) aggregating information from one or more databases to produce an aggregated data set; (b) analyzing the aggregated data set; and (c) producing one or more database libraries from the aggregated data set.

EXAMPLES

Methods and systems of the present disclosure may be applied to various types of samples, such as nucleic acid samples, protein samples, or other biological samples.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 1. Three Independent Workflows for the Production of ESP, HGCP and LRP Libraries This example provides three independent workflows for the preparation of an Exome Supplement Plus (ESP), high GC content (HGCP) and specific enrichment pulldown (LRP) library from a single nucleic acid sample.

Illumina's RSB (or 50 mM Sodium Ascorbic) was added to three different Covaris microtubes containing 1 µg of genomic DNA (DNA) from a single sample to produce 52.5 µL of total volume in each microtube. The microtubes were designated as ESP, HGCP, and LRP. The gDNA in the microtube was sheared using the Covaris settings in Table 1.

TABLE 1

| Covaris settings | | | |
|---|---|---|---|
| | ESP | HGCP | LRP |
| Duty factor: | 20% | 20% | 20% |
| Cyc/burst: | 200 | 200 | 200 |
| Time (sec): | 80 | 80 | 25 |
| Peak Incident Power (W): | 50 | 50 | 50 |
| Temp (*C.): | 20 | 20 | 20 |

The microtubes were spun down and 50 µL of the fragmented DNA were transferred to PCR plates. 10 µL of RSB was added to each well. The HGCP sample plate was heated at 65° C. for 5 minutes. The ESP and LRP plates were not heated at 65° C. 40 µL Illumina's ERP was added to each sample plate by pipetting up and down to mix. The plates were sealed. The plates were incubated at 30° C. for 30 minutes. The DNA was purified by adding Ampure XP beads to each plate. For the ESP and HGCP plates, 90 µL of Ampure XP beads were added. For the LRP plate, 50 µL of Ampure XP beads were added. DNA was eluted with 17.5 µL of RSB.

12.5 µL of Illumina's ATL was added to the eluted DNA and transferred to a new plate. The plates with the eluted DNA were incubated at 37° C. for 30 minutes.

Adapters were ligated to the DNA by adding 2.5 µL of RSB, 2.5 µL of Ligation (LIG) mix, and 2.5 µL of adapters to each well. The samples were mixed well and the plate was sealed. The plate was incubated for 10 minutes at 30° C. 5 µL of STL (0.5M EDTA) was added to each well. The samples were mixed thoroughly. The adapter ligated DNA was purified by adding 42.5 µL of Ampure XP beads to each well. Ligated DNA was eluted with 50 µL of RSB. The ligated DNA was purified by adding 50 µL of Ampure beads and eluting the DNA with 20 µL of RSB. The Ampure bead purification and elution was performed twice.

The ligated DNA was amplified by adding 25 µL of 2× kappa hifi polymerase and 5 µL of primer to each ligated DNA sample and by running a PCR with 8 cycles. The amplified DNA was purified with 50 µL of Ampure beads and the DNA was eluted with 30 µL of RSB. The amplified DNA from the three different sample preparations were used to prepare the ESP, HGCP, and LRP libraries.

The ESP, HGCP, and LRP libraries were validated by running each library on a DNA 1000 chip and quantifying with a BR Qubit assay.

Hybridization reactions were performed on the ESP, HGCP, and LRP samples using ESP, HGCP and LRP specific capture probes. 3 independent hybridization reactions were set up according to Table 2.

TABLE 2

| pull down | ESP | HGCP | LRP |
| DNA library | ESP | HGCP | LRP |
| probe | ESP | HGCP | LRP |

Hybridization reactions were performed according to Agilent's standard Sure Select protocol.

Example 2. Two Independent Workflows for the Production of ESP, HGCP and LRP Libraries This example provides two independent workflows for the preparation of an Exome Supplement Plus (ESP), high GC content (HGCP) and specific enrichment pulldown (LRP) library from a single nucleic acid sample.

RSB (or 50 mM Sodium Acetate) was added to two different Covaris microtubes containing 1 µg of genomic DNA (DNA) from a single sample to produce 52.5 µL of total volume in each microtube. The microtubes were designated as ESP/HGCP and LRP. The gDNA in the microtube was sheared using the Covaris settings in Table 3.

TABLE 3

| Covaris settings | | |
|---|---|---|
| | ESP/HGCP | LRP |
| Duty factor: | 20% | 20% |
| Cyc/burst: | 200 | 200 |
| Time (sec): | 80 | 25 |
| Peak Incident Power (W): | 50 | 50 |
| Temp (*C.): | 20 | 20 |

The microtubes were spun down and 50 µL of the fragmented DNA were transferred to PCR plates. 10 µL of RSB was added to each well. The ESP/HGCP sample plate was heated at 65° C. for 5 minutes. Or the ESP/HGCP and LRP plates were not heated at 65° C. 40 µL ERP was added to each sample plate by pipetting up and down to mix. The plates were sealed. The plates were incubated at 30° C. for 30 minutes. The DNA was purified by adding Ampure XP beads to each plate. For the ESP and HGCP plates, 90 μL of Ampure XP beads were added. For the LRP plate, 50 μL of Ampure XP beads were added. DNA was eluted with 17.5 μL of RSB.

12.5 μL of ATL was added to the eluted DNA. The plates with the eluted DNA were incubated at 37° C. for 30 minutes.

Adapters were ligated to the DNA by adding 2.5 μL of RSB, 2.5 μL of Ligation (LIG) mix, and 2.5 μL of adapters to each well. The samples were mixed well and the plate was sealed. The plate was incubated for 10 minutes at 30° C. 5 μL of STL (0.5M EDTA) was added to each well. The samples were mixed thoroughly. The adapter ligated DNA was purified by adding 42.5 μL of Ampure XP beads to each well. Ligated DNA was eluted with 50 μL of RSB. The ligated DNA was purified by adding 50 μL of Ampure beads and eluting the DNA with 20 μL of RSB. The Ampure bead purification and elution was performed twice.

The ligated DNA was amplified by adding 25 μL of 2× kappa hifi polymerase and 5 μL of primer to each ligated DNA sample and by running a PCR with 8 cycles. The amplified DNA was purified with 50 μL of Ampure beads and the DNA was eluted with 30 μL of RSB. The amplified DNA from the sample preparations were used to prepare the ESP, HGCP, and LRP libraries.

The ESP, HGCP, and LRP libraries were validated by running each library on a DNA High-Sensitivity chip and quantifying with a BR Qubit assay.

Hybrization reactions were performed on the ESP, HGCP, and LRP samples using ESP, HGCP and LRP specific capture probes. 3 independent hybridization reactions were set up according to Table 4.

TABLE 4

| pull down | ESP | HGCP | LRP |
| --- | --- | --- | --- |
| DNA library | ESP/HGCP | ESP/HGCP | LRP |
| probe | ESP | HGCP | LRP |

Hybridization reactions were performed according to Agilent's standard Sure Select protocol.

Example 3. A Single Workflow for the Production of ESP, HGCP and LRP Libraries

This example provides a single workflow for the preparation of an Exome Supplement Plus (ESP), high GC content (HGCP) and specific enrichment pulldown (LRP) library from a single nucleic acid sample.

RSB (or 50 mM Sodium Acetate) was added to a Covaris microtube containing 3 μg of genomic DNA (DNA) from a single sample to produce 52.5 μL of total volume. The gDNA in the microtube was sheared using the Covaris settings in Table 5.

TABLE 5

| Covaris settings | |
| --- | --- |
| Duty factor: | 20% |
| Cyc/burst: | 200 |
| Time (sec): | 25 |
| Peak Incident Power (W): | 50 |
| Temp (*C.): | 20 |

The microtubes were spun down and 50 μL of the fragmented DNA were transferred to a single PCR plate. 10 μL of RSB was added to each well. The sample plate was heated at 65° C. for 5 minutes or were not heated at 65° C. 40 μL ERP was added to each sample plate by pipetting up and down to mix. The plates were sealed. The plate were incubated at 30° C. for 30 minutes. The DNA was purified by adding Ampure XP beads to each plate. 90 μL of Ampure XP beads were added to the plates. The mixture was incubated for 8 minutes at room temperature. The standard Ampure protocol was performed. Beads were rehydrated in 20 μL of thawed RSB for 2 minutes at room temperature. 17.5 μL of supernatant was transferred to new wells in an Illumina's ALP plate.

12.5 μL of ATL was added to the eluted DNA. The ALP plates were incubated at 37° C. for 30 minutes.

Adapters were ligated to the DNA by adding 2.5 μL of RSB, 2.5 μL of Ligation (LIG) mix, and 2.5 μL of adapters to each well. The samples were mixed well and the plate was sealed. The plate was incubated for 10 minutes at 30° C. 5 μL of STL (0.5M EDTA) was added to each well. The samples were mixed thoroughly. The adapter ligated DNA was purified by adding 42.5 μL of Ampure XP beads to each well. Ligated DNA was eluted with 100 μL of RSB. 50 μL of Ampure XP beads were added to the 100 μL of ligated DNA. The 150 μL of the supernatant was transferred to a new well, leaving the Ampure XP bead bound DNA in the previous wells. DNA was eluted from the Ampure XP beads by adding 20 μL of RSB, the eluted DNA is the LRP subset.

20 μL of Ampure beads were added to the 150 μL of supernatant. The DNA was eluted in 100 μL of RSB. 60 μL of Ampure XP beads were added to the 100 μL of DNA. The 160 μL of supernatant was transferred to a new well, leaving the Ampure XP bead bound DNA in the previous wells. DNA was eluted from the Ampure XP beads by adding 20 μL of RSB, the eluted DNA is the ESP/HGCP subset.

The LRP subset of DNA and the ESP/HGCP subset of DNA were amplified by adding 25 μL of 2× kappa hifi polymerase and 5 μL of primer to each ligated DNA sample and by running a PCR with 8 cycles. The amplified DNA was purified with 50 μL of Ampure XP beads and the beads were rehydrated in 30 μL of RSB. The amplified DNA from the subsets were used to prepare the ESP, HGCP, and LRP libraries.

The ESP, HGCP, and LRP libraries were validated by running each library on a DNA High-Sensitivity chip and quantifying with a BR Qubit assay.

Hybridization reactions were performed on the ESP, HGCP, and LRP samples using ESP, HGCP and LRP specific capture probes. 3 independent hybridization reactions were set up according to Table 6.

TABLE 6

| pull down | ESP | HGCP | LRP |
| --- | --- | --- | --- |
| DNA library | ESP/HGCP | ESP/HGCP | LRP |
| probe | ESP | HGCP | LRP |

Hybridization reactions were performed according to Agilent's standard Sure Select protocol.

Example 4. Shear Time and Fragment Sizes

Figure 5:
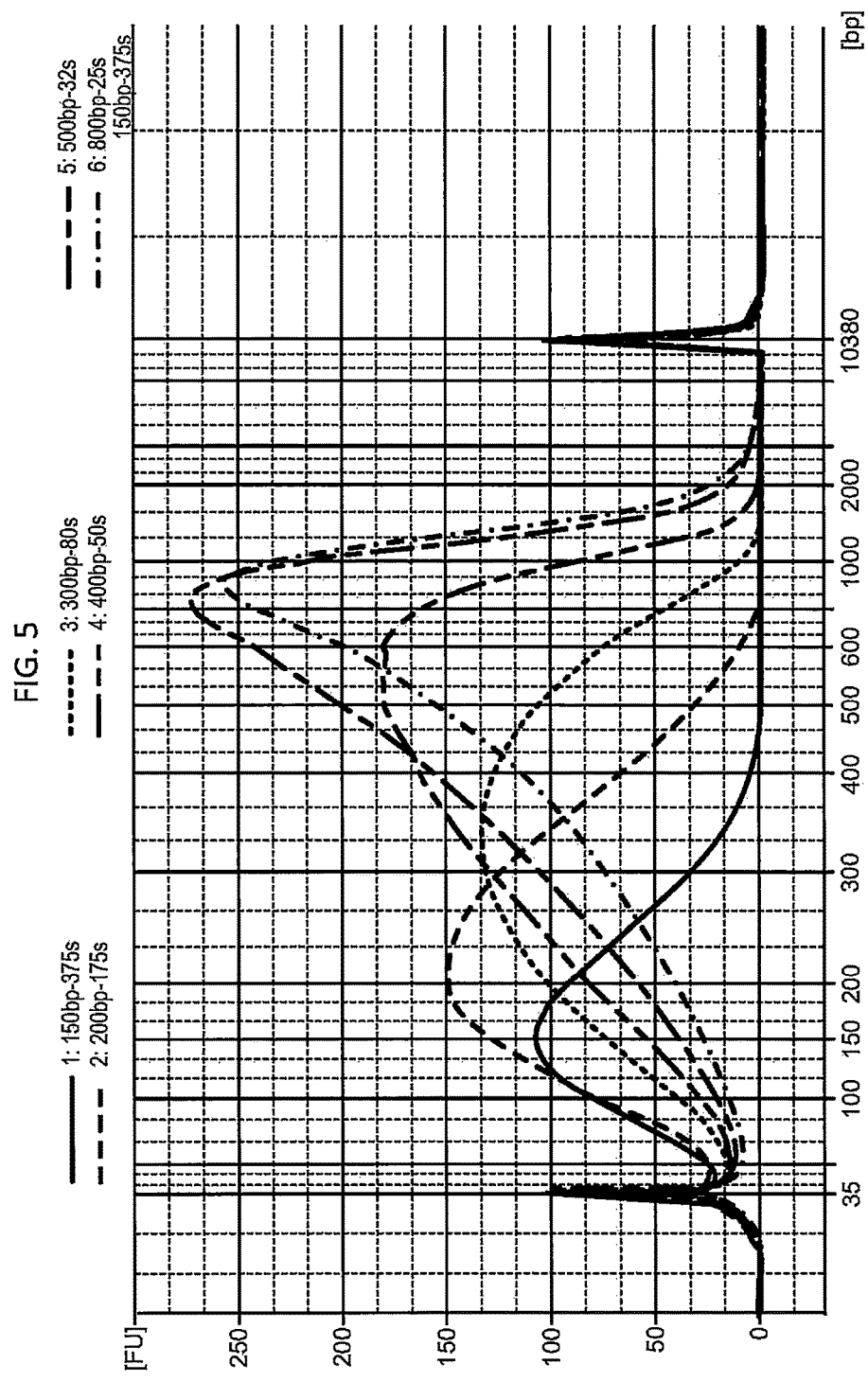
FIG. 5. shows effects of shear time on fragment size.

Genomic DNA (gDNA) was sheared by varying the shear time of a Covaris setting. The gDNA fragments produced by various shear times was then analyzed. Results are shown in FIG. 5 and Table 7.

TABLE 7

Shear time and mean fragment size

| Number | Shear Time (seconds) | Mean Fragment Size (base pairs) |
|---|---|---|
| 1 | 375 | 150 |
| 2 | 175 | 200 |
| 3 | 80 | 200 |
| 4 | 40 | 400 |
| 5 | 32 | 500 |
| 6 | 25 | 800 |

Example 5. Bead Ratio and Fragment Size

Figure 6:
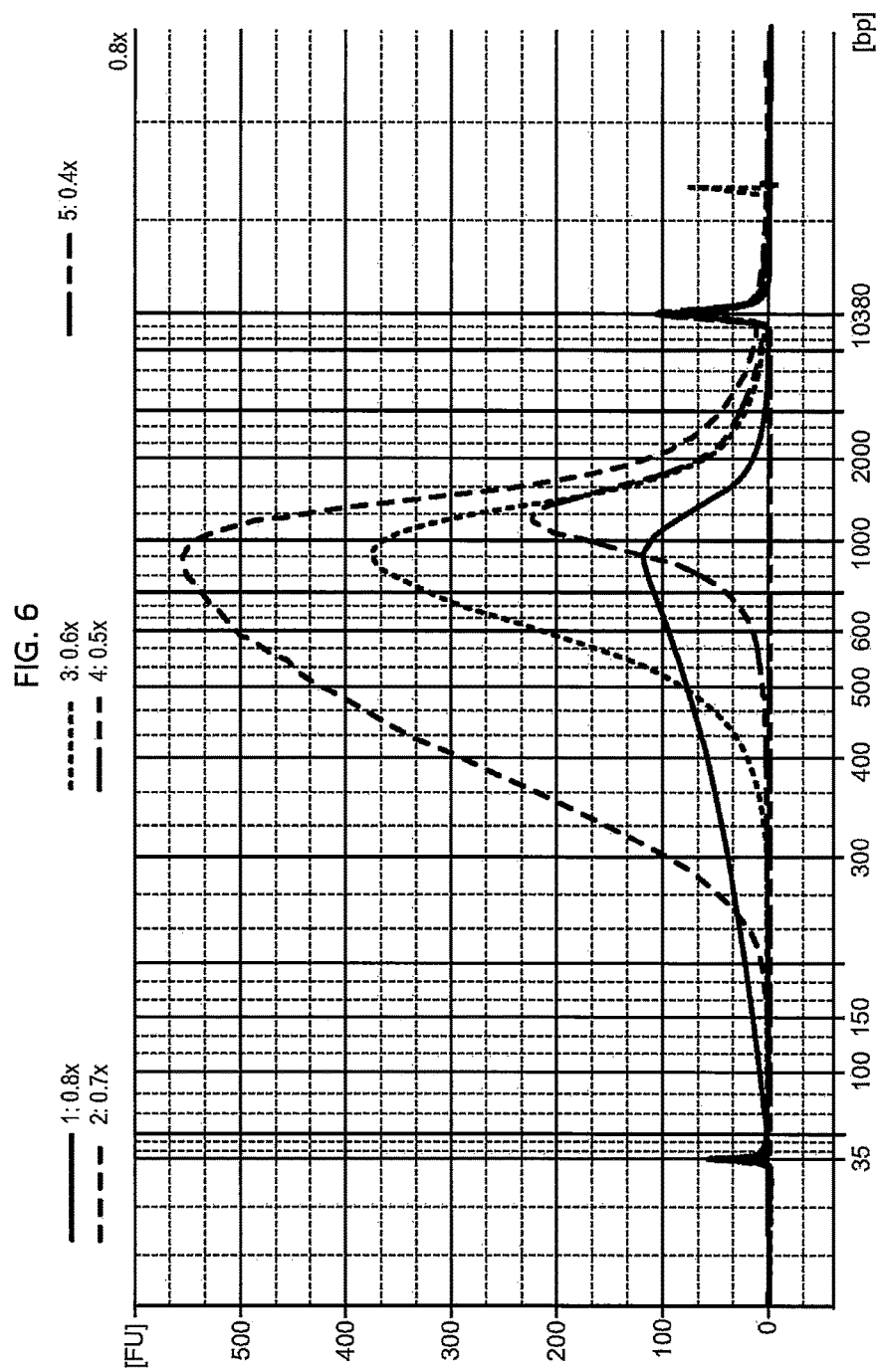
FIG. 6. shows effects of bead ratio on fragment size.

The ratio of the volume of beads to the volume of the nucleic acid sample was varied and the effects of these ratios on mean fragment size was analyzed. As can be shown in FIG. 6A, varying the ratio of the volume of the volume of the beads to the volume of the nucleic acid sample from 0.8 (line 1), 0.7 (line 2), 0.6 (line 3), 0.5 (line 4) and 0.4 (line 5) resulted in a shift in the mean size of the DNA fragments. Generally, it appeared that the lower the ratio, then the larger the mean fragment size.

Example 6. Ligation Reactions and Fragment Size

Figure 7:
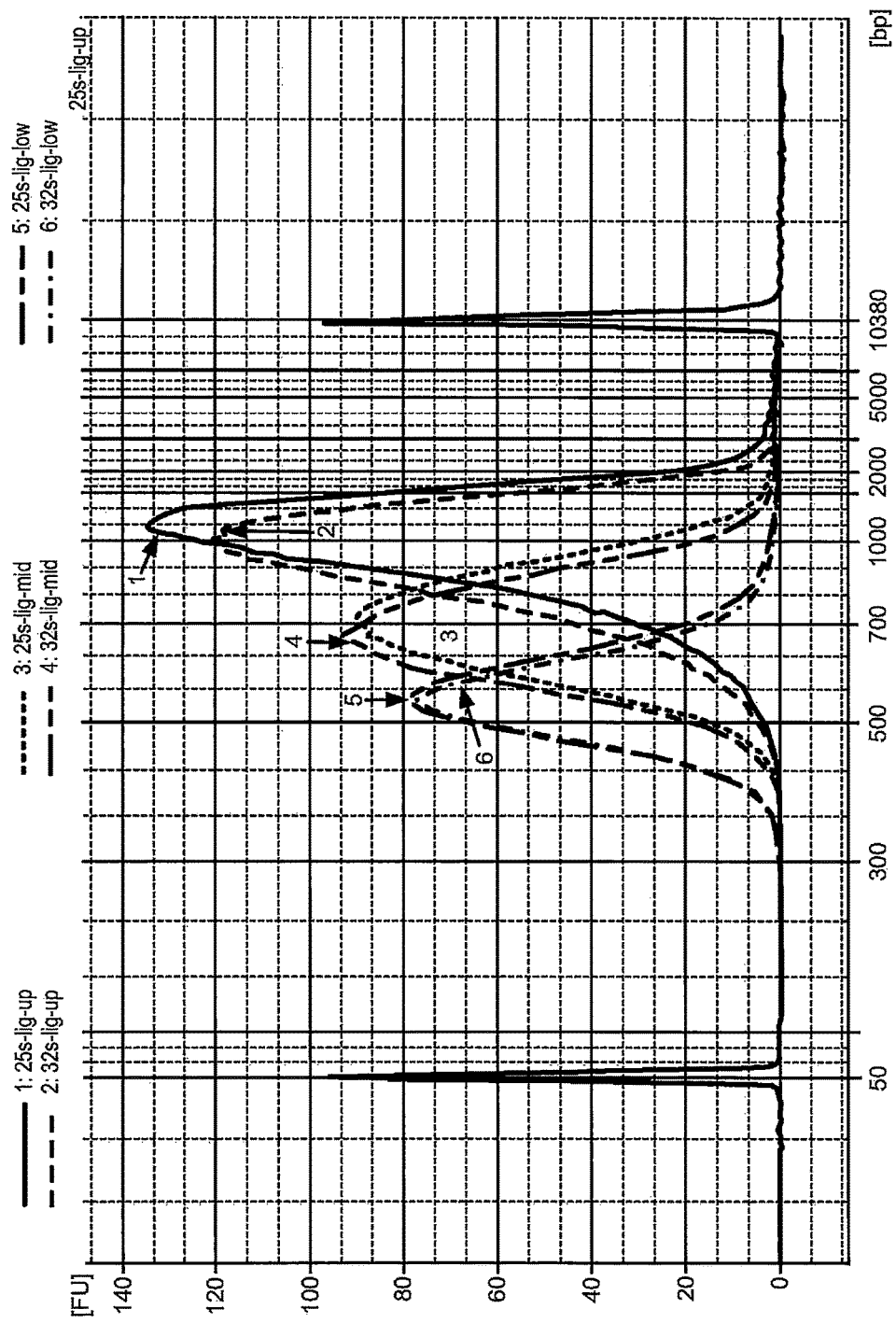
FIG. 7. shows effects of shear time on fragment size.
Figure 8:
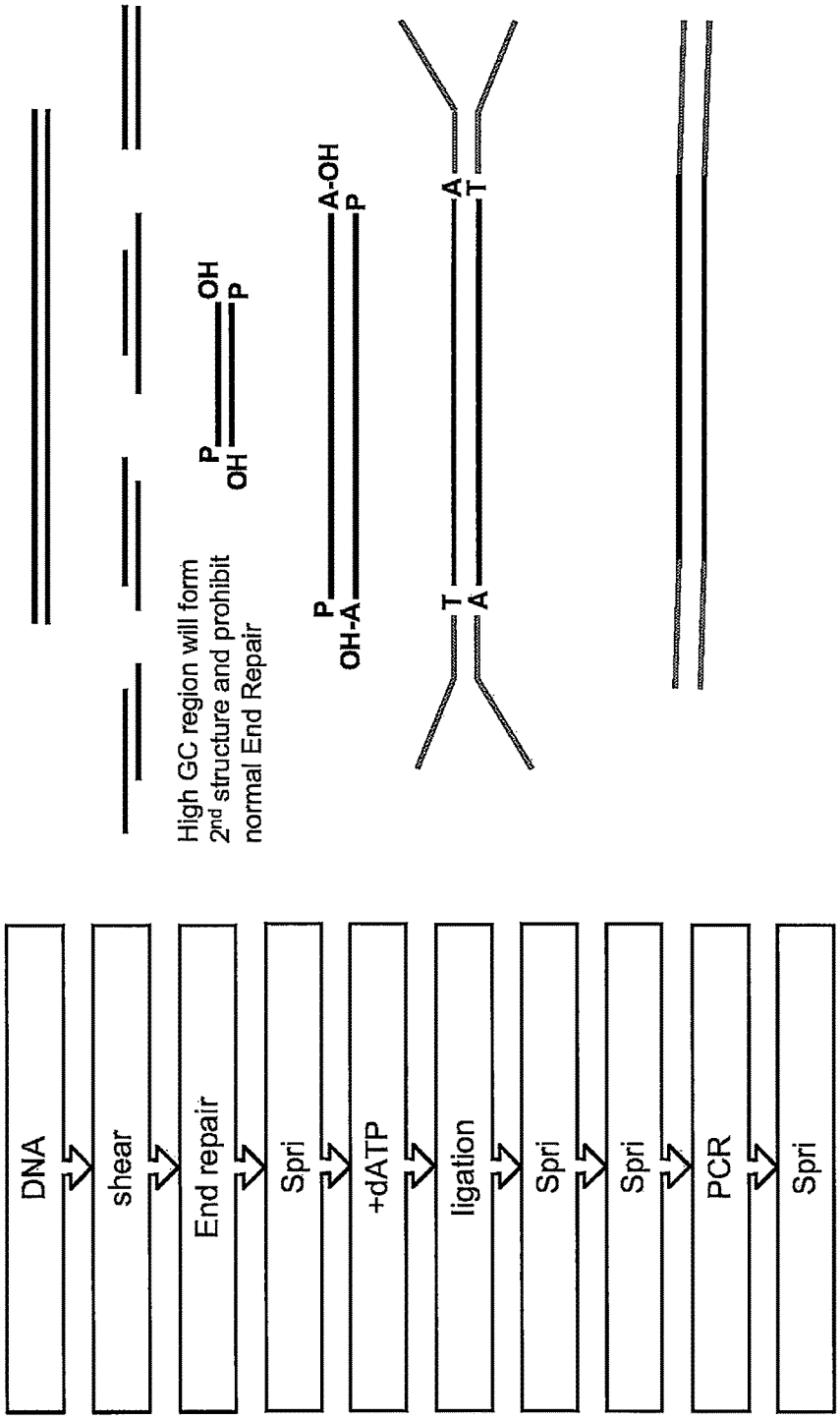
FIG. 8. depicts a schematic of a nucleic acid library construction workflow.
Figure 9:
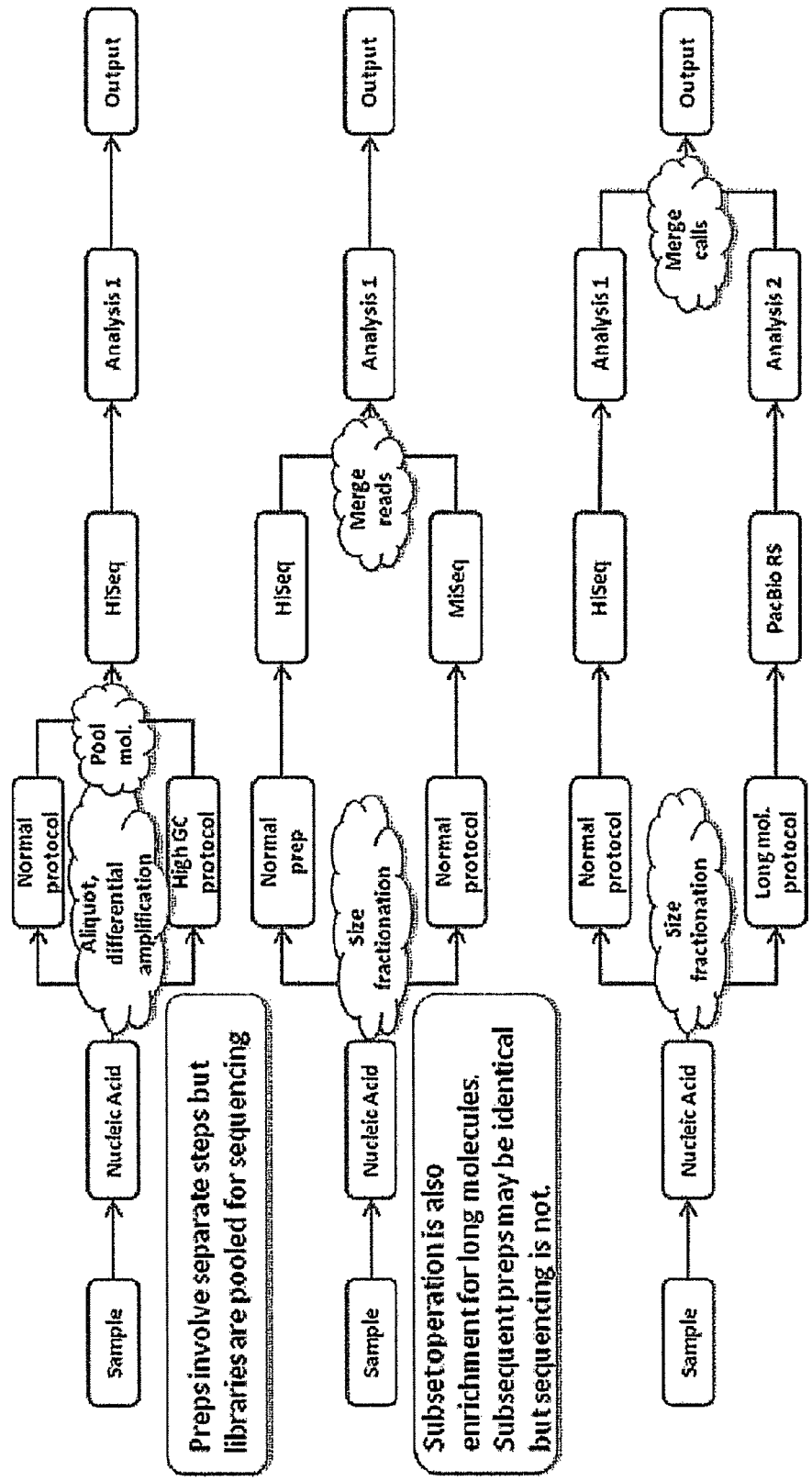
FIG. 9. depicts more detailed examples of the assay and analysis workflows shown in FIG. 2A-2C.
Figure 10:
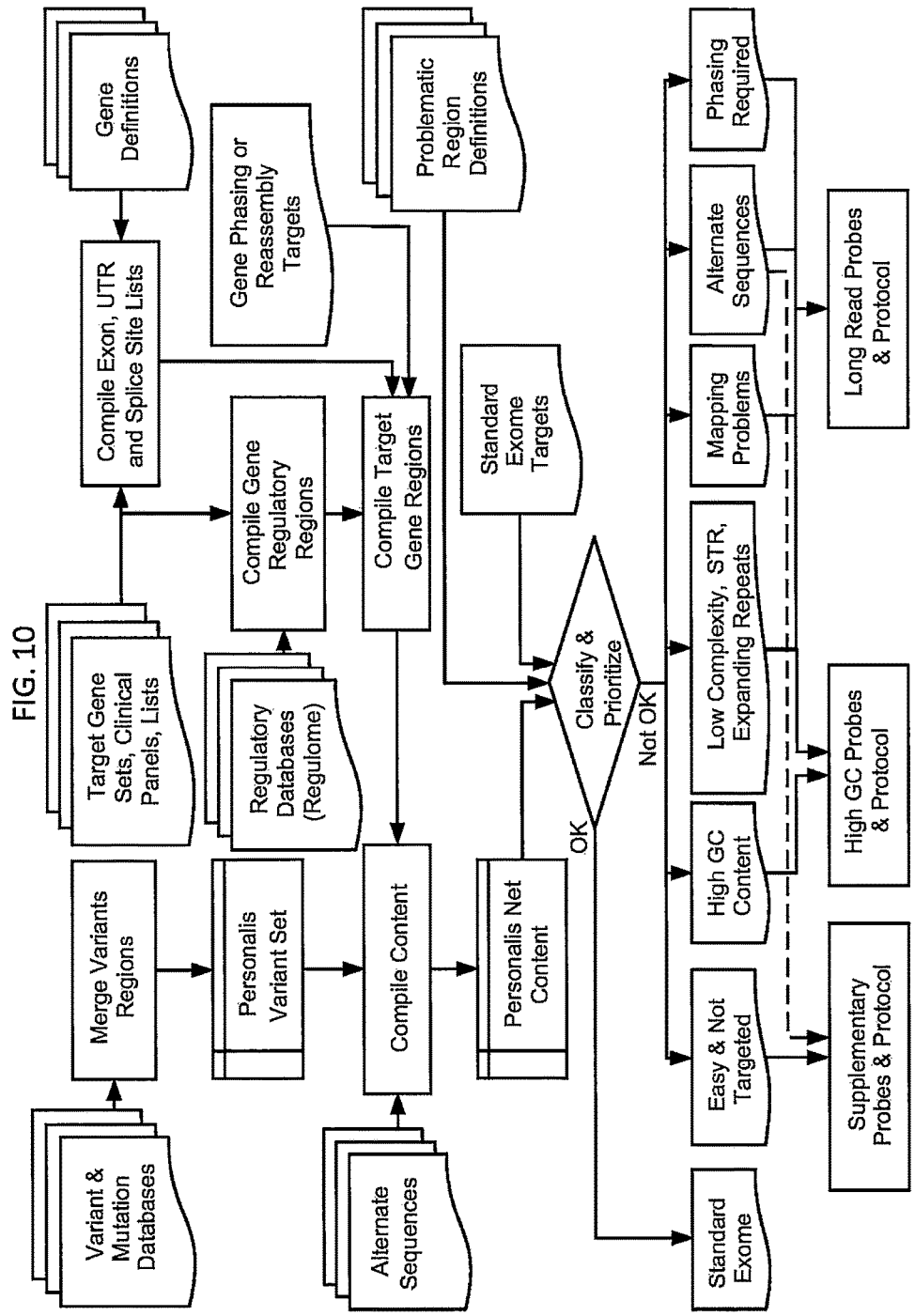
FIG. 10. depicts a method for developing mutlithreaded assay addressing multiple biomedical applications. Variants, genes, exons, UTRs, regulatory regions, splice sites, alternate sequences and other content of interest are combined from several databases to produce an aggregate set of content which is applicable to multiple biomedical reports. This content is then categorized based on local or global genomic context, nucleotide content, sequencing performance and interpretation demands and then subsequently grouped into subsets for specialized protocol and assay development.
Figure 11:
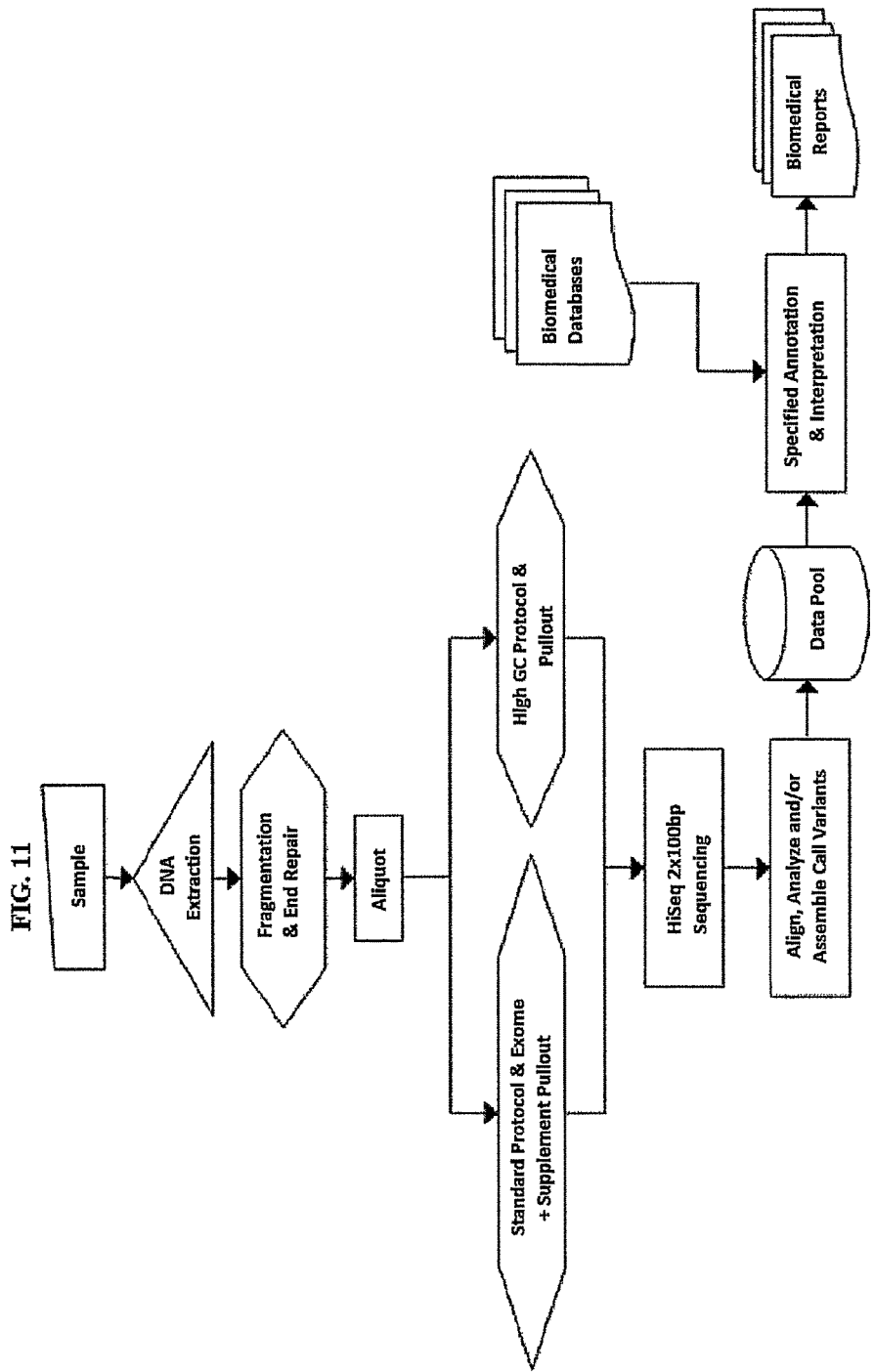
FIG. 11. depicts an assay comprising multiple subsets of DNA enriched for different genomic regions, undergoing some independent processing steps prior to being combined for a sequencing assay. Reads from the two or more subsets are combined either a) in the sequencing device b) subsequently by means of one or more algorithms to produce a single best result for the regions addressed by the union of the two or more subsets and resulting in a data pool that may be used for one or more biomedical reports.
Figure 12:
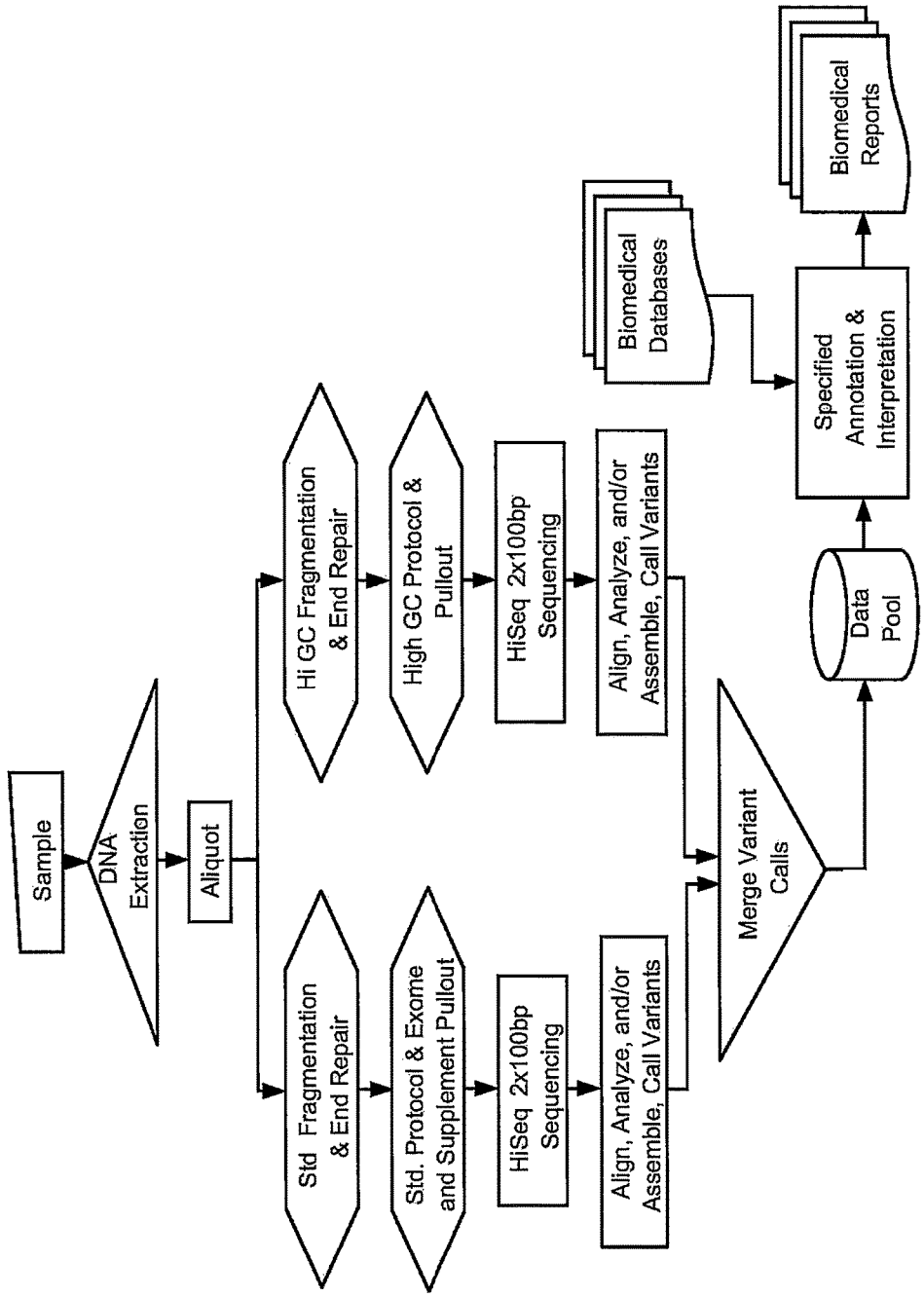
FIG. 12. depicts an assay comprising multiple subsets of DNA enriched for different genomic regions, undergoing some independent processing steps prior to being independently sequenced and analyzed for variants. Variants from the two subsets are merged by means of one or more algorithms to produce a single best result for the regions addressed by the union of the two or more subsets and resulting in a data pool that may be used for one or more biomedical reports.
Figure 13:
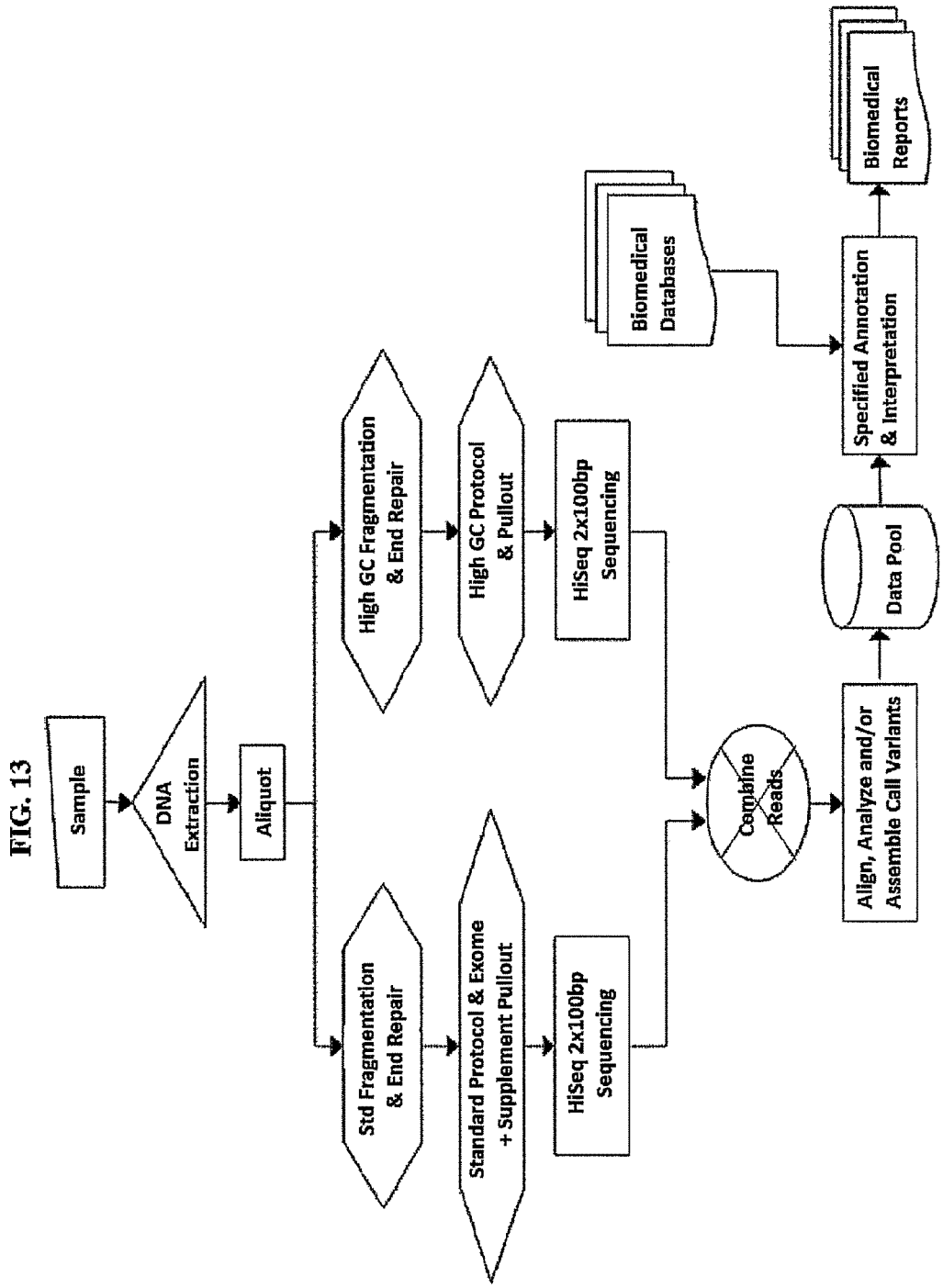
FIG. 13. depicts an assay comprising multiple subsets of DNA enriched for different genomic regions, undergoing some independent processing steps prior to being independently sequenced and producing primary data which may include sequence reads. Primary data from the two or more assays are combined and analyzed by one or more algorithms to produce a single best result for all of the regions addressed by the union of the two or more subsets resulting in a data pool that may be used for one or more biomedical reports.
Figure 14:
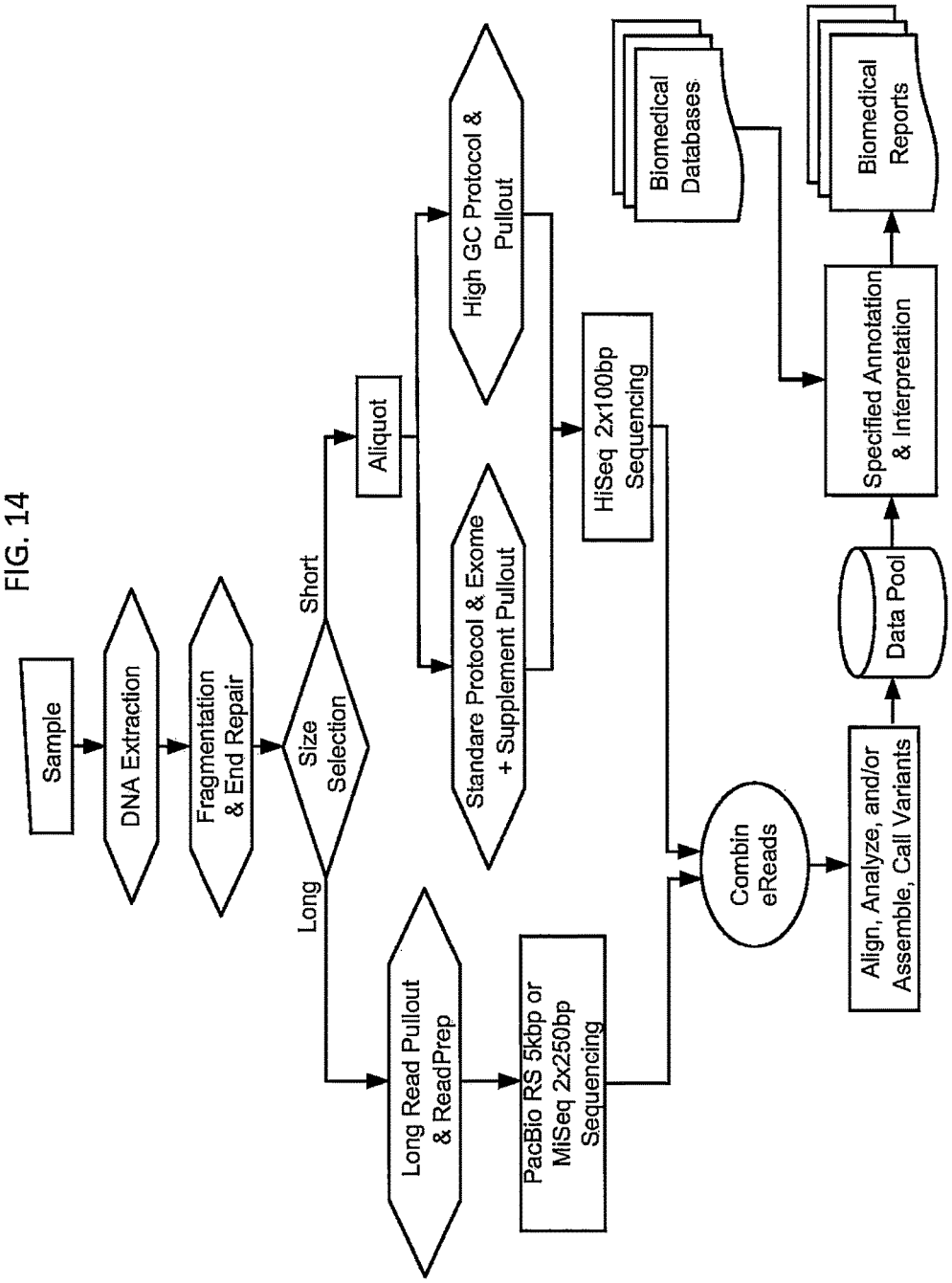
FIG. 14. depicts a multi-threaded assay comprising two subsets of DNA produced by size selection and one of these further divided into two subsets of DNA enriched for different genomic regions based on GC content. The longer molecules undergo sequencing using a technology appropriate for longer molecules. The two shorter molecule subsets are further prepared and amplified based on protocols appropriate to the Tm of the subsets then pooled for sequencing on a high throughput short read sequencer, the HiSeq. In this example primary data from the sequencing is merged and analyzed by means of one or more algorithms to produce a single best result for all of the regions addressed by the subsets and resulting in a data pool that may be used for one or more biomedical reports.
Figure 15:
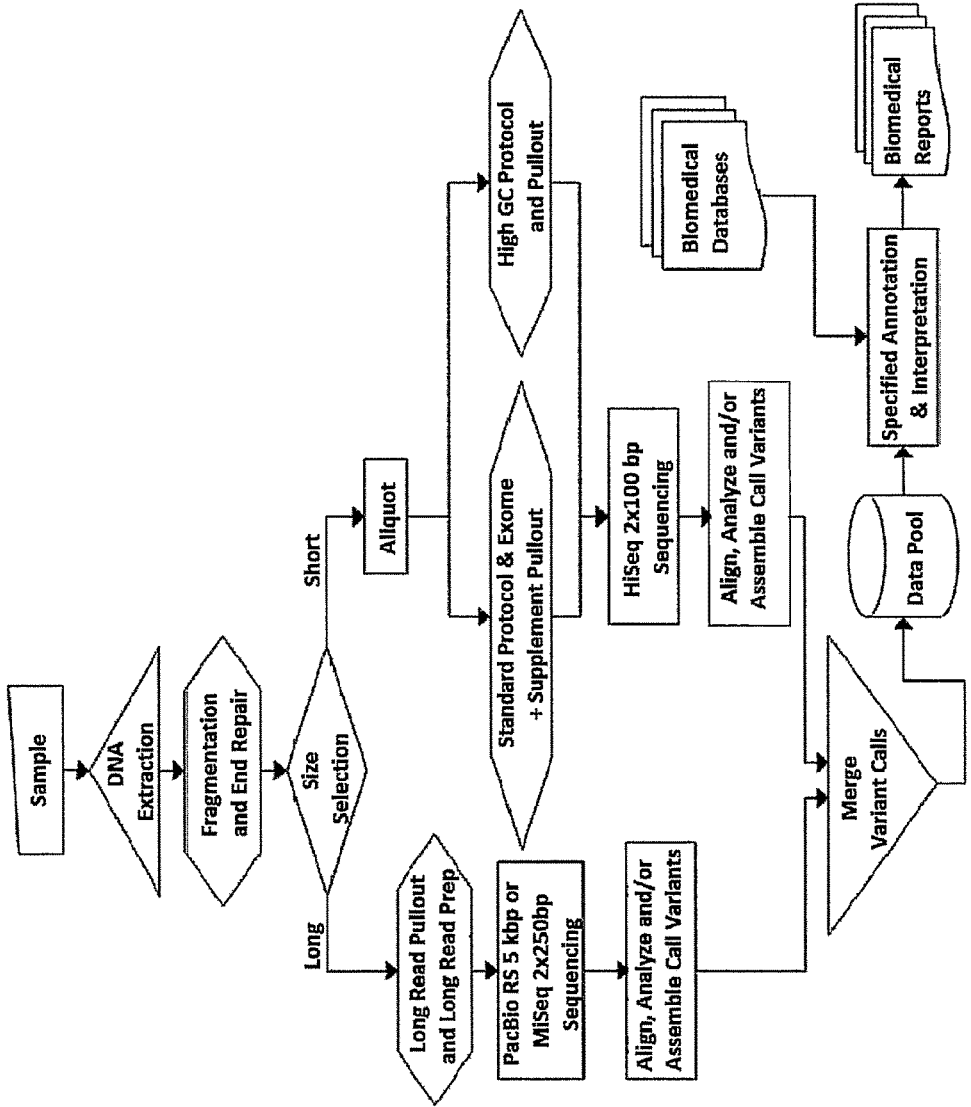
FIG. 15. depicts a multi-threaded assay comprising two subsets of DNA produced by size selection and one of these further divided into two subsets of DNA enriched for different genomic regions based on GC content. The longer molecules undergo sequencing using a technology appropriate for longer molecules. The two shorter molecule subsets are further prepared and amplified based on protocols appropriate to the Tm of the subsets then pooled for sequencing on a high throughput short read sequencer, the HiSeq. In this example primary data from the two sequencing technologies are analyzed separately for variants which are then merged by means of one or more algorithms to produce a single best result for all of the regions addressed by the subsets and resulting in a data pool that may be used for one or more biomedical reports.

A combination of two different shear times and three different ligation reactions were conducted on a nucleic acid sample. Sample 1 was sheared for 25 seconds and a ligation reaction was performed on the long insert DNA as prepared by Step 5 of Example 9 (lig-up). Sample 2 was sheared for 32 seconds and a ligation reaction was performed on the long insert DNA as prepared by Step 5 of Example 9 (lig-up). Sample 3 was sheared for 25 seconds and a ligation reaction was performed on the mid insert DNA as prepared by Step 8 of Example 9 (lig-mid). Sample 4 was sheared for 32 seconds and a ligation reaction was performed on the mid insert DNA as prepared by Step 8 of Example 9 (lig-mid). Sample 5 was sheared for 25 seconds and a ligation reaction was performed on the short insert DNA as prepared by Step 11 of Example 9 (lig-low). Sample 6 was sheared for 32 seconds and a ligation reaction was performed on the short insert DNA as prepared by Step 11 of Example 9 (lig-low). FIG. 7 shows the mean fragment size for the six reactions.

Example 7. Rhodobacter Sphaeroides

The *Rhodobacter sphaeroides* ATCC 17025 genome is 4.56 Million base pairs long and the GC content of the genome was analyzed. Results for the analysis are shown in Table 8.

TABLE 8

| Browser Chrom/ Plasmid Name | Length (bp) | GC Content (%) | Gene Count | NCBI RefSeq Accession |
|---|---|---|---|---|
| chr | 3217726 | 68.48 | 3181 | NC_009428 |
| plasmid_pRSPA01 | 877879 | 67.69 | 849 | NC_009429 |
| plasmid_pRSPA02 | 289489 | 67.6 | 278 | NC_009430 |
| plasmid_pRSPA03 | 121962 | 69.36 | 114 | NC_009431 |
| plasmid_pRSPA04 | 36198 | 64.05 | 32 | NC_009432 |
| plasmid_pRSPA05 | 13873 | 58.93 | 12 | NC_009433 |

Example 8. Optimization of *Rhodobacter Sphaeroides* DNA (High GC Content)

DNA from *Rhodobacter Sphaeroides* was amplified with a variety of polymerases and amplification conditions. Amplified DNA was then sequenced. High GC flowcell refers to sequencing reactions on DNA samples comprising primarily DNA with high GC content. Mix GC flowcell refers to sequencing reactions on DNA samples comprising a mixture of DNA with high and low GC content. As shown in Tables 9, brief heating at 65° C. before ER (end repair) improved coverage of high GC content DNA (see PST-000292).

TABLE 9

| DNA | PCR conditions | PF reads | mapped reads | ratio (>80% GC, <60% GC) |
|---|---|---|---|---|
| 2 × 150, High GC flowcell (primarily High GC content) | | | | |
| PST-000190 | PCR free | 985736 | 945734 | 95.94% 73.90% |
| PST-000191 | kapa 10 cycle | 1211930 | 1174309 | 96.90% 70.80% |
| PST-000192 | kapa 10 cycle + betaine | 1247310 | 1206917 | 96.76% 70.80% |
| PST-000193 | kapa 10 cycle + DMSO | 1183084 | 1144464 | 96.74% 70.40% |
| PST-000194 | kapa hifi 10 cycle | 1102832 | 1067306 | 96.78% 68.30% |
| PST-000195 | kapa hifi 10 cycle + deaza_dGTP | 756856 | 739857 | 97.75% 2.40% |
| PST-000196 | kapa GC 10 cycle | 1299004 | 1255979 | 96.69% 70.60% |
| PST-000197 | illumina 10 cycle | 1347780 | 1298231 | 96.32% 52.10% |
| PST-000198 | illumina 10 cycle, long denature | 1256278 | 1209607 | 96.28% 50.60% |
| PST-000199 | kapa 8 cycle | 1013116 | 978349 | 96.57% 69.80% |
| 2 × 150, Mix GC flowcell (high and low GC content) | | | | |
| PST-000191 | kapa 10 cycle | 909256 | 854341 | 93.96% 66.80% |
| 2 × 250, Mix GC flowcell (high and low GC content) | | | | |
| PST-000290 | PCR free | 1009022 | 779191 | 77.22% 70.80% |
| PST-000291 | PCR free, 60 C. ER | 1100298 | 863058 | 78.44% 73.10% |
| PST-000292 | PCR free, 65 C. ER | 1157944 | 932378 | 80.52% 78.20% |
| PST-000293 | PCR free, 70 C. ER | 1200318 | 944391 | 78.68% 75.10% |

Example 9. Preparation of Genomic DNA

The following steps were used to prepare subsets of nucleic acid molecules from a sample comprising genomic DNA:

1. A sample comprising genomic DNA is sheared with M220 for 15-35 seconds.
2. The fragmented gDNA was purified with SPRI beads after ligation (ratio of the volume of SPRI beads to the DNA sample was 1) and the DNA was eluted into 100 µL of elution buffer (EB).
3. 50 µL of SPRI beads were added to the 100 µL of DNA.
4. The supernatant was transferred to a new tube.
5. The DNA from the remaining bead bound DNA was eluted. This eluted DNA was called the long insert.
6. 10 µL of SPRI beads were added to the supernatant from Step 4.
7. The supernatant from Step 6 was transferred to a new tube.
8. The DNA from the remaining bead bound DNA of Step 6 was eluted. This eluted DNA was called the mid insert.
9. 20 µL of SPRI beads were added to the supernatant from Step 7.
10. The supernatant from Step 9 was transferred to a new tube.
11. The DNA from the remaining bead bound DNA of Step 9 was eluted. This eluted DNA was called the short insert.

Example 10. Segregation and Independent Processing of Interpretable Genomic Content Illumina TruSeq Exome enrichment followed by Illumina sequencing is a typical example of targeted DNA sequencing. However, this process can fail to target many biomedically interesting non-exomic as well as exomic regions for enrichment and also can fail to adequately sequence many of the regions it does target. Furthermore, many of the sequenced regions may have unacceptably high error rates. We found that many of these gaps and failures are due to specific problems that, while difficult for bulk sequencing, may be more adequately addressed by specialized sequencing protocols or technologies.

We have compiled a large and unique set of medically interpretable content encompassing both proprietary data and numerous publicly available sources that include both exomic and non-exomic regions, as well as non-reference or alternative sequences. Much of this isn't adequately covered in standard exome sequencing. We have analyzed this performance gap and developed a multipronged approach to more completely cover this content by independently processing particular types of problems with specialized sample preparation, amplification, sequencing technology and/or bioinformatics to best recover the underlying sequence. We have developed three targeted subsets and protocols to address this performance gap.

In content regions skipped by standard exome processing but still in nominally tractable genomic regions, we have developed additional baits to enrich these regions for standard sequencing. In some cases, we may additionally target non-reference sequence that is of interest (e.g. common normal and/or cancer SV junctions, common InDels or in general sequences in which the reference has a rare allele that we believe will adversely affect enrichment hybridization performance for most of the population). This Exome Supplement Pulldown (ESP) can be pooled with standard exome DNA libraries for very economical sequencing. Table 10 lists proprietary and public data sets of medical and research interest as well as the anticipated coverage gap with Illumina's TruSeq exome kit. Table 10 shows an exemplary list of nucleic acid molecules in the ESP subset.

TABLE 10

List of content in the ESP subset
Content120924LG.bed

| | | by Set | | Cumulative | | Missed in TruSeq by Set | | Missed in TruSeq Cumulative | |
|---|---|---|---|---|---|---|---|---|---|
| Priority | Content Name | Bases | Ranges | Bases | Ranges | Bases | Ranges | Bases | Ranges |
| 1 | MendelDB_snp_0913_2012.bed | 78,882 | 1,576 | 65,968 | 1,163 | 13,844 | 299 | 13,844 | 299 |
| 2 | PharmGKB_snp_0914_2012.bed | 14,600 | 292 | 80,253 | 1,444 | 8,642 | 178 | 22,486 | 477 |
| 3 | medical_dbSNP_regulome1_Suspect.bed | 22,005 | 440 | 100,522 | 1,836 | 15,796 | 323 | 38,088 | 794 |
| 4 | GeneReview_snp_0913_2012.bed | 61,615 | 1,231 | 114,970 | 2,098 | 11,459 | 249 | 41,520 | 865 |
| 5 | HGMD_ClinVar_snp_0913_2012.bed | 1,062,528 | 21,220 | 779,524 | 12,537 | 197,594 | 3,873 | 219,612 | 4,313 |
| 6 | Clinical_Channel_snp_0913_2012.bed | 771,293 | 15,404 | 928,410 | 15,103 | 219,084 | 4,239 | 324,542 | 6,309 |
| 7 | OMIM_snp_0914_2012.bed | 500,554 | 9,999 | 928,410 | 15,103 | 102,540 | 2,092 | 324,542 | 6,309 |
| 8 | Varimed_multi_ethnic_snp_0914_2012.bed | 89,201 | 1,784 | 1,002,730 | 16,568 | 77,177 | 1,568 | 391,484 | 7,660 |
| 9 | Varimed_highconf_snp_0914_2012.bed | 1,177,673 | 23,553 | 2,032,039 | 36,733 | 1,073,682 | 21,358 | 1,355,991 | 26,787 |
| 10 | HGMD_mut.bed | 4,305,255 | 84,885 | 3,421,232 | 51,658 | 556,284 | 8,900 | 1,698,980 | 31,491 |
| 11 | Exons_VIP-Genes-120713 | 233,123 | 652 | 3,604,514 | 51,812 | 49,783 | 331 | 1,738,877 | 31,691 |
| 12 | Regulome1_VIP-Genes-120713 | 3,000 | 60 | 3,606,632 | 51,850 | 2,503 | 54 | 1,740,885 | 31,732 |
| 13 | Exons_MendelDB-Genes-120916 | 14,325,633 | 40,761 | 16,091,103 | 71,703 | 3,726,418 | 19,767 | 5,049,919 | 45,516 |
| 14 | Regulome1_MendelDB-Genes-120916 | 147,553 | 2,951 | 16,201,606 | 73,825 | 125,129 | 2,553 | 5,157,542 | 47,677 |
| 15 | Exons_HGMD-Genes-120913 | 26,801,793 | 74,195 | 29,292,835 | 105,150 | 7,047,052 | 36,440 | 8,633,799 | 64,224 |
| 16 | Regulome1_HGMD-Genes-120913 | 254,356 | 5,087 | 29,381,797 | 106,849 | 214,286 | 4,372 | 8,720,429 | 65,963 |
| 17 | Exons_CancerGeneCensus_gene | 3,786,660 | 9,924 | 31,022,066 | 110,788 | 934,846 | 4,641 | 9,113,184 | 67,842 |
| 18 | Regulome1_CancerGeneCensus_gene | 31,651 | 633 | 31,031,990 | 110,976 | 27,842 | 569 | 9,122,893 | 68,033 |
| 19 | Exons_OMIM_Mendelian_gene | 19,484,727 | 54,285 | 32,499,571 | 114,516 | 5,032,796 | 26,346 | 9,518,418 | 69,854 |
| 20 | Regulome1_OMIM_Mendelian_gene | 210,906 | 4,218 | 32,522,006 | 114,944 | 179,685 | 3,668 | 9,540,226 | 70,290 |
| 21 | Exons_HGMD_Mendelian_gene | 27,988,755 | 77,427 | 35,226,837 | 121,987 | 7,363,878 | 37,504 | 10,174,050 | 73,377 |
| 22 | Regulome1_HGMD_Mendelian_gene | 266,255 | 5,325 | 35,260,944 | 122,647 | 226,927 | 4,632 | 10,207,319 | 74,046 |
| 23 | Exons_HLAclass1 | 5,969 | 24 | 35,260,944 | 122,647 | 3,554 | 26 | 10,207,319 | 74,046 |
| 24 | Regulome1_HLAclass1 | 950 | 19 | 35,260,944 | 122,647 | 743 | 15 | 10,207,319 | 74,046 |
| 25 | Exons_HLAclass2 | 28,398 | 82 | 35,273,022 | 122,664 | 11,750 | 50 | 10,209,818 | 74,060 |
| 26 | Regulome1_HLAclass2 | 350 | 7 | 35,273,098 | 122,665 | 100 | 2 | 10,209,868 | 74,061 |

TABLE 10-continued

List of content in the ESP subset
Content120924LG.bed

| | | by Set | | Cumulative | | Missed in TruSeq by Set | | Missed in TruSeq Cumulative | |
|---|---|---|---|---|---|---|---|---|---|
| Priority | Content Name | Bases | Ranges | Bases | Ranges | Bases | Ranges | Bases | Ranges |
| 27 | CFTR_Intronic | 603 | 3 | 35,273,651 | 122,667 | 603 | 3 | 10,210,421 | 74,063 |
| 28 | Triallelic_in_Footprint | 7,891 | 154 | 35,280,947 | 122,809 | 7,434 | 150 | 10,217,712 | 74,205 |
| 29 | phastConsElements46way-top0.5percent | 2,662,784 | 7,681 | 36,864,760 | 126,352 | 1,794,961 | 5,994 | 11,753,993 | 78,509 |

In content regions having very high GC content (>70%), standard sequencing typically performs poorly because the elevated $T_m$ (melting temperature) of these areas can cause poor PCR or other amplification due to competition with more numerous lower $T_m$ sequences. These sequences are also enriched for other problem, e.g. hairpins and other secondary structure. These regions are typically either skipped or perform poorly in standard sequencing. We have developed an enrichment process to target content areas of high GC content (HGCP) and have developed customized sample preparation and sequencing protocols to specifically improve the performance of this library by optimizing temperatures, incubation times, buffers and enzymes. An example composition of such a library intersected with our content is shown in Table 11.

with standard enrichment strategies. Genomic regions outside the exome (such as introns of HLA) are typically not targeted by exome sequencing. The difficulties in sequencing may be due to poor enrichment efficiency, degenerate mapping of reads and inadequate read length to span common simple tandem repeats or biomedically relevant expanding repeats. We addressed these problems by developing a specific enrichment pulldown (LRP) and protocol to extract primarily these regions for more expensive long paired read sequencing (e.g. 2×250 bp on Illumina MiSeq) or long single read sequencing (e.g., 5 kb single molecule sequencing on PacBio RS or future technologies as available). This longer read sequencing technology is currently 10-fold to several 100-fold more expensive per base than bulk sequencing and is often not currently commercially

TABLE 11

Exemplary list of content in the HGCP subset
HGCPmerge100_120924LG.bed Includes 50 bp dilation

| | | by Set | | Cumulative | | HGCP by Set | | HGCP Cumulative | |
|---|---|---|---|---|---|---|---|---|---|
| Priority | Content Name | Bases | Ranges | Bases | Ranges | Basest | Ranges | Bases | Ranges |
| | MendelDB_snp_0913_2012.bed | 180,101 | 909 | 180,101 | 909 | 12,539 | 89 | 12,539 | 89 |
| | PharmGKB_snp_0914_2012.bed | 42,673 | 266 | 222,474 | 1,173 | 3,092 | 22 | 15,631 | 111 |
| | medical_dbSNP_regulome1_Suspect.bed | 62,226 | 390 | 281,629 | 1,547 | 883 | 7 | 16,387 | 116 |
| | GeneReview_snp_0913_2012.bed | 143,233 | 753 | 322,106 | 1,765 | 11,074 | 77 | 20,586 | 145 |
| | HGMD_ClinVar_snp_0913_2012.bed | 1,881,403 | 8,749 | 1,976,714 | 9,287 | 162,863 | 948 | 166,434 | 971 |
| | Clinical_Channel_snp_0913_2012.bed | 1,553,729 | 7,442 | 2,382,381 | 11,058 | 112,701 | 674 | 185,369 | 1,075 |
| | OMIM_snp_0914_2012.bed | 1,091,353 | 5,527 | 2,382,381 | 11,058 | 92,276 | 563 | 185,369 | 1,075 |
| | Varimed_multi_ethnic_snp_0914_2012.bed | 269,869 | 1,600 | 2,609,304 | 12,341 | 4,066 | 29 | 188,395 | 1,097 |
| | Varimed_highconf_snp_0914_2012.bed | 3,538,004 | 19,531 | 5,749,403 | 29,271 | 26,929 | 203 | 208,093 | 1,244 |
| | HGMD_mut.bed | 4,713,066 | 18,283 | 8,448,253 | 37,978 | 448,145 | 2,157 | 481,839 | 2,386 |
| | Exons_VIP-Genes-120713 | 301,582 | 564 | 8,655,649 | 38,208 | 31,335 | 100 | 506,873 | 2,445 |
| | Regulome1_VIP-Genes-120713 | 9,180 | 48 | 8,661,738 | 38,231 | 0 | 0 | 506,873 | 2,445 |
| | Exons_MendelDB-Genes-120916 | 18,594,872 | 32,943 | 23,550,190 | 57,802 | 1,986,487 | 6,270 | 2,147,437 | 7,091 |
| | Regulome1_MendelDB-Genes-120916 | 445,360 | 2,606 | 23,890,795 | 59,262 | 9,488 | 77 | 2,151,072 | 7,110 |
| | Exons_HGMD-Genes-120913 | 34,574,073 | 60,810 | 40,302,799 | 85,129 | 3,697,923 | 11,625 | 3,918,341 | 12,444 |
| | Regulome1_HGMD-Genes-120913 | 765,607 | 4,447 | 40,572,922 | 86,302 | 14,220 | 115 | 3,921,622 | 12,455 |
| | Exons_CancerGeneCensus_gene | 4,823,472 | 8,240 | 42,627,241 | 89,578 | 526,402 | 1,590 | 4,139,209 | 13,145 |
| | Regulome1_CancerGeneCensus_gene | 95,341 | 581 | 42,657,367 | 89,729 | 2,374 | 17 | 4,140,165 | 13,150 |
| | Exons_OMIM_Mendelian_gene | 25,166,172 | 44,269 | 44,497,746 | 92,630 | 2,702,676 | 8,437 | 4,340,856 | 13,745 |
| | Regulome1_OMIM_Mendelian_gene | 636,246 | 3,726 | 44,567,099 | 92,943 | 14,171 | 111 | 4,342,155 | 13,751 |
| | Exons_HGMD_Mendelian_gene | 36,090,180 | 63,709 | 48,011,279 | 98,805 | 3,871,482 | 12,113 | 4,684,379 | 14,795 |
| | Regulome1_HGMD_Mendelian_gene | 802,747 | 4,700 | 48,116,355 | 99,290 | 17,080 | 133 | 4,685,899 | 14,802 |
| | Exons_HLAclass1 | 8,432 | 9 | 48,116,355 | 99,290 | 3,128 | 3 | 4,685,899 | 14,802 |
| | Regulome1_HLAclass1 | 2,995 | 10 | 48,116,355 | 99,290 | 0 | 0 | 4,685,899 | 14,802 |
| | Exons_HLAclass2 | 38,082 | 65 | 48,130,838 | 99,292 | 1,017 | 6 | 4,686,134 | 14,804 |
| | Regulome1_HLAclass2 | 913 | 5 | 48,130,855 | 99,292 | 0 | 0 | 4,686,134 | 14,804 |
| | CFTR_Intronic | 903 | 3 | 48,131,608 | 99,294 | 0 | 0 | 4,686,134 | 14,804 |
| | Triallelic_in_Footprint | 23,509 | 128 | 48,154,196 | 99,400 | 632 | 4 | 4,686,366 | 14,806 |
| | phastConsElements46way-top0.5percent | 3,417,667 | 6,728 | 50,091,253 | 102,331 | 162,245 | 531 | 4,721,759 | 14,903 |

Repetitive elements in the genome and other genomic regions outside of the exome can be difficult to sequence, align and/or assemble, particularly with short read technology (e.g. 2×100 on Illumina HiSeq). Many of these regions in the exome are skipped or perform poorly with standard viable for the entire content regions. Furthermore, in some case (e.g. PacBio RS) the raw error profile is problematic for general use in SNV calling. However for some types of important problems it these technologies are required for accurate or clinical quality results to correctly map degenerate sequence or span a repeat sequence. We have developed a bulk protocol in which all such regions separated into a subset and are sequenced in parallel to achieve a useful economy of scale for the preparation yet still limit the total amount of sequencing to a practical amount. In addition to sequencing this with a different technology, we have customized our alignment and other bioinformatic pipeline elements to best leverage these longer reads to improve coverage, accuracy and characterization (e.g. allelotyping STRs and unstable expanding repeat regions). Phasing and/or haplotyping of HLA and blood typing genes is more tractable using longer reads and longer molecules provided in this library. Reassembly of ambiguous regions is more tractable using the longer molecules and reads from these libraries. An example composition of such a library is listed in Table 12. In addition the intersection of this library with particular classes of problem or genomic content is shown in the final block.

TABLE 12

LRPmerge300_120924LG.bed Includes 100 bp dilation

| Priority | | by Set | | Cumulative | | LRP by Set | | LRP Cumulative | |
|---|---|---|---|---|---|---|---|---|---|
| | | Bases | Ranges | Bases | Ranges | Basest | Ranges | Bases | Ranges |
| | Content Name | | | | | | | | |
| | MendelDB_snp_0913_2012.bed | 300,380 | 823 | 300,380 | 823 | 83,107 | 238 | 83,107 | 238 |
| | PharmGKB_snp_0914_2012.bed | 71,926 | 258 | 372,876 | 1,076 | 17,087 | 65 | 100,722 | 302 |
| | medical_dbSNP_regulome1_Suspect.bed | 107,508 | 371 | 474,890 | 1,433 | 77,284 | 267 | 173,712 | 560 |
| | GeneReview_snp_0913_2012.bed | 239,363 | 690 | 542,080 | 1,635 | 72,372 | 210 | 194,354 | 624 |
| | HGMD_ClinVar_snp_0913_2012.bed | 3,074,892 | 7,774 | 3,241,005 | 8,261 | 945,906 | 2,543 | 1,022,992 | 2,782 |
| | Clinical_Channel_snp_0913_2012.bed | 2,537,774 | 6,684 | 3,880,310 | 9,829 | 723,269 | 2,045 | 1,162,383 | 3,154 |
| | OMIM_snp_0914_2012.bed | 1,811,109 | 5,019 | 3,880,310 | 9,829 | 554,960 | 1,605 | 1,162,383 | 3,154 |
| | Varimed_multi_ethnic_snp_0914_2012.bed | 484,477 | 1,439 | 4,295,467 | 10,934 | 153,156 | 419 | 1,299,826 | 3,485 |
| | Varimed_highconf_snp_0914_2012.bed | 6,365,502 | 16,815 | 9,980,716 | 25,215 | 1,574,979 | 3,476 | 2,671,355 | 6,283 |
| | HGMD_mut.bed | 7,400,636 | 15,605 | 14,095,445 | 32,199 | 2,199,289 | 4,999 | 3,861,157 | 8,525 |
| | Exons_VIP-Genes-120713 | 387,447 | 472 | 14,341,711 | 32,377 | 147,978 | 194 | 3,958,330 | 8,621 |
| | Regulome1_VIP-Genes-120713 | 15,830 | 41 | 14,353,492 | 32,387 | 5,972 | 14 | 3,962,756 | 8,624 |
| | Exons_MendelDB-Genes-120916 | 23,887,624 | 26,913 | 32,552,166 | 47,917 | 7,780,357 | 11,130 | 10,049,097 | 16,057 |
| | Regulome1_MendelDB-Genes-120916 | 794,991 | 2,347 | 33,211,287 | 48,852 | 150,309 | 470 | 10,133,001 | 16,215 |
| | Exons_HGMD-Genes-120913 | 44,321,062 | 49,866 | 53,983,227 | 69,498 | 14,883,355 | 21,110 | 17,258,590 | 25,544 |
| | Regulome1_HGMD-Genes-120913 | 1,355,456 | 4,013 | 54,494,848 | 70,283 | 266,188 | 794 | 17,324,858 | 25,670 |
| | Exons_CancerGeneCensus_gene | 6,121,488 | 6,826 | 57,070,263 | 72,967 | 2,045,184 | 2,809 | 18,218,353 | 26,867 |
| | Regulome1_CancerGeneCensus_gene | 173,742 | 520 | 57,133,995 | 73,058 | 27,135 | 94 | 18,229,400 | 26,886 |
| | Exons_OMIM_Mendelian_gene | 32,224,942 | 36,331 | 59,444,387 | 75,405 | 10,505,055 | 15,008 | 18,976,117 | 27,934 |
| | Regulome1_OMIM_Mendelian_gene | 1,129,215 | 3,368 | 59,571,025 | 75,634 | 191,633 | 620 | 18,989,192 | 27,963 |
| | Exons_HGMD_Mendelian_gene | 46,253,280 | 52,403 | 63,975,577 | 80,407 | 15,161,059 | 21,685 | 20,193,619 | 29,734 |
| | Regulome1_HGMD_Mendelian_gene | 1,416,254 | 4,273 | 64,173,958 | 80,756 | 248,193 | 810 | 20,221,296 | 29,790 |
| | Exons_HLAclass1 | 10,894 | 3 | 64,173,958 | 80,756 | 10,894 | 3 | 20,221,296 | 29,790 |
| | Regulome1_HLAclass1 | 5,912 | 6 | 64,173,958 | 80,756 | 5,912 | 6 | 20,221,296 | 29,790 |
| | Exons_HLAclass2 | 50,951 | 42 | 64,188,111 | 80,758 | 50,951 | 42 | 20,235,449 | 29,792 |
| | Regulome1_HLAclass2 | 2,196 | 3 | 64,188,111 | 80,758 | 2,196 | 3 | 20,235,449 | 29,792 |
| | CCTR_Intronic | 1,203 | 3 | 64,189,624 | 80,759 | 0 | 0 | 20,235,449 | 29,792 |
| | Triallelic_in_Footprint | 39,060 | 117 | 64,232,417 | 80,836 | 36,957 | 109 | 20,276,075 | 29,864 |
| | phastConsElements46way-top0.5percent | 4,269,676 | 6,189 | 66,642,340 | 83,243 | 1,011,328 | 1,857 | 20,709,245 | 30,497 |
| | HLA-ClassI | 22,744 | 3 | 66,651,185 | 83,238 | 22,744 | 3 | 20,718,090 | 30,492 |
| | HLA-ClassII | 140,811 | 10 | 66,728,362 | 83,207 | 140,811 | 10 | 20,795,267 | 30,461 |
| | BloodTypingf10k | 206,568 | 3 | 66,902,785 | 83,169 | 206,568 | 3 | 20,972,246 | 30,428 |
| | AmylaseRegion | 300,200 | 1 | 67,200,752 | 83,169 | 300,200 | 1 | 21,271,226 | 30,427 |
| | ImportantCompressions | 192,112 | 3 | 67,379,340 | 83,156 | 192,112 | 3 | 21,449,546 | 30,416 |
| | SMN1_SMN2 | 57,657 | 2 | 67,428,632 | 83,146 | 57,657 | 2 | 21,498,838 | 30,406 |
| | Problem Name | | | | | | | | |
| | v3NoCoverage | 51,511,046 | 26,632 | 51,506,246 | 26,608 | 756,946 | 947 | 756,946 | 947 |
| | ShortPEReadMappabilty | 131,941,961 | 31,071 | 135,610,684 | 40,898 | 1,415,767 | 1,581 | 1,445,847 | 1,660 |
| | SingleReadMappabilty | 239,094,172 | 149,523 | 241,428,271 | 156,194 | 2,364,928 | 3,258 | 2,382,194 | 3,311 |
| | ValidatedCompressions | 3,262,543 | 36 | 244,073,867 | 155,934 | 54,267 | 71 | 2,427,518 | 3,363 |
| | SegmentalDuplications | 162,351,720 | 6,902 | 287,784,823 | 145,772 | 4,084,205 | 4,129 | 4,393,421 | 4,945 |
| | STR>50bp | 128,885,115 | 201,050 | 395,004,522 | 297,226 | 1,209,546 | 2,883 | 5,359,052 | 7,494 |
| | GRCh37patches | 61,247,019 | 134 | 433,409,533 | 292,018 | 3,302,921 | 3,265 | 7,821,274 | 9,930 |
| | v3LowCoverage | 746,244,957 | 683,267 | 966,704,005 | 689,651 | 15,671,569 | 25,812 | 20,709,245 | 30,497 |
| | HLA-ClassI | 22,744 | 3 | 966,704,005 | 689,651 | 22,744 | 3 | 20,718,090 | 30,492 |
| | HLA-ClassII | 140,811 | 10 | 966,704,005 | 689,651 | 140,811 | 10 | 20,795,267 | 30,461 |
| | BloodTypingf10k | 206,568 | 3 | 966,723,788 | 689,642 | 206,568 | 3 | 20,972,246 | 30,428 |
| | AmylaseRegion | 300,200 | 1 | 966,815,712 | 689,618 | 300,200 | 1 | 21,271,226 | 30,427 |
| | ImportantCompressions | 192,112 | 3 | 966,817,041 | 689,617 | 192,112 | 3 | 21,449,546 | 30,416 |
| | SMN1_SMN2 | 57,657 | 2 | 966,817,041 | 689,617 | 57,657 | 2 | 21,498,838 | 30,406 |

We have developed all three of these libraries and have preliminary data combining standard TruSeq Exome and ESP to produce what we call Exome+, Extended Exome or ACE (Accuracy and Content Enhanced) Exome (Tables 13-14). This significantly improves coverage of the RefSeq exons, our customized Exome as well as dramatic improvement on customized Variants (as many of these are outside the exome).

TABLE 13

| | | | Product Category | | | | | | | |
|---|---|---|---|---|---|---|---|---|---|---|
| | | | Whole Genome | | Whole Exome | | | | Description of comparison metrics | |
| | | | Full Flowcell (PL 2.0) | | TruSEqExome (PL 2.0) B ~Price Point | | Extended Exome (E+, ESP) (Alpha demo in P1) A | | | |
| | Set Size | | Personalis 92x | | Personalis 54x | | Personalis 56x | | | |
| | Size | Unit | A | B | A | B | A | B | A | B |
| NEMAR corrections | | | | | | | | | | |
| NEMAR.DegappedGenome | 1,102 kbp | | 765,476 | 64,324 | 25,409 | 3,170 | 31,894 | 3,522 | Homozygous major allele "variants" removed | Homozygous minor allele "variants" called |
| NEMAR.RefSeqExons | 17,999 kbp | | 12,488 | 1,059 | 10,436 | 1,045 | 11,224 | 1,046 | | |
| NEMAR.RefSeqCodingExons | 6,692 kbp | | 4,713 | 383 | 4,460 | 419 | 4,573 | 393 | | |
| NEMAR.RefSeqUTR | 11,307 kbp | | 7,775 | 676 | 5,976 | 626 | 6,651 | 653 | | |
| NEMAR.PersonalisExome | 7,394 kbp | | 5,029 | 435 | 4,356 | 446 | 4,915 | 468 | | |
| NEMAR.PersonalisVariants | 4,050 kbp | | 2,171 | 360 | 376 | 72 | 1,851 | 371 | | |
| NEMAR.PersonalisNetContent | 11,080 kbp | | 7,005 | 769 | 4,547 | 489 | 6,573 | 812 | | |
| Reference | | | | | | | | | | |
| DegappedGenome | 2,861 Mbp | | 98.7% | 51 | 3.7% | 50 | 5.1% | 49 | Coverage % of target reported (GC > 50, not LowQual) | Error: −10log10(#Errors/SetSize) (1-Specificity) (GQ > 50, not LowQual) |
| RefSeqExons | 70,467 kbp | | 98.7% | 52 | 77.9% | 49 | 88.1% | 48 | | |
| RefSeqCodingExons | 33,366 kbp | | 99.0% | 53 | 85.4% | 49 | 94.7% | 48 | | |
| RefSeqUTR | 37,101 kbp | | 98.4% | 52 | 69.1% | 50 | 80.3% | 48 | | |
| PersonalisExome | 29,056 kbp | | 99.2% | 53 | 81.3% | 49 | 94.2% | 48 | | |
| PersonalisVariants | 172 kbp | | 99.8% | 49 | 83.0% | 49 | 96.0% | 47 | | |
| PersonalisNetContent | 29,095 kbp | | 99.3% | 53 | 80.0% | 49 | 93.9% | 48 | | |
| Content.RefSeqFirstCodingExons | 2,389 kbp | | 99.1% | 53 | 74.0% | 47 | 89.0% | 48 | | |
| Content.GCgt70 | 1,639 kbp | | 99.0% | 53 | 38.2% | 48 | 65.6% | 47 | | |
| Content.NoMapPEO | 903 kbp | | 71.0% | 46 | 54.0% | 38 | 61.1% | 36 | | |

Bronze Genome

TABLE 13-continued

| | | | Product Category | | | | | | | |
|---|---|---|---|---|---|---|---|---|---|---|
| | | | Whole Genome | | Whole Exome | | | | | |
| | | | | | Product Type | | | | | |
| | | | Full Flowcell (PL 2.0) | | TruSEqExome (PL 2.0) B ~Price Point | | Extended Exome (E+, ESP) (Alpha demo in P1) A | | Description of comparison metrics | |
| | Set Size | | Personalis 92x | | Personalis 54x | | Personalis 56x | | | |
| | Size | Unit | A | B | A | B | A | B | A | B |
| Content.Segmental_Duplications | 2,046 | kbp | 89.1% | 43 | 71.9% | 38 | 77.5% | 37 | Coverage % of target reported (GQ > 50, not LowQual) | Error: % Discordance/VariantLoci (1-Sensitivity) (GQ > 50, not LowQual) |
| Content.HomopolymerFlank | 136 | kbp | 97.2% | 44 | 57.7% | 41 | 77.3% | 37 | | |
| Content.STRgt50f50 | 453 | kbp | 94.0% | 42 | 66.8% | 34 | 77.2% | 33 | | |
| SNPs | | | | | | | | | | |
| DegappedGenome | 2,861 | Mbp | 95.3% | 0.34% | 1.9% | 1.65% | 3.0% | 1.26% | | |
| RefSeqExons | 70,467 | kbp | 95.8% | 0.21% | 61.9% | 1.60% | 76.6% | 1.46% | | |
| RefSeqCodingExons | 33,366 | kbp | 95.0% | 0.19% | 69.7% | 1.61% | 85.4% | 1.50% | | |
| RefSeqUTR | 37,101 | kbp | 96.3% | 0.22% | 57.2% | 1.60% | 71.3% | 1.44% | | |
| PersonalisExome | 29,056 | kbp | 95.6% | 0.21% | 64.0% | 1.50% | 83.3% | 1.30% | | |
| PersonalisVariants | 172 | kbp | 99.8% | 0.02% | 12.6% | 0.31% | 72.7% | 0.10% | | |
| PersonalisNetContent | 29,095 | kbp | 97.0% | 0.14% | 44.1% | 1.44% | 79.1% | 0.93% | | |
| Content.RefSeqFirstCodingExons | 2,389 | kbp | 92.8% | 0.10% | 60.5% | 1.17% | 76.5% | 0.74% | | |
| Content.GCgt70 | 1,639 | kbp | 91.2% | 0.11% | 24.3% | 1.21% | 47.9% | 0.82% | | |
| Content.NoMapPEO | 903 | kbp | 65.4% | 1.06% | 46.3% | 10.98% | 56.1% | 8.72% | | |
| Content.Segmental_Duplications | 2,046 | kbp | 83.6% | 0.97% | 56.2% | 7.00% | 65.0% | 7.01% | | |
| Content.HomopolymerFlank | 136 | kbp | 81.8% | 1.28% | 23.1% | 13.64% | 50.3% | 7.64% | | |
| Content.STRgt50f50 | 453 | kbp | 76.6% | 1.29% | 59.1% | 9.90% | 68.1% | 9.94% | | |

TABLE 14

| Genomic Region | Library | Reference Loci | | Variant Loci | | All Loci | | Region Definition |
|---|---|---|---|---|---|---|---|---|
| | | HQ Cov | Phred Error | HQ Cov | Error % | HQ Cov | Phred Error | |
| RefSeq | TruSeq | 79.6% | 49 | 64.0% | 1.55% | 78.6% | 46 | All exons and UTRs |
| | Exome+ | 88.1% | 48 | 76.6% | 1.46% | 87.3% | 46 | |
| Interpretable | TruSeq | 83.2% | 49 | 65.8% | 1.43% | 82.3% | 47 | 46 PharmGKB VIP genes |
| Exome | Exome+ | 94.2% | 48 | 83.3% | 1.30% | 93.6% | 46 | 1,803 MendelDB genes |
| | | | | | | | | 3,502 HGMD genes |
| | | | | | | | | 488 Cancer genes |
| | | | | | | | | 2,896 OMIM Mendelian genes |
| | | | | | | | | 3,493 HGMD Mendelian genes |
| | | | | | | | | (90-95% of symbols covered in ESP v1) |
| Interpretable | TruSeq | 85.2% | 46 | 13.3% | 0.24% | 78.6% | 43 | MendelDB SNP |
| Variants | Exome+ | 96.0% | 47 | 72.7% | 0.10% | 93.9% | 41 | PharmGKB SNP |
| | | | | | | | | Medical dbSNP Regulome1 suspect |
| | | | | | | | | GeneReview SNP |
| | | | | | | | | HGMD Clinvar SNP |
| | | | | | | | | Clinical Channel SNP |
| | | | | | | | | OMIM SNP |
| | | | | | | | | Varimed Multiethnic SNP |
| | | | | | | | | Varimed High Confidence SNP |

It should be understood from the foregoing that, while particular implementations have been illustrated and described, various modifications may be made thereto and are contemplated herein. An embodiment of one aspect of the disclosure may be combined with or modified by an embodiment of another aspect of the disclosure. It is not intended that the invention(s) be limited by the specific examples provided within the specification. While the invention(s) has (or have) been described with reference to the aforementioned specification, the descriptions and illustrations of embodiments of the invention(s) herein are not meant to be construed in a limiting sense. Furthermore, it shall be understood that all aspects of the invention(s) are not limited to the specific depictions, configurations or relative proportions set forth herein which depend upon a variety of conditions and variables. Various modifications in form and detail of the embodiments of the invention(s) will be apparent to a person skilled in the art. It is therefore contemplated that the invention(s) shall also cover any such modifications, variations and equivalents.

What is claimed is:

1. A method for processing a nucleic acid sample, comprising:
    (a) generating at least a first subset of nucleic acid molecules and a second subset of nucleic acid molecules from said nucleic acid sample with the aid of pulldown probes that selectively enrich for one or more features in at least said first subset of nucleic acid molecules or said second subset of nucleic acid molecules such that said first subset of nucleic acid molecules and said second subset of nucleic acid molecules differ by said one or more features, wherein said one or more features are selected from the group consisting of non-human sequence(s), alternate sequence(s), non-reference sequence(s), sequence(s) of genes with known disease traits, sequence(s) of genes with known drug traits, sequence(s) of genes with known biomedically interpretable variants, reassembly gene sequence(s), and any combination thereof; and
    (b) combining at least said first subset of nucleic acid molecules and said second subset of nucleic acid molecules to produce a combined pool of nucleic acid molecules, and conducting one or more assays on at least a subset of said combined pool of nucleic acid molecules or a derivative thereof, wherein said one or more assays comprises a sequencing reaction.

2. The method of claim 1, wherein said alternate sequence(s) are uniquely derived from a plurality of human reference sequence(s).

3. The method of claim 2, wherein said plurality of human reference sequence(s) includes GRCh37 or GRCh37 patches.

4. The method of claim 1, wherein said non-human sequence(s) comprises pathogen-derived sequence(s).

5. The method of claim 4, wherein said pathogen-derived sequence(s) is derived from a virus, bacteria, fungus, amoeba or any combination thereof.

6. The method of claim 1, wherein (a) comprises conducting one or more hybridization reactions using said pulldown probes to selectively enrich for said one or more features.

7. The method of claim 1, further comprising, prior to (b), conducting differential amplification of at least said first subset of nucleic acid molecules and said second subset of nucleic acid molecules based on said one or more features.

8. The method of claim 1, wherein conducting said one or more assays comprises conducting two or more assays, and wherein (b) further comprises combining results from said two or more assays.

9. The method of claim 1, further comprising producing one or more biomedical reports after conducting said one or more assays, wherein said one or more biomedical reports combines results from said one or more assays.

10. The method of claim 9, wherein said one or more biomedical reports include information indicative of a presence or absence of said one or more features selected from the group consisting of a non-human sequence(s), alternate sequence(s), non-reference sequence(s), sequence(s) of genes with known disease traits, sequence(s) of genes with known drug traits, sequence(s) of genes with known biomedically interpretable variants, reassembly gene sequence(s), and any combination thereof.

11. The method of claim 9, wherein said one or more features comprises said non-human sequence(s), and wherein said one or more biomedical reports includes information indicative of at least one non-human species associated with said non-human sequence(s).

12. The method of claim 11, wherein said non-human sequence(s) comprises a pathogen-derived sequence(s), and wherein said one or more biomedical reports includes information indicative of at least one pathogen associated with said pathogen-derived sequence(s).

13. The method of claim 9, wherein said one or more biomedical reports identify said one or more features selected from the group consisting of a non-human sequence(s), alternate sequence(s), non-reference sequence(s), sequence(s) of genes with known disease traits, sequence(s) of genes with known drug traits, sequence(s) of genes with known biomedically interpretable variants, reassembly gene sequence(s), and any combination thereof.

14. The method of claim 9, wherein said one or more biomedical reports identify said non-human sequence(s) or pathogen from which said non-human sequence(s) is derived.

15. The method of claim 14, wherein said one or more biomedical reports identify said pathogen from which said non-human sequence(s) is derived.

16. The method of claim 14, wherein said one or more biomedical reports identify said non-human sequence(s).

17. The method of claim 1, wherein said first subset of nucleic acid molecules differs from said second subset of nucleic acid molecules by said reassembly gene sequence(s).

18. The method of claim 1, wherein said first subset of nucleic acid molecules differs from said second subset of nucleic acid molecules by said alternate sequence(s).

19. The method of claim 1, wherein said first subset of nucleic acid molecules represents an exome and said second subset of nucleic acid molecules represents a clinically-relevant subset of genes.

20. The method of claim 1, wherein said first subset of nucleic acid molecules differs from said second subset of nucleic acid molecules by said non-human sequence(s).

21. The method of claim 1, wherein said first subset of nucleic acid molecules differs from said second subset of nucleic acid molecules by said sequence(s) of genes with known disease traits.

22. The method of claim 1, wherein said first subset of nucleic acid molecules differs from said second subset of nucleic acid molecules by said sequence(s) of genes with known drug traits.

23. The method of claim 1, wherein said first subset of nucleic acid molecules differs from said second subset of nucleic acid molecules by said sequence(s) of genes with known biomedically interpretable variants.

24. The method of claim 1, wherein said first subset of nucleic acid molecules differs from said second subset of nucleic acid molecules by said non-reference sequence(s).

25. The method of claim 1, wherein (a) further comprises generating a third subset of nucleic acid molecules from said nucleic acid sample.

26. The method of claim 1, wherein said first subset of nucleic acid molecules and said second subset of nucleic acid molecules differ by said non-human sequence(s), said alternate sequence(s), said non-reference sequence(s), or said reassembly gene sequence(s).

* * * * *